US008304397B2

(12) United States Patent
Olson et al.

(10) Patent No.: US 8,304,397 B2
(45) Date of Patent: Nov. 6, 2012

(54) IDENTIFICATION OF A MICRO-RNA THAT ACTIVATES EXPRESSION OF β-MYOSIN HEAVY CHAIN

(75) Inventors: Eric Olson, Dallas, TX (US); Eva Van Rooij, Boulder, CO (US)

(73) Assignee: Board of Regents, The University of Texas System, Austin, TX (US)

( * ) Notice: Subject to any disclaimer, the term of this patent is extended or adjusted under 35 U.S.C. 154(b) by 1465 days.

(21) Appl. No.: 11/831,427

(22) Filed: Jul. 31, 2007

(65) Prior Publication Data
US 2009/0180957 A1 Jul. 16, 2009

Related U.S. Application Data

(60) Provisional application No. 60/834,667, filed on Aug. 1, 2006.

(51) Int. Cl.
*A61K 35/00* (2006.01)
*A61K 48/00* (2006.01)
*C07H 21/02* (2006.01)
*C07H 21/04* (2006.01)

(52) U.S. Cl. ........ 514/44; 536/24.5; 536/23.1; 424/93.1

(58) Field of Classification Search ........... 435/6, 91.31, 435/455; 514/1, 2, 44; 536/23.1, 24.5
See application file for complete search history.

(56) References Cited

U.S. PATENT DOCUMENTS

| | | | |
|---|---|---|---|
| 6,632,628 B1 * | 10/2003 | Olson et al. | ...................... 435/18 |
| 7,232,806 B2 | 6/2007 | Tuschl et al. | |
| 2004/0157790 A1 | 8/2004 | Herweijer et al. | |
| 2005/0059005 A1 | 3/2005 | Tuschl et al. | |
| 2005/0075492 A1 | 4/2005 | Chen et al. | |
| 2005/0124568 A1 | 6/2005 | Usman et al. | |
| 2005/0261218 A1 * | 11/2005 | Esau et al. | ...................... 514/44 |
| 2006/0019286 A1 | 1/2006 | Horvitz et al. | |
| 2006/0185027 A1 | 8/2006 | Bartel et al. | |
| 2007/0287179 A1 | 12/2007 | Tuschl et al. | |
| 2007/0292878 A1 | 12/2007 | Raymond | |
| 2008/0050744 A1 | 2/2008 | Brown et al. | |
| 2008/0176766 A1 | 7/2008 | Brown et al. | |
| 2008/0214437 A1 | 9/2008 | Mohapatra et al. | |

FOREIGN PATENT DOCUMENTS

| | | |
|---|---|---|
| EP | 1959012 A2 | 8/2008 |
| WO | WO 2005/013901 A2 | 2/2005 |
| WO | WO 2005/017145 A1 | 2/2005 |
| WO | WO 2005/078096 A2 | 8/2005 |
| WO | WO 2005/078139 A2 | 8/2005 |
| WO | WO 2005/079397 A2 | 9/2005 |
| WO | WO 2005/118806 A2 | 12/2005 |
| WO | WO 2006/063356 A1 | 6/2006 |
| WO | WO 2006/111512 A1 | 10/2006 |
| WO | WO 2006/137941 A2 | 12/2006 |
| WO | WO 2007/000668 A2 | 1/2007 |
| WO | WO 2007/070483 A2 | 6/2007 |
| WO | WO 2007/090073 A2 | 8/2007 |
| WO | WO 2007/112754 A2 | 10/2007 |
| WO | WO 2008/016924 A2 | 2/2008 |
| WO | WO 2008/042231 A2 | 4/2008 |
| WO | WO 2008/043521 A2 | 4/2008 |
| WO | WO 2008/061537 A2 | 5/2008 |
| WO | WO 2008/074328 A2 | 6/2008 |
| WO | WO 2008/076324 A2 | 6/2008 |
| WO | WO 2008/016924 A3 | 8/2008 |
| WO | WO 2008/147839 A1 | 12/2008 |
| WO | WO 2009/026576 A1 | 2/2009 |

OTHER PUBLICATIONS

Crooke, S., Ann. Rev. Medicine, vol. 55, pp. 61-95 (2004).*
Peracchi et al., Rev. Med. Virol., vol. 14, pp. 47-64 (2004).*
Agrawal et al., Molecular Med. Today, vol. 6, pp. 72-81 (2000).*
Chirila et al., Biomaterials, vol. 23, pp. 321-342 (2002).*
Opalinska et al., Nature Rev., vol. 1, pp. 503-514 (2002).*
Jang et al., Expert Rev. Medical Devices, vol. 1, No. 1, pp. 127-138 (2004).*
Krutzfeldt, J., et al. (2005) Silencing of microRNAs in vivo with 'antagomirs'. Nature, v.438, pp. 685-689.*
Myocardial Infarction definition [online]. [retrieved on Feb. 23, 2012]. Retrieved from the Internet: <http://www.credoreference.com/entry.do?id=6584661>.*
Stoltner, International Search Report and Written Opinion for PCT/US2007/074866, 14 pages (mailed Jun. 20, 2008).
Lagos-Quintana et al., "New microRNAs from mouse and human," RNA, vol. 9:175-179, 2003.
Lagos-Quintana et al., "Identification of tissue-specific microRNAs from mouse," Current Biology, vol. 12:735-739, 2002.
Sempere et al., "Expression profiling of mammalian microRNAs uncovers a subset of brain-expressed microRNAs with possible roles in murine and human neuronal differentiation," Genome Biology, vol. 5:R13, 2004.

* cited by examiner

*Primary Examiner* — Jennifer Pitrak McDonald
(74) *Attorney, Agent, or Firm* — Cooley LLP

(57) ABSTRACT

The present invention relates to the identification of a microRNA, miR-208, that induces the expression of β-myosin heavy chain (β-MHC) and represses fast skeletal muscle contractile protein genes. Inhibition of this function is proposed as a treatment for cardiac fibrosis, hypertrophy and/or heart failure, and augmentation of this function can be used to repress slow fiber genes and activate fast fiber genes in the treatment of musculoskeletal disorders.

34 Claims, 32 Drawing Sheets

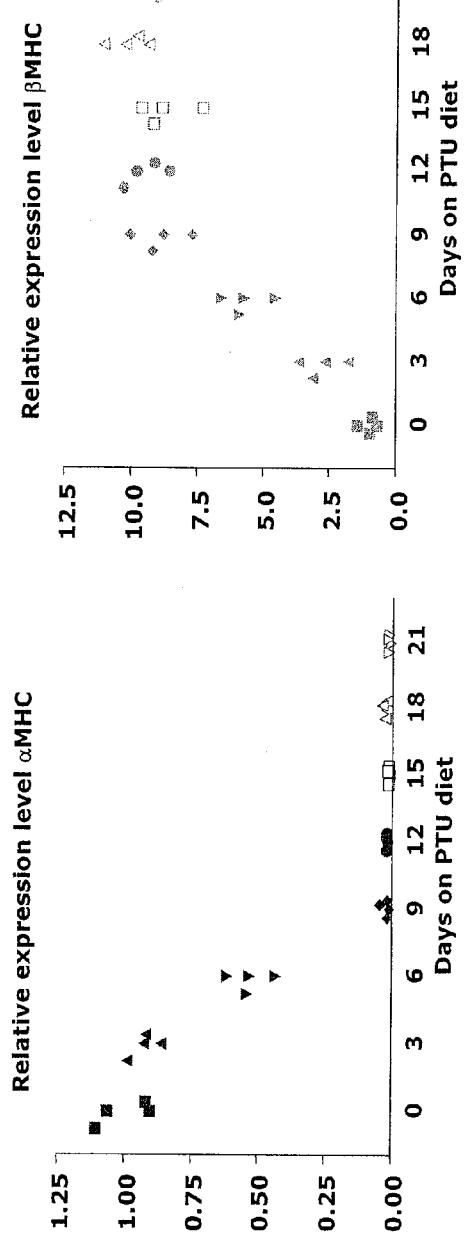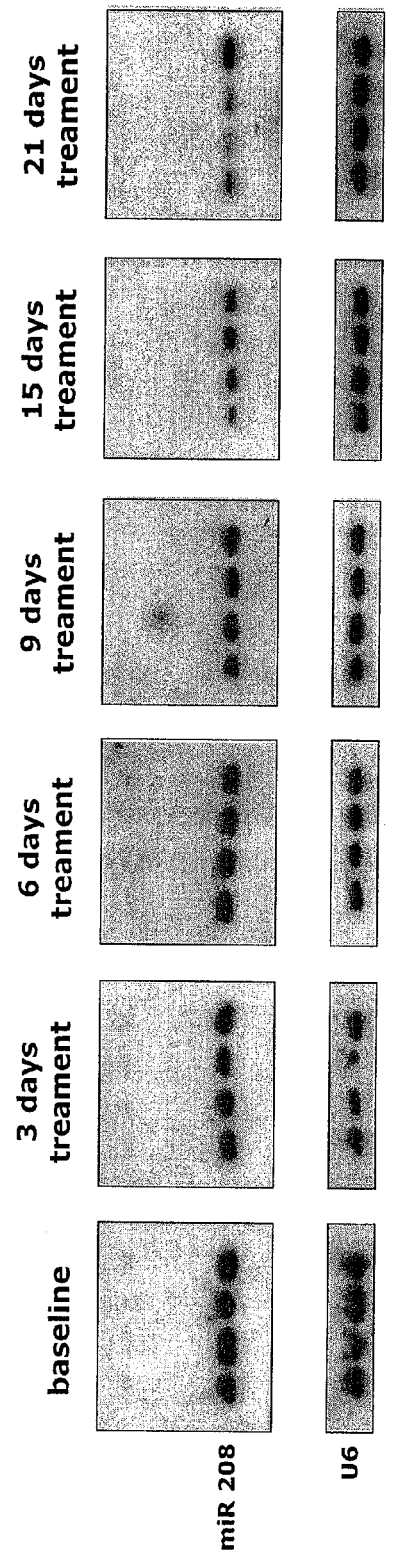
FIG. 4A
FIG. 4B
FIG. 4C

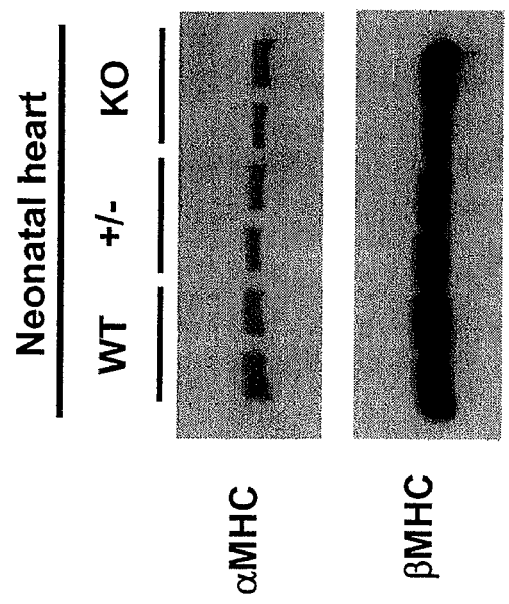
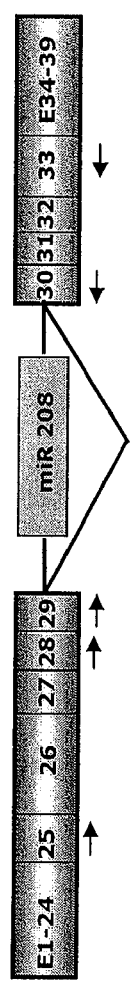
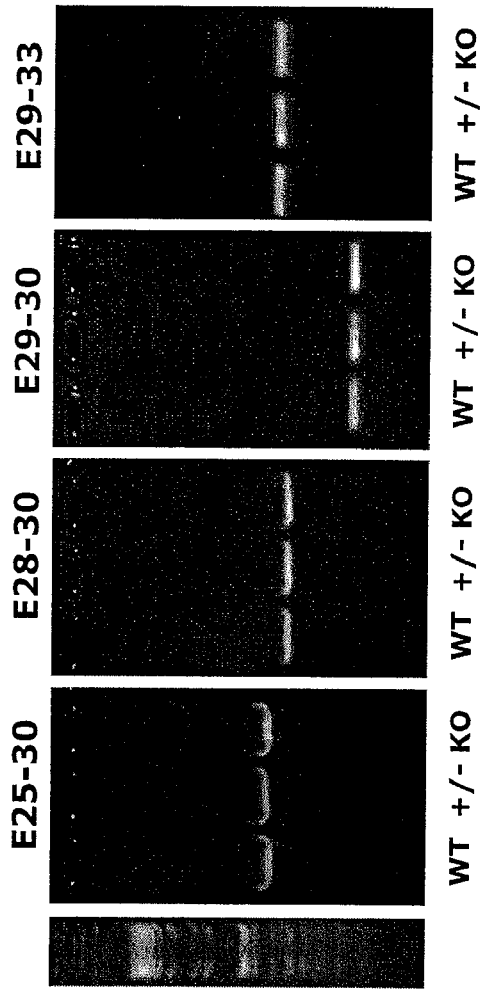
FIG. 6B
FIG. 6A

Microarray analysis

Cardiac troponin I, fast skeletal — 73.5 fold
Troponin T3, fast skeletal — 36.8 fold
MLC, fast skeletal — 11.3 fold
Alpha skeletal actin — 1.3 fold

FIG. 7

Target prediction:
MiRanda:      15 predicted possible target (THRAP number 8)
PicTar:       46 predicted possible target (THRAP number 1)

3'UTR THRAP1

```
                                                              3'   UGUUCGAAAAACG------AGCAGAAUA  5'  miR 208 (SEQ ID NO:5)
                                                                   :||  |   |   ||      ||||||||
Human    (SEQ ID NO:6)   UUCUUGCUUUAAAGCAAUUGGUCUAAAAUAUAUGUA----AUCGUCUUAAUUAAAAAGUUGCAGUAGGGUUGC
Chimp    (SEQ ID NO:7)   UUCUUGCUUUAAAGCAAUUGGUCUAAAAUAUAUGUA----AUCGUCUUAAUUAAACGUUGCAGUAGGGUUGC
Murine   (SEQ ID NO:8)   UUCUUGCUUUAAAGCAAUUGGUCUAAAAUAUAUGUA----AUCGUCUUAAUUAAAACGUUGCAGUAGGGUUGC
Rat      (SEQ ID NO:9)   UUCUUGCUUUAAAGCAAUUGGUCUAAAAUAUAUGUA----AUCGUCUUAAUUAAAACGUUGCAGUAGGGUUGC
Dog      (SEQ ID NO:10)  UUCUUGCUUUAAAGCAAUUGGUCUAAAAUAUAUGUA----AUCGUCUUAAUUAAAACGUUGCAGUAGGGUUGC
Chicken  (SEQ ID NO:11)  UUCUUGCUUUAAAGCAAUUGGUCUAAAAUAUAUGUA----AUCGUCUUAAUUAAACGUUGCAGUAGGGUUGC
Fugu     (SEQ ID NO:12)  UUCCUGCUUUAA-GCAAUUGGUUGAAAUAUAUAUGUAAUGUAUGUCUUAAUUAAAAAACAAACUAAGACAAA
Zebrafish(SEQ ID NO:13)  UUCCUGCUUUAAAGCAAUUGGUCUAAAAUAUAUGUA----AUCGUCUUCAUUACAAAAACGAACCAUCAAACG
                         ***  *********  ***************          ** ********           **
```

FIG. 18A-D miR-499 is located within Myosin Heavy Chain 7b

Myosin heavy chain 7b

```
Mouse       --TCCCTGTGTCTTGGGTGGGCAGCTGTTAAGACTTGCAGTGATGTTTAGCT--CCTCT-GCATGTGAACATCACAC
Rat         --TCCCTGT--CTTGGGTGGGCAGCTGTTAAGACTTGCAGTGATGTTTAGCT--CCTCT-CCATGTGAACATCACAC
Human       --CCCCTGTGCCTTGGGCGGCGGGCCGGCTGTTAAGACTTGCAGTGATGTTTAACT--CCTCT-CCACGTGAACATCACAC
Dog         --CCCTGCACCCTGGGCGGGCGGGCCGGCTGTTAAGACTTGCAGTGATGTTTAACT--CCTCT-CCACGTGAACATCACA
Opposum     --CCCCTGCCTCCCCGGCGGGCCAGCTGTTAAGACTTGCAGTGATGTTTAATT--CTTCT-CTATGTGAACATCACAA
Chicken     ========GGAGCGGCAGTGTTAAGACTTGTAGTGATGTTTAGAT-AATGTATTACATGAACATCACTT
X tropicalis --GTCTT--------AGCGAGGCAGTGTTAAGACTTGCAGTGATGTTTAGTTAAAATCT-TTTCATGAACATCACTTTAAC
```

Pre-miR 499

```
          gggu      u  ua       a        ---   uc
       gggcagc  gu     agacuugc gugauguuua   gc  c
       |||||||  ||     |||||||| ||||||||||   ||  |
       uccgucg  cg     ucugaacg cacuacaagu   cg  u
          ----      u  ug       a        gua   uc
``` miR 499

UUAAGACUUGCAGUGAUGUUU

FIG. 22

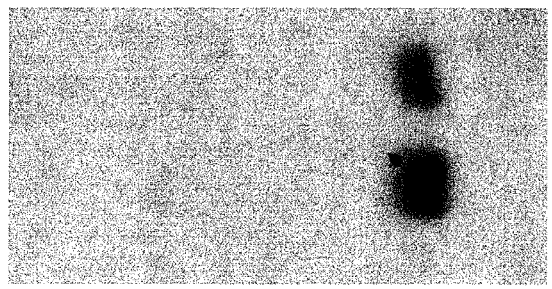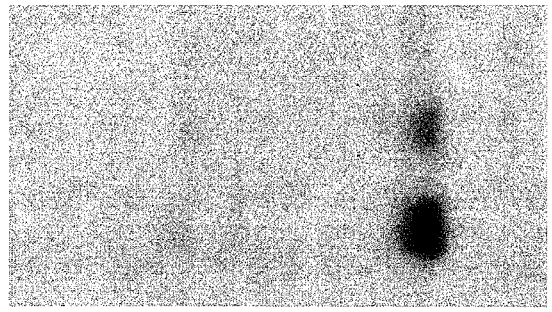
FIG. 24

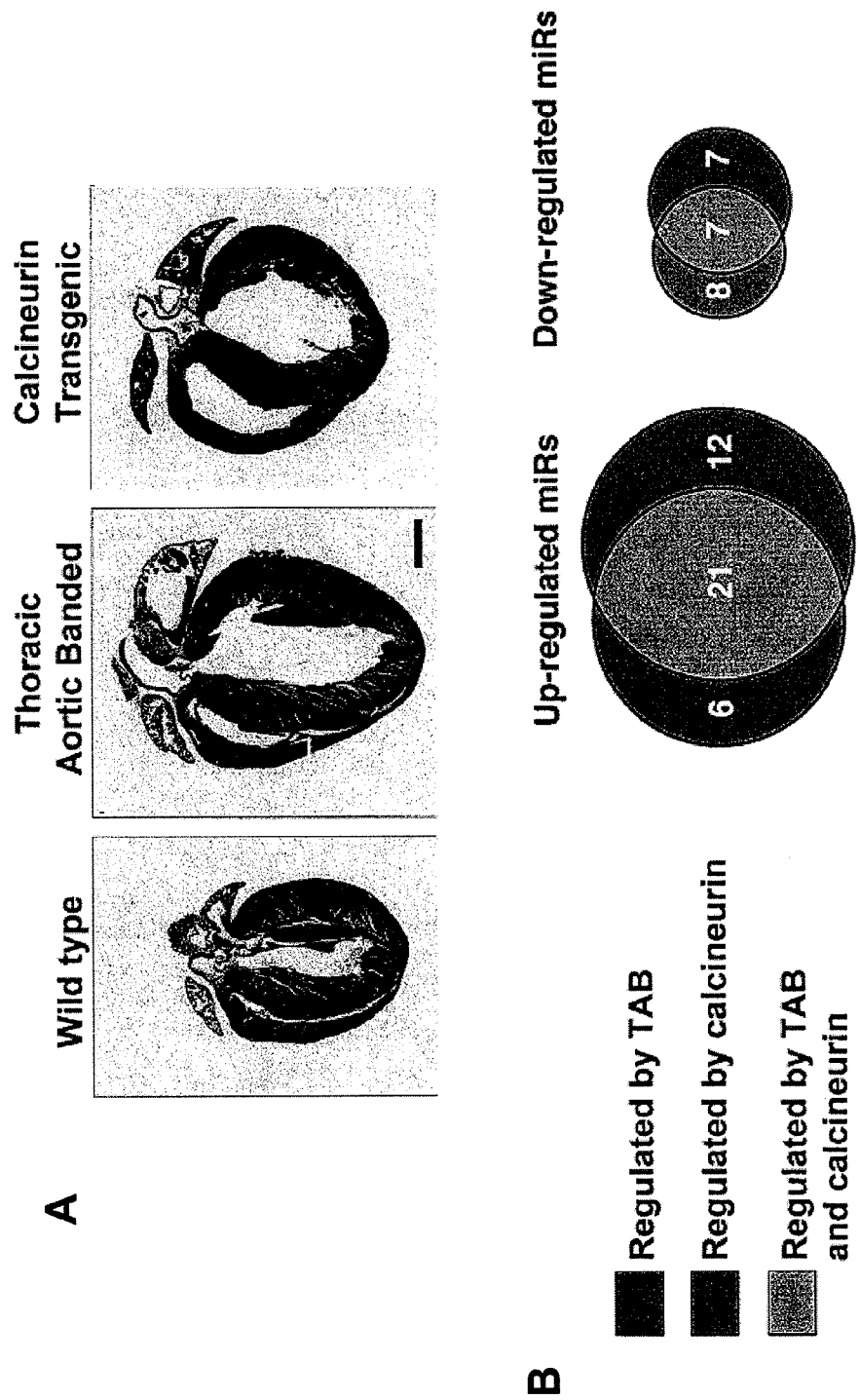
FIG. 26A-B

SEQUENCE LISTING

<160> NUMBER OF SEQ ID NOS: 34

<210> SEQ ID NO 1
<211> LENGTH: 89
<212> TYPE: DNA
<213> ORGANISM: Homo sapiens

<400> SEQUENCE: 1
ttacttcctt tgacgggcga gcttttggcc cgggttatac ctgatgctca cgtataagac    60
gagcaaaaag cttgttggtc agaggagct                                      89

<210> SEQ ID NO 2
<211> LENGTH: 89
<212> TYPE: DNA
<213> ORGANISM: Murine

<400> SEQUENCE: 2
ccacttcctg tgacgggtga gcttttggcc cgggttatac ctgactctca cgtataagac    60
gagcaaaaag cttgttggtc agaggagct                                      89

<210> SEQ ID NO 3
<211> LENGTH: 89
<212> TYPE: DNA
<213> ORGANISM: Rattus norvegicus

<400> SEQUENCE: 3
ttacttcctt tgacgggtga gcttttggcc cgggttatac ctgactctca cgtataagac    60
gagcaaaaag cttgttggtc agaggagct                                      89

<210> SEQ ID NO 4
<211> LENGTH: 89
<212> TYPE: DNA
<213> ORGANISM: Canis familiaris

<400> SEQUENCE: 4
tcacttcctg tgacgcatga gcttttggct cgggttatac ctgatgctca cgtataagac    60
gagcaaaaag cttgttggtc agaggagct                                      89

<210> SEQ ID NO 5
<211> LENGTH: 22
<212> TYPE: RNA
<213> ORGANISM: Homo sapiens

<400> SEQUENCE: 5
auaagacgag caaaaagcuu gu                                              22

<210> SEQ ID NO 6
<211> LENGTH: 69
<212> TYPE: RNA
<213> ORGANISM: Homo sapiens

<400> SEQUENCE: 6
uucuugcuuu aaagcaauug gucuaaaaua uauguaaucg ucuuaauuaa aaaguugcag    60
uagguuugc                                                            69

<210> SEQ ID NO 7
<211> LENGTH: 69
<212> TYPE: RNA
<213> ORGANISM: Pan troglodytes

<400> SEQUENCE: 7
uucuugcuuu aaagcaauug gucuaaaaua uauguaaucg ucuuaauuaa aacguugcag    60
uagguuugc                                                            69

<210> SEQ ID NO 8
<211> LENGTH: 69
<212> TYPE: RNA

-continued

<213> ORGANISM: Murine

<400> SEQUENCE: 8
uucuugcuuu aaagcaauug gucuaaaaua uauguaaucg ucuuaauuaa aacguugcag    60
uaggguugc                                                           69

<210> SEQ ID NO 9
<211> LENGTH: 69
<212> TYPE: RNA
<213> ORGANISM: Rattus norvegicus

<400> SEQUENCE: 9
uucuugcuuu aaagcaauug gucuaaaaua uauguaaucg ucuuaauuaa aacguugcag    60
uaggguugc                                                           69

<210> SEQ ID NO 10
<211> LENGTH: 69
<212> TYPE: RNA
<213> ORGANISM: Canis familiaris

<400> SEQUENCE: 10
uucuugcuuu aaagcaauug gucuaaaaua uauguaaucg ucuuaauuaa aacguugcag    60
uaggguugc                                                           69

<210> SEQ ID NO 11
<211> LENGTH: 69
<212> TYPE: RNA
<213> ORGANISM: Gallus gallus

<400> SEQUENCE: 11
uucuugcuuu aaagcaauug gucuaaaaua uauguaaucg ucuuaauuaa aacguugcag    60
uaggguugc                                                           69

<210> SEQ ID NO 12
<211> LENGTH: 72
<212> TYPE: RNA
<213> ORGANISM: Takifugu

<400> SEQUENCE: 12
uuccugcuuu aagcaauugg uugaaaauau auguauguaa uggucuuaau uaaaaaaaca    60
aacuaagaca aa                                                       72

<210> SEQ ID NO 13
<211> LENGTH: 69
<212> TYPE: RNA
<213> ORGANISM: Danio rerio

<400> SEQUENCE: 13
uuccugcuuu aaagcaauug gucuaaaaua uauguaaucg ucuucauuac aaaaacgaac    60
caucaaacg                                                           69

<210> SEQ ID NO 14
<211> LENGTH: 71
<212> TYPE: DNA
<213> ORGANISM: Homo sapiens

<400> SEQUENCE: 14
acgggcgagc ttttggcccg ggttatacct gatgctcacg tataagacga gcaaaaagct    60
tgttggtcag a                                                        71

```
<210> SEQ ID NO 15
<211> LENGTH: 71
<212> TYPE: DNA
<213> ORGANISM: Murine

<400> SEQUENCE: 15
acgggtgagc ttttggcccg ggttatacct gactctcacg tataagacga gcaaaaagct      60
tgttggtcag a                                                           71

<210> SEQ ID NO 16
<211> LENGTH: 71
<212> TYPE: DNA
<213> ORGANISM: Rattus norvegicus

<400> SEQUENCE: 16
acgggtgagc ttttggcccg ggttatacct gactctcacg tataagacga gcaaaaagct      60
tgttggtcag a                                                           71

<210> SEQ ID NO 17
<211> LENGTH: 71
<212> TYPE: DNA
<213> ORGANISM: Canis familiaris

<400> SEQUENCE: 17
acgcatgagc ttttggctcg ggttatacct gatgctcacg tataagacga gcaaaaagct      60
tgttggtcag a                                                           71

<210> SEQ ID NO 18
<211> LENGTH: 17
<212> TYPE: DNA
<213> ORGANISM: Artificial sequence
<220> FEATURE:
<223> OTHER INFORMATION: Description of Artificial Sequence: Synthetic
      Primer

<400> SEQUENCE: 18
gtgctcgctt cggcagc                                                     17

<210> SEQ ID NO 19
<211> LENGTH: 28
<212> TYPE: DNA
<213> ORGANISM: Artificial sequence
<220> FEATURE:
<223> OTHER INFORMATION: Description of Artificial Sequence: Synthetic
      Primer

<400> SEQUENCE: 19
aaaatatgga acgcttcacg aatttgcg                                         28

<210> SEQ ID NO 20
<211> LENGTH: 71
<212> TYPE: DNA
<213> ORGANISM: Mus sp.

<400> SEQUENCE: 20
tccctgtgtc ttgggtgggc agctgttaag acttgcagtg atgtttagct cctctgcatg      60
tgaacatcac a                                                           71

<210> SEQ ID NO 21
<211> LENGTH: 69
<212> TYPE: DNA
<213> ORGANISM: Rattus sp.

<400> SEQUENCE: 21
```

-continued

```
tccctgtctt gggtgggcag ctgttaagac ttgcagtgat gtttagctcc tctccatgtg    60
aacatcaca                                                           69

<210> SEQ ID NO 22
<211> LENGTH: 71
<212> TYPE: DNA
<213> ORGANISM: Homo sapiens

<400> SEQUENCE: 22
cccctgtgcc ttgggcgggc ggctgttaag acttgcagtg atgtttaact cctctccacg    60
tgaacatcac a                                                        71

<210> SEQ ID NO 23
<211> LENGTH: 71
<212> TYPE: DNA
<213> ORGANISM: Canis familiaris

<400> SEQUENCE: 23
cccttgcacc ctgggcgggc ggccgttaag acttgcagtg atgtttaact cctctccacg    60
tgaacatcac a                                                        71

<210> SEQ ID NO 24
<211> LENGTH: 72
<212> TYPE: DNA
<213> ORGANISM: Didelphimorphia sp.

<400> SEQUENCE: 24
cccctgcctc cccggcgggc agctgttaag acttgcagtg atgtttaatt cttctctatg    60
tgaacatcac aa                                                       72

<210> SEQ ID NO 25
<211> LENGTH: 58
<212> TYPE: DNA
<213> ORGANISM: Gallus gallus

<400> SEQUENCE: 25
ggagcggcag ttaagacttg tagtgatgtt tagataatgt attacatgaa catcactt      58

<210> SEQ ID NO 26
<211> LENGTH: 67
<212> TYPE: DNA
<213> ORGANISM: Xenopus tropicalis

<400> SEQUENCE: 26
gtcttagcga ggcagttaag acttgcagtg atgtttagtt aaaatctttt catgaacatc    60
actttaa                                                             67

<210> SEQ ID NO 27
<211> LENGTH: 79
<212> TYPE: RNA
<213> ORGANISM: Unknown
<220> FEATURE:
<223> OTHER INFORMATION: Pre-miR-499

<400> SEQUENCE: 27
gggugggcag cuguuaagac uugcagugau guuuagcucc ucugcaugug aacaucacag    60
caagucugug cugcugccu                                                79

<210> SEQ ID NO 28
<211> LENGTH: 21
<212> TYPE: RNA
```

```
<213> ORGANISM: Unknown
<220> FEATURE:
<223> OTHER INFORMATION: miR-499

<400> SEQUENCE: 28
uuaagacuug cagugauguu u                                              21

<210> SEQ ID NO 29
<211> LENGTH: 24
<212> TYPE: RNA
<213> ORGANISM: Unknown
<220> FEATURE:
<223> OTHER INFORMATION: miR-208 alternative sequence

<400> SEQUENCE: 29
auaagacgag caaaaagcuu guuu                                           24

<210> SEQ ID NO 30
<211> LENGTH: 23
<212> TYPE: RNA
<213> ORGANISM: Unknown
<220> FEATURE:
<223> OTHER INFORMATION: miR-499 alternative sequence

<400> SEQUENCE: 30
uuaagacuug cagugauguu uaa                                            23

<210> SEQ ID NO 31
<211> LENGTH: 23
<212> TYPE: RNA
<213> ORGANISM: Unknown
<220> FEATURE:
<223> OTHER INFORMATION: miR-29b-1

<400> SEQUENCE: 31
uagcaccauu ugaaaucagu guu                                            23

<210> SEQ ID NO 32
<211> LENGTH: 21
<212> TYPE: RNA
<213> ORGANISM: Unknown
<220> FEATURE:
<223> OTHER INFORMATION: miR-29a

<400> SEQUENCE: 32
uagcaccauc ugaaaucggu u                                              21

<210> SEQ ID NO 33
<211> LENGTH: 23
<212> TYPE: RNA
<213> ORGANISM: Unknown
<220> FEATURE:
<223> OTHER INFORMATION: miR-29b-2

<400> SEQUENCE: 33
uagcaccauu ugaaaucagu guu                                            23

<210> SEQ ID NO 34
<211> LENGTH: 20
<212> TYPE: RNA
<213> ORGANISM: Unknown
<220> FEATURE:
<223> OTHER INFORMATION: miR-29c

<400> SEQUENCE: 34
uagcaccauu ugaaaucggu                                                20
```

IDENTIFICATION OF A MICRO-RNA THAT ACTIVATES EXPRESSION OF β-MYOSIN HEAVY CHAIN

This application claims benefit of priority to U.S. Provisional Application Ser. No. 60/834,667, filed Aug. 1, 2006, the entire contents of which are hereby incorporated by reference.

This invention was made with grant support under grant no. HL53351-06 from the National Institutes of Health. The government has certain rights in the invention.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: MIRG 001_001_01US SubSeqList_ST25.txt, date recorded: Jun. 23, 2011, file size 8 kilobytes).

BACKGROUND OF THE INVENTION

1. Field of the Invention

The present invention relates generally to the fields of developmental biology and molecular biology. More particularly, it concerns gene regulation and cellular physiology in cardiomyocytes and skeletal muscle cells. Specifically, the invention relates to the inhibition of an miRNA that results in reduced expression of β-myosin heavy chain (β-MHC), thereby treating cardiac hypertrophy and heart failure. Also contemplated is up-regulation of this miRNA to treat musculoskeletal diseases.

2. Description of Related Art

Cardiac hypertrophy in response to an increased workload imposed on the heart is a fundamental adaptive mechanism. It is a specialized process reflecting a quantitative increase in cell size and mass (rather than cell number) as the result of any, or a combination of, neural, endocrine or mechanical stimuli. Hypertension, another factor involved in cardiac hypertrophy, is a frequent precursor of congestive heart failure. When heart failure occurs, the left ventricle usually is hypertrophied and dilated and indices of systolic function, such as ejection fraction, are reduced. Clearly, the cardiac hypertrophic response is a complex syndrome and the elucidation of the pathways leading to cardiac hypertrophy will be beneficial in the treatment of heart disease resulting from various stimuli.

Pathological myocardial hypertrophy is characterized by an increase in cardiomyocyte protein and the expression of a gene profile reminiscent of early embryonic development. Specifically, expression of β-myosin heavy chain (β-MHC), skeletal α-actin (sACT), and both atrial and brain natriuretic peptides (ANP and BNP, respectively) increases, whereas that of the adult cardiac muscle-specific genes, α-myosin heavy chain (α-MHC) and sarcoplasmic reticulum $Ca^{2+}$-ATPase (SERCA), decreases. In particular, there is compelling evidence indicating a role for changes in MHC isoform expression in the pathogenesis of heart failure in humans. Indeed, α-MHC mRNA and protein levels are markedly reduced in failing human hearts, and improvement of left-ventricular ejection fraction through beta-blocker therapy is associated with normalization of α-MHC expression. Additionally, a mutation in the human α-MHC gene was identified in association with hypertrophic cardiomyopathy, which demonstrates that, despite its low abundance, the level of α-MHC expression is critical for normal heart function. Thus, it is clear that both α- and β-MHC play a role in the development of cardiac hypertrophy, but the precise features by which these products act in creating and/or maintaining the pathologic state remain unknown.

SUMMARY OF THE INVENTION

Thus, in accordance with the present invention, there is provided in one embodiment a method of regulating cardiac contractility and remodeling comprising administering a modulator of miR-208 expression or activity to heart cells. In one embodiment, there is provided a method of regulating cardiac contractile protein gene expression comprising administering a modulator of miR-208 expression or activity to heart cells. The modulator may be an agonist or an antagonist of miR-208 expression or activity. In certain aspects of the invention, there is provided a method of reducing β-MHC expression in heart cells comprising administering an inhibitor of miR-208 expression or activity to the heart cells. In other aspects of the invention, there is provided a method of elevating β-MHC expression in heart cells comprising increasing endogenous miR-208 expression or activity or administering exogenous miR-208 to the heart cells. In one aspect of the invention, there is provided a method of increasing the expression of a fast skeletal muscle contractile protein gene in heart cells comprising administering to the heart cells an inhibitor of miR-208 expression or activity. In another aspect of the invention, there is provided a method of decreasing the expression of a fast skeletal muscle contractile protein gene in heart cells comprising increasing endogenous miR-208 expression or activity or administering exogenous miR-208 to the heart cells. Examples of fast skeletal muscle contractile protein genes that may be increased or decreased according to the methods of the present invention include: skeletal troponin I; troponin T3, myosin light chain, or α-skeletal actin.

In one embodiment, the present invention provides a method for treating pathologic cardiac hypertrophy or heart failure comprising: identifying a patient having cardiac hypertrophy, heart failure, or post myocardial infarction remodeling; and inhibiting expression or activity of miR-208 in heart cells of the patient. In another embodiment, there is provided a method of preventing pathologic hypertrophy or heart failure comprising: identifying a patient at risk of developing pathologic cardiac hypertrophy or heart failure; and inhibiting expression or activity of miR-208 in heart cells of the patient.

In one embodiment, the present invention provides a method of treating myocardial infarct comprising inhibiting expression or activity of miR-208 in heart cells of said subject. In another embodiment, the present invention provides a method of preventing cardiac hypertrophy and dilated cardiomyopathy comprising inhibiting expression or activity of miR-208 in heart cells of a subject. In yet a further embodiment, the present invention provides a method of inhibiting progression of cardiac hypertrophy comprising inhibiting expression or activity of miR-208 in heart cells of a subject. In certain embodiments, the present invention provides a method of increasing exercise tolerance, reducing hospitalization, improving quality of life, decreasing morbidity, and/or decreasing mortality in a subject with heart failure or cardiac hypertrophy comprising inhibiting expression or activity of miR-208 in heart cells of the subject. In other aspects of the invention, there is provided a method of increasing α-MHC expression in heart cells by administering an inhibitor of miR-208 under pathological conditions.

In certain aspects of the invention, inhibiting the expression or activity of miR-208 comprises administering an antagomir of miR-208. In one embodiment, the present invention provides an miR-208 antagomir. The administering of the antagomir or other modulator of miR-208 expression or activity may be by any method known to those in the art suitable for delivery to the targeted organ, tissue, or cell type. For example, in certain aspects of the invention, the modulator of miR-208 may be administered by intravenous injection, intraarterial injection, intrapericardial injection, or direct injection into the tissue (e.g., cardiac tissue, skeletal muscle tissue). In some aspects, administering comprises oral, transdermal, intraperitoneal, subcutaneous, sustained release, controlled release, delayed release, suppository, or sublingual administration of miR-208.

In certain aspects of the invention, the treating or preventing pathologic cardiac hypertrophy or heart failure in a patient further comprising administering to the patient a second cardiac hypertrophic therapy. The second therapy may be, for example, a beta blocker, an ionotrope, a diuretic, ACE-I, AII antagonist, BNP, a $Ca^{++}$-blocker, and ERA, or an HDAC inhibitor. The said second therapy may be administered before, at the same time, or after the inhibition of miR-208.

The treatment of pathologic cardiac hypertrophy or heart failure may be defined as improving one or more symptoms of pathologic cardiac hypertrophy or heart failure. The improved symptoms may be, for example, increased exercise capacity, increased cardiac ejection volume, decreased left ventricular end diastolic pressure, decreased pulmonary capillary wedge pressure, increased cardiac output, or cardiac index, lowered pulmonary artery pressures, decreased left ventricular end systolic and diastolic dimensions, decreased left and right ventricular wall stress, decreased wall tension, increased quality of life, and decreased disease related morbidity or mortality. The treatment of pathologic cardiac hypertrophy may also be defined as delaying the transition from cardiac hypertrophy to heart failure.

In certain embodiments of the present invention, there are provided methods of preventing pathologic hypertrophy or heart failure in a patient at risk of developing pathologic cardiac hypertrophy or heart failure. The patient at risk of developing pathologic cardiac hypertrophy or heart failure may exhibit one or more risk factors including, for example, long standing uncontrolled hypertension, uncorrected valvular disease, chronic angina, recent myocardial infarction, congenital predisposition to heart disease or pathological hypertrophy. In certain aspects, the patient at risk may be diagnosed as having a genetic predisposition to cardiac hypertrophy. In some aspects of the invention, the patient at risk may have a familial history of cardiac hypertrophy.

In one embodiment, the present invention provides a method of decreasing the expression or activity of a fast skeletal muscle contractile protein gene in skeletal muscle cells comprising administering miR-208 to the skeletal muscle cells. In one embodiment, the present invention provides a method of treating or preventing a musculoskeletal disorder in a subject comprising: identifying a patient having or at risk of a musculoskeletal disorder; and increasing the expression and/or activity of miR-208 in skeletal muscle cells of said patient. The musculoskeletal disorder may be, for example, disuse atrophy, muscle wasting in response to microgravity, or denervation. In certain aspects of the invention, the method of treating or preventing the musculoskeletal disorder further comprises administering a second non-miR-208 therapy.

Increasing the expression and/or activity of miR-208 may comprise administering miR-208 to the subject or administering an expression vector that expresses miR-208 to the subject. The expression vector is a viral expression vector. The viral expression vector may be, for example, an adenoviral or retroviral expression vector. In certain aspects, the expression vector is a non-viral expression vector. In certain aspects of the invention, miR-208 or an expression vector encoding miR-208 is associated with a lipid vehicle. Alternatively, one may simply provide miR-208 by itself, optionally included within a delivery vehicle, such as a liposome or nanoparticle. The fact that miR 208 is cardiac specific will prevent unwanted side-effects in other organs.

In one embodiment, the present invention provides a method for identifying a modulator of miR-208 comprising: (a) contacting a cell with a candidate compound; assessing miR-208 activity or expression; and (b) comparing the activity or expression in step (b) with the activity or expression in the absence of the candidate compound, wherein a difference between the measured activities or expression indicates that the candidate compound is a modulator of miR-208. In certain aspects of the invention, the cell is contacted with the candidate compound in vitro. In other aspects of the invention the cell is contacted with the candidate compound in vivo. The modualtor of miR-208 may be an agonist or antagonist of miR-208. Non-limiting examples of candidate compounds that may be screened according to the methods of the present invention are peptides, polypeptides, polynucleotides, or small molecules.

Assessing the miR-208 activity or expression may comprise assessing the expression level of miR-208. Those in the art will be familiar with a variety of methods for assessing RNA expression levels including, for example, northern blotting or RT-PCR. Assessing the miR-208 activity or expression may comprise assessing the activity of miR-208. In some embodiments, assessing the activity of miR-208 comprises assessing expression or activity of gene regulated by miR-208. Genes regulated by miR-208 include, for example, α and β-myosin heavy chain and fast skeletal muscle protein genes, such as fast skeletal troponin I, troponin T3, myosin light chain, and alpha skeletal actin. In certain aspects of the invention, assessing the activity of miR-208 comprises assessing the ratio of α-myosin heavy chain expression level to β-myosin heavy chain expression level. Those in the art will be familiar with a variety of methods for assessing the activity or expression of genes regulated by miR-208. Such methods include, for example, northern blotting, RT-PCR, ELISA, or western blotting.

In one embodiment, the present invention provides a modulator of miR-208 identified by a method comprising: (a) contacting a cell with a candidate compound; assessing miR-208 activity or expression; and (b) comparing the activity or expression in step (b) with the activity or expression in the absence of the candidate compound, wherein a difference between the measured activities or expression indicates that the candidate compound is a modulator of miR-208. Modulators of miR-208 may be included in pharmaceutical compositions for the treatment of cardiac disorders and/or musculoskeletal disorders according to the methods of the present invention.

In another embodiment, the present invention provides an inhibitor of miR-208 identified by a method comprising: (a) contacting a cell with a candidate compound; (b) assessing miR-208 activity or expression; and (c) comparing the activity or expression in step (b) with the activity or expression in the absence of the candidate compound, wherein a reduction in the activity or expression in the cell contacted with the candidate compound compared to the activity or expression in the cell in the absence of the candidate compound indicates that the candidate compound is an inhibitor of miR-208.

In one embodiment, the present invention provides a method for treating pathologic cardiac hypertrophy or heart failure comprising: identifying a patient having cardiac hypertrophy or heart failure; and administering an miR-208 inhibitor to the patient. In certain aspects of the invention the miR-208 inhibitor may be identified by a method comprising: (a) contacting a cell with a candidate compound; (b) assessing miR-208 activity or expression; and (c) comparing the activity or expression in step (b) with the activity or expression in the absence of the candidate compound, wherein a reduction in the activity or expression of miR-208 in the cell contacted with the candidate compound compared to the activity or expression in the cell in the absence of the candidate compound indicates that the candidate compound is an inhibitor of miR-208.

In another embodiment, the present invention provides a method for treating musculoskeletal disorder comprising: identifying a patient having a musculoskeletal disorder or at risk for developing a musculoskeletal disorder; and administering an miR-208 agonist to the patient. In certain aspects of the invention the miR-208 agonist may be identified by a method comprising: (a) contacting a cell with a candidate compound; (b) assessing miR-208 activity or expression; and (c) comparing the activity or expression in step (b) with the activity or expression in the absence of the candidate compound, wherein an increase in the activity or expression of miR-208 in the cell contacted with the candidate compound compared to the activity or expression in the cell in the absence of the candidate compound indicates that the candidate compound is an agonist of miR-208.

In one embodiment, the present invention provides a transgenic, non-human mammal, the cells of which fail to express a functional miR-208. In another embodiment, the present invention provides a transgenic, non-human mammal, the cells of which comprise a miR-208 coding region under the control of a heterologous promoter active in the cells of said non-human mammal. The transgenic mammal may be, for example, a mouse or a rat. The promoter may be a tissue specific promoter such as, for example, a skeletal muscle specific promoter or a cardiac muscle specific promoter. In certain embodiments, the present invention provides a transgenic, non-human mammalian cell lacking one or both native miR-208 alleles.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the invention, and vice versa. Furthermore, compositions and kits of the invention can be used to achieve methods of the invention.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 3A) Diagram for PTU/T3 regulation of α- and βMHC. (FIG. 3B) Rats were treated with PTU for one week in the presence and absence of T3 and αMHC and βMHC mRNAs were detected by real-time PCR. (FIG. 3C) Rats were treated with PTU or PTU+T3, as indicated, for a week, and the expression of miR-208 was detected by Northern blot. Hearts from four animals under each condition were analyzed.

FIGS. 4A-C—Inhibition of α-MHC expression leads to decreased levels of miR-208. (FIGS. 4A-B) Relative expression levels fo α- and βMHC transcripts at 0, 3, 6, 9, 12, 15, 18 and 21 days. (FIG. 4C) Northern blot analysis of miR-208 in cardiac rat tissue at the indicated time points during PTU treatment.

(FIG. 5A) Strategy to generate miR-208 mutant mice by homologous recombination. The pre-miRNA sequence was replaced with a neomycin resistance cassette (Neo) flanked by loxP sites. The neomycin cassette was removed in the mouse germ line by breeding heterozygous mice to transgenic mice harboring the CAG-Cre transgene. DTA, diphtheria toxin A. (FIG. 5B) Detection of miR-208 transcripts by Northern analysis of hearts from wild-type (WT) and miR-208 mutant (KO) mice.

FIGS. 6A-B—miR-208 deletion does not alter α-MHC expression. (FIG. 6A) Analysis of αMHC transcripts by RT-PCR from RNA of hearts of mice of the indicated genotypes. Positions of primer relative to αMHC exons are shown and primer pairs are above each set of samples. (FIG. 6B) Western analysis of aMHC and bMHC protein levels in hearts of neonatal mice of the indicated genotypes. Two mice of each genotype were analyzed. Glyceraldehyde-3-phosphate dehydrogenase (GAPDH) was detected as a loading control.

FIG. 7—Upregulation of fast skeletal genes in miR-208 knock-out.

FIG. 11—THRAP1 as a predicted target of miR-208. Sequence alignment of putative miR-208 binding site in 3' UTR of THRAP1 shows a high level of complementarity and sequence conservation.

FIG. 12—3' UTR THRAP1 luciferase assay.

(FIG. 14A) αMHC mRNA expression was detected by realtime PCR in wild-type and miR-208$^{-/-}$ mice following sham operation or TAB for 21 days. (FIG. 14B) MiR-208 was detected by Northern blot of heart tissue from wild-type and miR-208$^{-/-}$ mice. (FIG. 14C) Echocardiographic analysis indicated a decrease in FS due to an increase in LV in systole (LVIDs) dilation in both miR-208$^{-/-}$ and wild-type littermates in response to TAB. Anterior and posterior wall (AW and PW) thickness in either systole (s) or diastole (d) after TAB indicate a blunted hypertrophic response in miR-208$^{-/-}$ animals compared to wild-type animals (n=5-7 per group). *p<0.05 compared to corresponding wild-type group. (FIG. 14D) Detection of miR-208 transcripts by Northern analysis of hearts from wild-type and miR-208 transgenic mice. (FIG. 14E) Transcripts for αMHC, βMHC, ANF and BNP were detected by real-time PCR in hearts from the indicated genotype. Values are expressed as fold-increase in expression (±SEM) compared to wild-type mice (n=3).

(FIG. 15A) Histological sections of hearts of wild-type and miR-208$^{-/-}$ mice stained for Masson trichrome. The absence of miR-208 diminishes hypertrophy and fibrosis seen in wild-type mice subjected to TAB for 21 days. Scale bar equals 2 mm in top panel and 20 μm for bottom panel. (FIG. 15B) Transcripts for βMHC, ANF and BNP were detected by real-time PCR in hearts from wild-type and miR-208$^{-/-}$ mice following sham or TAB surgery. Values are expressed as fold-increase in expression (±SEM) compared to sham operated wild-type mice (n=3). (FIG. 15C) Western analysis of αMHC and βMHC protein levels in adult wild-type and miR-208 mutant mice 21 days after sham and TAB. (FIG. 15D) Histological sections of hearts of 6 week-old mice expressing a calcineurin transgene (CnA-Tg) and hearts of miR-208$^{-/-}$; CnA-Tg stained for Masson trichrome. The absence of miR-208 diminishes hypertrophy and fibrosis seen in CnA-Tg mice. Scale bar equals 2 mm in top panel and 20 μm for bottom panel. (FIG. 15E) Transcripts for βMHC, ANF and BNP were detected by real-time PCR in hearts from the indicated genotype. Values are expressed as fold-increase in expression (±SEM) compared to wild-type mice (n=3). (FIG. 15F) Western analysis of αMHC and βMHC protein levels in adult wild-type and miR-208 mutant mice with and without the presence of the CnA transgene. (FIG. 15G) Western analysis of αMHC and βMHC protein levels in adult wild-type and miR-208 transgenic animals.

(FIG. 16A) MiR-208 was detected by Northern blot of heart tissue from wild type and miR-208$^{-/-}$ mice after PTU treatment. (FIG. 16B) Echocardiography showed a comparable decrease in heart rate (HR) and fractional shortening (FS) in wild-type and miR-208$^{-/-}$ mice in response to PTU, due to increase in LV dilation (LVID) in both diastole (d) and systole (s) and thinning of the anterior and posterior LV wall (AW, PW) (n=6). *p<0.05 compared to corresponding wild-type group. (FIG. 16C) Transcripts for ANF and BNP were detected by real-time PCR in hearts from wild-type and miR-208$^{-/-}$ mice following PTU treatment. Values are expressed as-fold increase in expression (±SEM) compared to wild-type mice that received regular chow (n=3).

(FIG. 17A) Western analysis of αMHC and βMHC expression in wild-type, and miR-208 mutant mice at baseline and 2 weeks after PTU treatment. (FIG. 17B) Transcripts for αMHC and βMHC were detected by real-time PCR in hearts from wild-type and miR-208$^{-/-}$ mice following PTU treatment. Values are expressed as fold-increase in expression (±SEM) compared to wild-type mice that received regular chow (n=3).

FIGS. 18A-D—MiR-208 targets THRAP1. (FIG. 18A) Sequence alignment of putative miR-208 binding site in 3' UTR of THRAP1 shows a high level of complementarity and sequence conservation. (FIG. 18B) COS1 cells were transfected with a THRAP1 3' UTR luciferase construct, along with expression plasmids for miR-126 and miR-208. Values are as fold-change in luciferase expression (±SD) compared to the reporter alone. (FIG. 18D) THRAP1 Western blot using a THRAP1 specific antibody on THRAP1-immunoprecipitated cardiac cell lysates using 400 μg of protein from either wild-type or miR-208$^{-/-}$ animals.

FIG. 22—Structure of the Myh7b locus and the position of the miR-499 coding region (SEQ ID NOS. 20-26) within it. SEQ ID NOS. 7 and 28 represent miR-499 pre-miRNA and mature sequences.

FIG. 24—Northern blot showing expression of miR-499 in wild-type mice with heart disease. MI, myocardial infarction. CnA Tg, calcineurin transgenic mice.

FIGS. 26A-C—mRNA expression during cardiac hypertrophy. (FIG. 26A) H&E stained sections of representative hearts from mice following sham and TAB for 21 days and from CnA Tg mice. Scale bar equals 2 mm. (FIG. 26B) Venn diagrams showing numbers of microRNAs that changed in expression in each type of heart are shown below. (FIG. 26C) Northern blots of microRNAs that change in expression during hypertrophy. U6 RNA was detected as a loading control.

DETAILED DESCRIPTION OF ILLUSTRATIVE EMBODIMENTS

Figure 1:
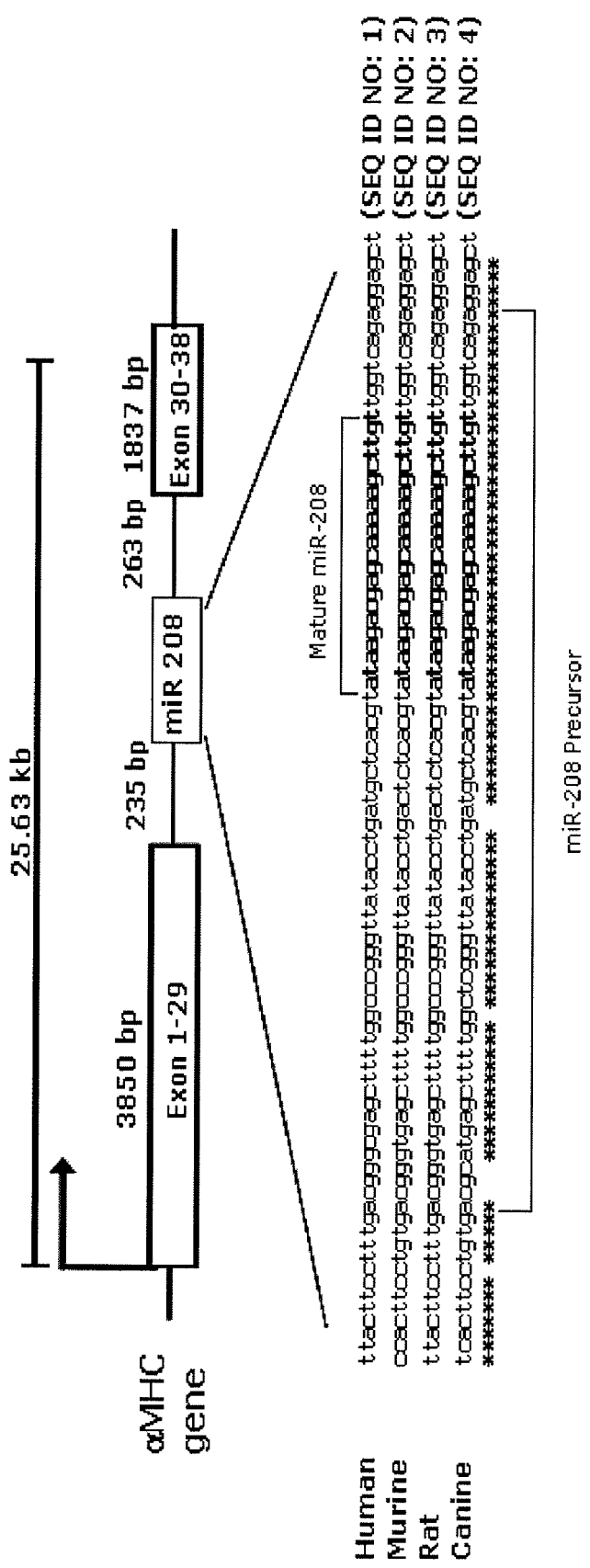
FIG. 1—miR-208 is contained in the cardiac α-MHC gene. miR-208 is encoded by intron 27 of the αMHC gene. Asterisks indicate sequence conservation.

Heart failure is one of the leading causes of morbidity and mortality in the world. In the U.S. alone, estimates indicate that 3 million people are currently living with cardiomyopathy and another 400,000 are diagnosed on a yearly basis. Dilated cardiomyopathy (DCM), also referred to as "congestive cardiomyopathy," is the most common form of the cardiomyopathies and has an estimated prevalence of nearly 40 per 100,000 individuals (Durand et al., 1995). Although there are other causes of DCM, familiar dilated cardiomyopathy has been indicated as representing approximately 20% of "idiopathic" DCM. Approximately half of the DCM cases are idiopathic, with the remainder being associated with known disease processes. For example, serious myocardial damage can result from certain drugs used in cancer chemotherapy (e.g., doxorubicin and daunoribucin). In addition, many DCM patients are chronic alcoholics. Fortunately, for these patients, the progression of myocardial dysfunction may be stopped or reversed if alcohol consumption is reduced or stopped early in the course of disease. Peripartum cardiomyopathy is another idiopathic form of DCM, as is disease associated with infectious sequelae. In sum, cardiomyopathies, including DCM, are significant public health problems.

Heart disease and its manifestations, including coronary artery disease, myocardial infarction, congestive heart failure and cardiac hypertrophy, clearly presents a major health risk in the United States today. The cost to diagnose, treat and support patients suffering from these diseases is well into the billions of dollars. Two particularly severe manifestations of heart disease are myocardial infarction and cardiac hypertrophy. With respect to myocardial infarction, typically an acute thrombocytic coronary occlusion occurs in a coronary artery as a result of atherosclerosis and causes myocardial cell death. Because cardiomyocytes, the heart muscle cells, are terminally differentiated and generally incapable of cell division, they are generally replaced by scar tissue when they die during the course of an acute myocardial infarction. Scar tissue is not contractile, fails to contribute to cardiac function, and often plays a detrimental role in heart function by expanding during cardiac contraction, or by increasing the size and effective radius of the ventricle, for example, becoming hypertrophic. With respect to cardiac hypertrophy, one theory regards this as a disease that resembles aberrant development and, as such, raises the question of whether developmental signals in the heart can contribute to hypertrophic disease. Cardiac hypertrophy is an adaptive response of the heart to virtually all forms of cardiac disease, including those arising from hypertension, mechanical load, myocardial infarction, cardiac arrhythmias, endocrine disorders, and genetic mutations in cardiac contractile protein genes. While the hypertrophic response is initially a compensatory mechanism that augments cardiac output, sustained hypertrophy can lead to DCM, heart failure, and sudden death. In the United States, approximately half a million individuals are diagnosed with heart failure each year, with a mortality rate approaching 50%.

The causes and effects of cardiac hypertrophy have been extensively documented, but the underlying molecular mechanisms have not been elucidated. Understanding these mechanisms is a major concern in the prevention and treatment of cardiac disease and will be crucial as a therapeutic modality in designing new drugs that specifically target cardiac hypertrophy and cardiac heart failure. As pathologic cardiac hypertrophy typically does not produce any symptoms until the cardiac damage is severe enough to produce heart failure, the symptoms of cardiomyopathy are those associated with heart failure. These symptoms include shortness of breath, fatigue with exertion, the inability to lie flat without becoming short of breath (orthopnea), paroxysmal nocturnal dyspnea, enlarged cardiac dimensions, and/or swelling in the lower legs. Patients also often present with increased blood pressure, extra heart sounds, cardiac murmurs, pulmonary and systemic emboli, chest pain, pulmonary congestion, and palpitations. In addition, DCM causes decreased ejection fractions (i.e., a measure of both intrinsic systolic function and remodeling). The disease is further characterized by ventricular dilation and grossly impaired systolic function due to diminished myocardial contractility, which results in dilated heart failure in many patients. Affected hearts also undergo cell/chamber remodeling as a result of the myocyte/myocardial dysfunction, which contributes to the "DCM phenotype." As the disease progresses so do the symptoms. Patients with DCM also have a greatly increased incidence of life-threatening arrhythmias, including ventricular tachycardia and ventricular fibrillation. In these patients, an episode of syncope (dizziness) is regarded as a harbinger of sudden death.

Diagnosis of dilated cardiomyopathy typically depends upon the demonstration of enlarged heart chambers, particularly enlarged ventricles. Enlargement is commonly observable on chest X-rays, but is more accurately assessed using echocardiograms. DCM is often difficult to distinguish from acute myocarditis, valvular heart disease, coronary artery disease, and hypertensive heart disease. Once the diagnosis of dilated cardiomyopathy is made, every effort is made to identify and treat potentially reversible causes and prevent further heart damage. For example, coronary artery disease and valvular heart disease must be ruled out. Anemia, abnormal tachycardias, nutritional deficiencies, alcoholism, thyroid disease and/or other problems need to be addressed and controlled.

As mentioned above, treatment with pharmacological agents still represents the primary mechanism for reducing or eliminating the manifestations of heart failure. Diuretics constitute the first line of treatment for mild-to-moderate heart failure. Unfortunately, many of the commonly used diuretics (e.g., the thiazides) have numerous adverse effects. For example, certain diuretics may increase serum cholesterol and triglycerides. Moreover, diuretics are generally ineffective for patients suffering from severe heart failure.

If diuretics are ineffective, vasodilatory agents may be used; the angiotensin converting (ACE) inhibitors (e.g., enalopril and lisinopril) not only provide symptomatic relief, they also have been reported to decrease mortality (Young et al., 1989). Again, however, the ACE inhibitors are associated with adverse effects that result in their being contraindicated in patients with certain disease states (e.g., renal artery stenosis). Similarly, inotropic agent therapy (i.e., a drug that improves cardiac output by increasing the force of myocardial muscle contraction) is associated with a panoply of adverse reactions, including gastrointestinal problems and central nervous system dysfunction.

Thus, the currently used pharmacological agents have severe shortcomings in particular patient populations. The availability of new, safe and effective agents would undoubtedly benefit patients who either cannot use the pharmacological modalities presently available, or who do not receive adequate relief from those modalities. The prognosis for patients with DCM is variable, and depends upon the degree of ventricular dysfunction, with the majority of deaths occurring within five years of diagnosis.

I. THE PRESENT INVENTION

The ratio of α- to β-MHC isoforms in the adult heart is a major determinant of cardiac contractility. β-MHC, the major myosin isoform in the adult heart, displays relatively low ATPase activity, whereas α-MHC has high ATPase activity. In response to a variety of pathological stimuli such as myocardial infarction, hypertension, and other disorders, the β-MHC expression increases and α-MHC expression decreases with consequent reduction in myofibrillar ATPase activity and reduced shortening velocity of cardiac myofibers, leading to eventual contractile dysfunction. Remarkably, minor changes in α-MHC content of the heart can have a profound influence on cardiac performance.

MicroRNAs (miR5) are small ~22-nucleotide RNAs that are derived from larger pre-miRs. MiRs act as repressors of target mRNAs by promoting their degradation, when their sequences are perfectly complementary, or inhibiting translation when their sequences contain mismatches. microRNA-208 (miR-208) is encoded by an intron of the α-MHC gene and is expressed specifically in the heart. The inventors created miR-208 knockout mice and discovered that miR-208 is required for activation of β-MHC gene expression in the adult heart, as well as for expression of several other contractile protein genes. In addition, miR-208 inhibition leads to a severe reduction in cardiac fibrosis. These findings suggest that strategies to modulate the expression of miR-208 will have profound effects on cardiac contractility in humans, for example, inhibition of miR-208 to prevent β-MHC expression and maintain α-MHC expression in the heart following cardiac injury.

Another aspect of the invention is agonism of miR-208 expression or activity, either by therapeutically activating the endogenous miR-208 gene or introducing exogenous miR-208 into the heart using adenoviral vectors or other—again no need for using an adenoviral system means of ectopic expression to elevate β-MHC expression, for treatment of individuals with a mutation in the α-MHC gene. The up-regulation of several fast skeletal muscle contractile protein genes in the hearts of miR-208 mutant mice also suggests that miR-208 typically represses the fast skeletal muscle gene program. Activation of these genes in the heart represents a potential approach to regulate cardiac contractility.

In addition, the inventors propose use of miR-208 to repress fast fiber genes in skeletal muscle and thereby activate the reciprocal expression of slow fiber genes, which are coupled to enhanced insulin sensitivity and skeletal muscle endurance. Repression of slow fiber genes and activation of fast fiber genes in skeletal muscle is associated with numerous musculoskeletal disorders including disuse atrophy, muscle wasting in response to anti-gravity, and denervation.

Thus, the present inventors have discovered that miR-208 is a muscle-specific and essential regulator of β-MHC gene expression in the heart that in addition regulates cardiac fibrosis. The discovery that miR-208 regulates β-MHC expression and expression of fast skeletal muscle genes is completely novel as is the use of this microRNA to control cardiac contractility and skeletal muscle function.

II. miRNAs

A. Background

In 2001, several groups used a novel cloning method to isolate and identify a large group of "microRNAs" (miRNAs) from *C. elegans, Drosophila*, and humans (Lagos-Quintana et al., 2001; Lau et al., 2001; Lee and Ambros, 2001). Several hundreds of miRNAs have been identified in plants and animals—including humans—which do not appear to have endogenous siRNAs. Thus, while similar to siRNAs, miRNAs are nonetheless distinct.

miRNAs thus far observed have been approximately 21-22 nucleotides in length and they arise from longer precursors, which are transcribed from non-protein-encoding genes. See review of Carrington et al. (2003). The precursors form structures that fold back on each other in self-complementary regions; they are then processed by the nuclease Dicer in animals or DCL1 in plants. miRNA molecules interrupt translation through precise or imprecise base-pairing with their targets.

miRNAs are involved in gene regulation. Some miRNAs, including lin-4 and let-7, inhibit protein synthesis by binding to partially complementary 3' untranslated regions (3' UTRs) of target mRNAs. Others, including the Scarecrow miRNA found in plants, function like siRNA and bind to perfectly complementary mRNA sequences to destroy the target transcript (Grishok et al., 2001).

Research on microRNAs is increasing as scientists are beginning to appreciate the broad role that these molecules play in the regulation of eukaryotic gene expression. The two best understood miRNAs, lin-4 and let-7, regulate developmental timing in *C. elegans* by regulating the translation of a family of key mRNAs (reviewed in Pasquinelli, 2002). Several hundred miRNAs have been identified in *C. elegans, Drosophila*, mouse, and humans. As would be expected for molecules that regulate gene expression, miRNA levels have been shown to vary between tissues and developmental states. In addition, one study shows a strong correlation between reduced expression of two miRNAs and chronic lymphocytic leukemia, providing a possible link between miRNAs and cancer (Calin, 2002). Although the field is still young, there is speculation that miRNAs could be as important as transcription factors in regulating gene expression in higher eukaryotes.

There are a few examples of miRNAs that play critical roles in cell differentiation, early development, and cellular processes like apoptosis and fat metabolism. lin-4 and let-7 both regulate passage from one larval state to another during *C. elegans* development (Ambros, 2003). mir-14 and bantam are *drosophila* miRNAs that regulate cell death, apparently by regulating the expression of genes involved in apoptosis (Brennecke et al., 2003, Xu et al., 2003). MiR14 has also been implicated in fat metabolism (Xu et al., 2003). Lsy-6 and miR-273 are *C. elegans* miRNAs that regulate asymmetry in chemosensory neurons (Chang et al., 2004). Another animal miRNA that regulates cell differentiation is miR-181, which guides hematopoietic cell differentiation (Chen et al., 2004). These molecules represent the full range of animal miRNAs with known functions. Enhanced understanding of the functions of miRNAs will undoubtedly reveal regulatory networks that contribute to normal development, differentiation, inter- and intra-cellular communication, cell cycle, angiogenesis, apoptosis, and many other cellular processes. Given their important roles in many biological functions, it is likely that miRNAs will offer important points for therapeutic intervention or diagnostic analysis.

Characterizing the functions of biomolecules like miRNAs often involves introducing the molecules into cells or removing the molecules from cells and measuring the result. If introducing a miRNA into cells results in apoptosis, then the miRNA undoubtedly participates in an apoptotic pathway. Methods for introducing and removing miRNAs from cells have been described. Two recent publications describe antisense molecules that can be used to inhibit the activity of specific miRNAs (Meister et al., 2004; Hutvagner et al., 2004). Another publication describes the use of plasmids that are transcribed by endogenous RNA polymerases and yield specific miRNAs when transfected into cells (Zeng et al., 2002). These two reagent sets have been used to evaluate single miRNAs.

B. miR-208

Figure 2:
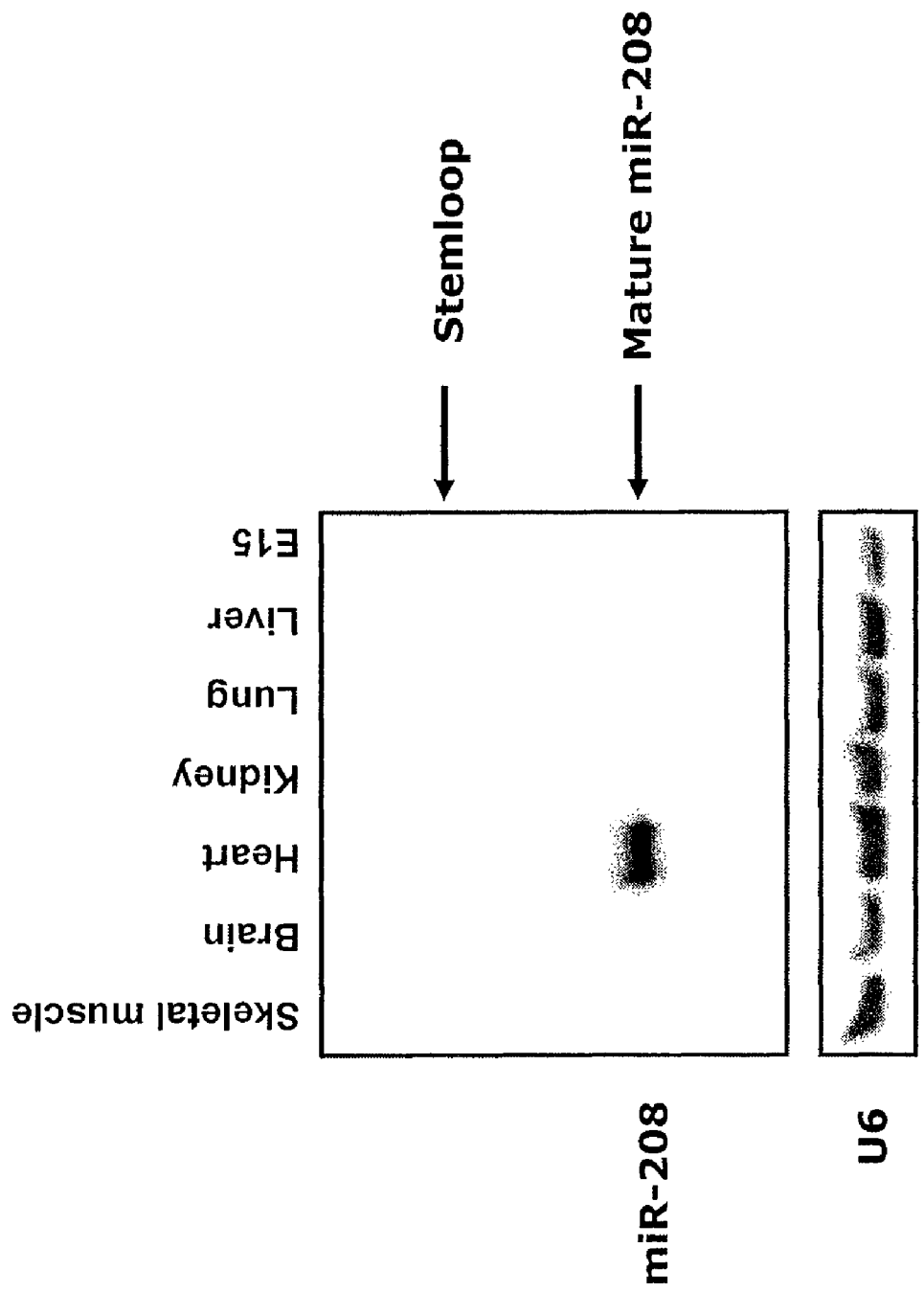
FIG. 2—miR-208 has the same expression pattern as α-MHC. Detection of miR-208 transcripts by Northern analysis of adult mouse tissues. U6 mRNA serves as a loading control.
Figure 3B:
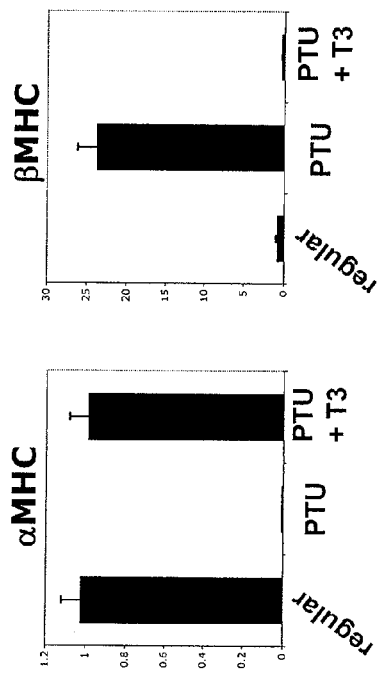
FIGS. 3A-C—Regulation of miR-208 expression by thyroid hormone.
Figure 3A:
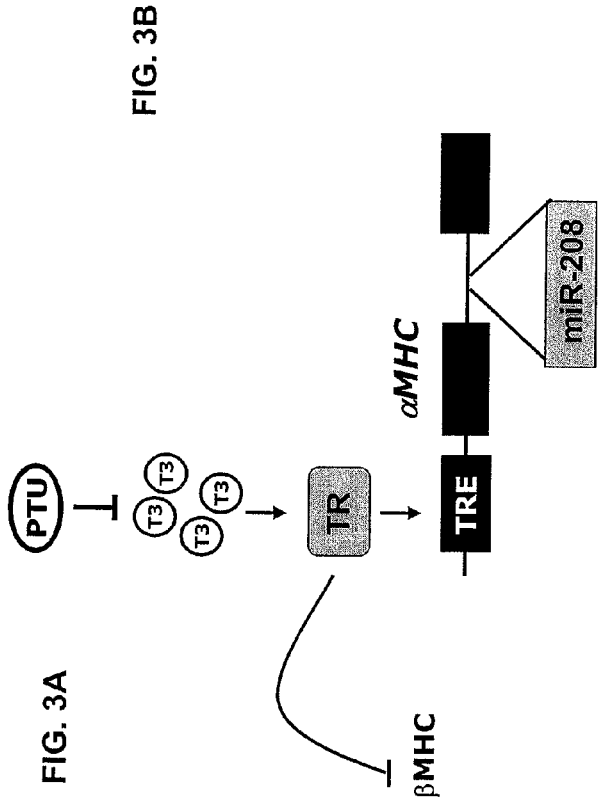
Figure 3C:
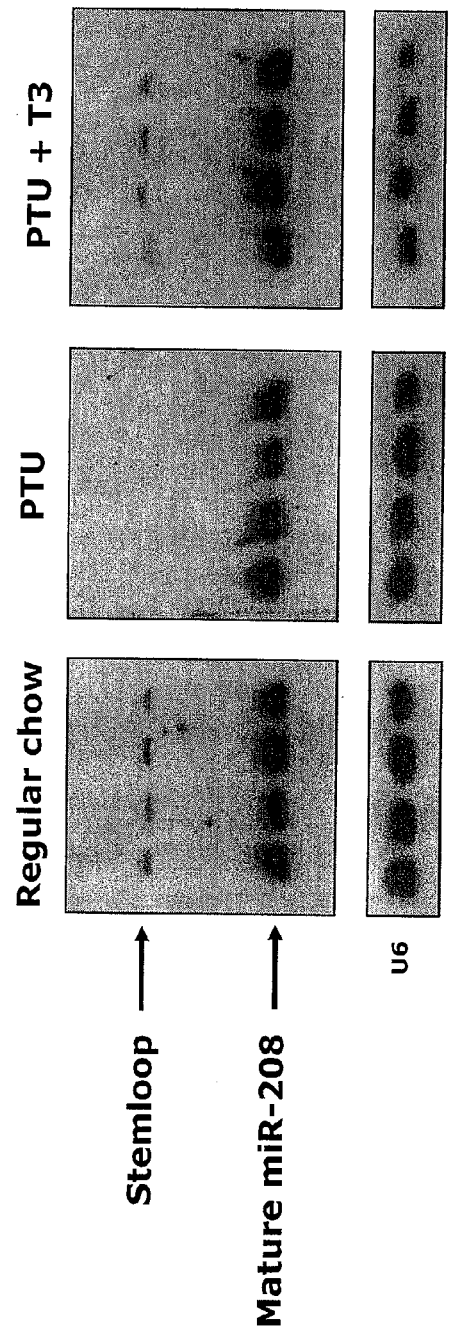

MiR-208 is an intronic miRNA that is located within the $27^{th}$ intron of the α-MHC gene. FIG. 1. The pre-miRNA encoding sequences for miR-208 for human, mouse, rat, and canine are provided in SEQ ID NO:14, SEQ ID NO:15, SEQ ID NO:16, SEQ ID NO:17, respectively. The mature miR-208 sequence is provided in SEQ ID NO:5. Like α-MHC, miR-208 is expressed solely in the heart. FIG. 2.

Using the PicTar algorithm for the identification of miRNA targets (Krek et al., 2005), the inventors identified thyroid hormone receptor associated protein 1 (THRAP1) as a predicted target for miR-208. THRAP1 3' UTR sequences from human, chimp, mouse, rat, canine, chicken, fugu, and zebrafish are provided in SEQ ID NO:6, SEQ ID NO:7, SEQ ID NO:8, SEQ ID NO:9, SEQ ID NO:10, SEQ ID NO:11, SEQ ID NO:12, and SEQ ID NO:13, respectively.

C. Inhibitors of miR-208

In general, inhibitors of miRNAs take the form of "antagomirs," short, chemically-engineered single-stranded oligonucleotides complementary to miRNAs that block the function of miRNAs (Krützfeldt et al., 2005). Other approaches include inhibition of miRNAs with antisense 2'-O-methyl (2'-OMe) oligoribonucleotides and small interfering double-stranded RNAs (siRNAs) engineered with certain "drug-like" properties (chemical modifications for stability; cholesterol conjugation for delivery) (Krützfeldt et al., 2005).

III. METHODS OF TREATING CARDIAC HYPERTROPHY

A. Therapeutic Regimens

Current medical management of cardiac hypertrophy in the setting of a cardiovascular disorder includes the use of at least two types of drugs: inhibitors of the rennin-angiotensin system, and α-adrenergic blocking agents (Bristow, 1999). Therapeutic agents to treat pathologic hypertrophy in the setting of heart failure include angiotensin II converting enzyme (ACE) inhibitors and β-adrenergic receptor blocking agents (Eichhorn and Bristow, 1996). Other pharmaceutical agents that have been disclosed for treatment of cardiac hypertrophy include angiotensin II receptor antagonists (U.S. Pat. No. 5,604,251) and neuropeptide γ antagonists (WO 98/33791). Despite currently available pharmaceutical compounds, prevention and treatment of cardiac hypertrophy, and subsequent heart failure, continue to present a therapeutic challenge.

Non-pharmacological treatment is primarily used as an adjunct to pharmacological treatment. One means of non-pharmacological treatment involves reducing the sodium in the diet. In addition, non-pharmacological treatment also entails the elimination of certain precipitating drugs, including negative inotropic agents (e.g., certain calcium channel blockers and antiarrhythmic drugs like disopyramide), cardiotoxins (e.g., amphetamines), and plasma volume expanders (e.g., nonsteroidal anti-inflammatory agents and glucocorticoids).

In one embodiment of the present invention, methods for the treatment of cardiac hypertrophy or heart failure utilizing inhibitors of miR-208 are provided. For the purposes of the present application, treatment comprises reducing one or more of the symptoms of cardiac hypertrophy, such as reduced exercise capacity, reduced blood ejection volume, increased left ventricular end diastolic pressure, increased pulmonary capillary wedge pressure, reduced cardiac output, cardiac index, increased pulmonary artery pressures, increased left ventricular end systolic and diastolic dimensions, and increased left ventricular wall stress, wall tension and wall thickness-same for right ventricle. In addition, use of inhibitors of miR-208 may prevent cardiac hypertrophy and its associated symptoms from arising.

Treatment regimens would vary depending on the clinical situation. However, long-term maintenance would appear to be appropriate in most circumstances. It also may be desirable treat hypertrophy with inhibitors of miR-208 intermittently, such as within a brief window during disease progression.

B. Combined Therapy

In another embodiment, it is envisioned to use an inhibitor of miR-208 in combination with other therapeutic modalities. Thus, in addition to the therapies described above, one may also provide to the patient more "standard" pharmaceutical cardiac therapies. Examples of other therapies include, without limitation, so-called "beta blockers," anti-hypertensives, cardiotonics, anti-thrombotics, vasodilators, hormone antagonists, iontropes, diuretics, endothelin receptor antagonists, calcium channel blockers, phosphodiesterase inhibitors, ACE inhibitors, angiotensin type 2 antagonists and cytokine blockers/inhibitors, and HDAC inhibitors.

Combinations may be achieved by contacting cardiac cells with a single composition or pharmacological formulation that includes both agents, or by contacting the cell with two distinct compositions or formulations, at the same time, wherein one composition includes the expression construct and the other includes the agent. Alternatively, the therapy using an inhibitor of miR-208 may precede or follow administration of the other agent(s) by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one would typically contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either an inhibitor of miR-208, or the other agent will be desired. In this regard, various combinations may be employed. By way of illustration, where the inhibitor of miR-208 is "A" and the other agent is "B", the following permutations based on 3 and 4 total administrations are exemplary:

---
A/B/A B/A/B B/B/A A/A/B B/A/A A/B/B B/B/B/A B/B/A/B
A/A/B/B A/B/A/B A/B/B/A B/B/A/A B/A/B/A B/A/A/B B/B/B/A
A/A/A/B B/A/A/A A/B/A/A A/A/B/A A/B/B/B B/A/B/B B/B/A/B
---

Other combinations are likewise contemplated.

C. Pharmacological Therapeutic Agents

Pharmacological therapeutic agents and methods of administration, dosages, etc., are well known to those of skill in the art (see for example, the "Physicians Desk Reference", Klaassen's "The Pharmacological Basis of Therapeutics", "Remington's Pharmaceutical Sciences", and "The Merck Index, Eleventh Edition", incorporated herein by reference in relevant parts), and may be combined with the invention in light of the disclosures herein. Some variation in dosage will necessarily occur depending on the condition of the subject being treated. The person responsible for administration will, in any event, determine the appropriate dose for the individual subject, and such individual determinations are within the skill of those of ordinary skill in the art.

Non-limiting examples of a pharmacological therapeutic agent that may be used in the present invention include an antihyperlipoproteinemic agent, an antiarteriosclerotic agent, an antithrombotic/fibrinolytic agent, a blood coagulant, an antiarrhythmic agent, an antihypertensive agent, a vasopressor, a treatment agent for congestive heart failure, an antianginal agent, an antibacterial agent or a combination thereof.

In addition, it should be noted that any of the following may be used to develop new sets of cardiac therapy target genes as β-blockers were used in the present examples (see below). While it is expected that many of these genes may overlap, new gene targets likely can be developed.

i. Antihyperlipoproteinemics

In certain embodiments, administration of an agent that lowers the concentration of one of more blood lipids and/or lipoproteins, known herein as an "antihyperlipoproteinemic," may be combined with a cardiovascular therapy according to the present invention, particularly in treatment of atherosclerosis and thickenings or blockages of vascular tissues. In certain aspects, an antihyperlipoproteinemic agent may comprise an aryloxyalkanoic/fibric acid derivative, a resin/bile acid sequesterant, a HMG CoA reductase inhibitor, a nicotinic acid derivative, a thyroid hormone or thyroid hormone analog, a miscellaneous agent or a combination thereof.

a. Aryloxyalkanoic Acid/Fibric Acid Derivatives

Non-limiting examples of aryloxyalkanoic/fibric acid derivatives include beclobrate, enzafibrate, binifibrate, ciprofibrate, clinofibrate, clofibrate (atromide-S), clofibric acid, etofibrate, fenofibrate, gemfibrozil (lobid), nicofibrate, pirifibrate, ronifibrate, simfibrate and theofibrate.

b. Resins/Bile Acid Sequesterants

Non-limiting examples of resins/bile acid sequesterants include cholestyramine (cholybar, questran), colestipol (colestid) and polidexide.

c. HMG CoA Reductase Inhibitors

Non-limiting examples of HMG CoA reductase inhibitors include lovastatin (mevacor), pravastatin (pravochol) or simvastatin (zocor).

d. Nicotinic Acid Derivatives

Non-limiting examples of nicotinic acid derivatives include nicotinate, acepimox, niceritrol, nicoclonate, nicomol and oxiniacic acid.

e. Thyroid Hormones and Analogs

Non-limiting examples of thyroid hormones and analogs thereof include etoroxate, thyropropic acid and thyroxine.

f. Miscellaneous Antihyperlipoproteinemics

Non-limiting examples of miscellaneous antihyperlipoproteinemics include acifran, azacosterol, benfluorex, β-benzalbutyramide, camitine, chondroitin sulfate, clomestrone, detaxtran, dextran sulfate sodium, 5,8,11,14,17-eicosapentaenoic acid, eritadenine, furazabol, meglutol, melinamide, mytatrienediol, ornithine, γ-oryzanol, pantethine, pentaerythritol tetraacetate, α-phenylbutyramide, pirozadil, probucol (lorelco), β-sitosterol, sultosilic acid-piperazine salt, tiadenol, triparanol and xenbucin.

ii. Antiarteriosclerotics

Non-limiting examples of an antiarteriosclerotic include pyridinol carbamate.

iii. Antithrombotic/Fibrinolytic Agents

In certain embodiments, administration of an agent that aids in the removal or prevention of blood clots may be combined with administration of a modulator, particularly in treatment of athersclerosis and vasculature (e.g., arterial) blockages. Non-limiting examples of antithrombotic and/or fibrinolytic agents include anticoagulants, anticoagulant antagonists, antiplatelet agents, thrombolytic agents, thrombolytic agent antagonists or combinations thereof.

In certain aspects, antithrombotic agents that can be administered orally, such as, for example, aspirin and wafarin (coumadin), are preferred.

a. Anticoagulants

A non-limiting example of an anticoagulant include acenocoumarol, ancrod, anisindione, bromindione, clorindione, coumetarol, cyclocumarol, dextran sulfate sodium, dicumarol, diphenadione, ethyl biscoumacetate, ethylidene dicoumarol, fluindione, heparin, hirudin, lyapolate sodium, oxazidione, pentosan polysulfate, phenindione, phenprocoumon, phosvitin, picotamide, tioclomarol and warfarin.

b. Antiplatelet Agents

Non-limiting examples of antiplatelet agents include aspirin, a dextran, dipyridamole (persantin), heparin, sulfinpyranone (anturane) and ticlopidine (ticlid).

c. Thrombolytic Agents

Non-limiting examples of thrombolytic agents include tissue plaminogen activator (activase), plasmin, pro-urokinase, urokinase (abbokinase) streptokinase (streptase), anistreplase/APSAC (eminase).

iv. Blood Coagulants

In certain embodiments wherein a patient is suffering from a hemmorage or an increased likelihood of hemmoraging, an agent that may enhance blood coagulation may be used. Non-limiting examples of a blood coagulation promoting agent include thrombolytic agent antagonists and anticoagulant antagonists.

a. Anticoagulant Antagonists

Non-limiting examples of anticoagulant antagonists include protamine and vitamine K1.

b. Thrombolytic Agent Antagonists and Antithrombotics

Non-limiting examples of thrombolytic agent antagonists include amiocaproic acid (amicar) and tranexamic acid (amstat). Non-limiting examples of antithrombotics include anagrelide, argatroban, cilstazol, daltroban, defibrotide, enoxaparin, fraxiparine, indobufen, lamoparan, ozagrel, picotamide, plafibride, tedelparin, ticlopidine and triflusal.

v. Antiarrhythmic Agents

Non-limiting examples of antiarrhythmic agents include Class I antiarrythmic agents (sodium channel blockers), Class II antiarrythmic agents (beta-adrenergic blockers), Class II antiarrythmic agents (repolarization prolonging drugs), Class IV antiarrythmic agents (calcium channel blockers) and miscellaneous antiarrythmic agents.

a. Sodium Channel Blockers

Non-limiting examples of sodium channel blockers include Class IA, Class IB and Class IC antiarrhythmic agents. Non-limiting examples of Class IA antiarrhythmic agents include disppyramide (norpace), procainamide (pronestyl) and quinidine (quinidex). Non-limiting examples of Class IB antiarrhythmic agents include lidocaine (xylocalne), tocamide (tonocard) and mexiletine (mexitil). Non-limiting examples of Class IC antiarrhythmic agents include encamide (enkaid) and flecamide (tambocor).

b. Beta Blockers

Non-limiting examples of a beta blocker, otherwise known as a β-adrenergic blocker, a β-adrenergic antagonist or a Class II antiarrhythmic agent, include acebutolol (sectral), alprenolol, amosulalol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol (brevibloc), indenolol, labetalol, levobunolol, mepindolol, metipranolol, metoprolol, moprolol, nadolol, nadoxolol, nifenalol, nipradilol, oxprenolol, penbutolol, pindolol, practolol, pronethalol, propanolol (inderal), sotalol (betapace), sulfinalol, talinolol, tertatolol, timolol, toliprolol and xibinolol. In certain aspects, the beta blocker comprises an aryloxypropanolamine derivative. Non-limiting examples of aryloxypropanolamine derivatives include acebutolol, alprenolol, arotinolol, atenolol, betaxolol, bevantolol, bisoprolol, bopindolol, bunitrolol, butofilolol, carazolol, carteolol, carvedilol, celiprolol, cetamolol, epanolol, indenolol, mepindolol, metipranolol, metoprolol, moprolol, nadolol, nipradilol, oxprenolol, penbutolol, pindolol, propanolol, talinolol, tertatolol, timolol and toliprolol.

c. Repolarization Prolonging Agents

Non-limiting examples of an agent that prolong repolarization, also known as a Class III antiarrhythmic agent, include amiodarone (cordarone) and sotalol (betapace).

d. Calcium Channel Blockers/Antagonist

Non-limiting examples of a calcium channel blocker, otherwise known as a Class IV antiarrythmic agent, include an arylalkylamine (e.g., bepridile, diltiazem, fendiline, gallopamil, prenylamine, terodiline, verapamil), a dihydropyridine derivative (felodipine, isradipine, nicardipine, nifedipine, nimodipine, nisoldipine, nitrendipine) a piperazine derivative (e.g., cinnarizine, flunarizine, lidoflazine) or a micellaneous calcium channel blocker such as bencyclane, etafenone, magnesium, mibefradil or perhexyline. In certain embodiments a calcium channel blocker comprises a long-acting dihydropyridine (nifedipine-type) calcium antagonist.

e. Miscellaneous Antiarrhythmic Agents

Non-limiting examples of miscellaneous antiarrhymic agents include adenosine (adenocard), digoxin (lanoxin), acecamide, ajmaline, amoproxan, aprindine, bretylium tosylate, bunaftine, butobendine, capobenic acid, cifenline, disopyranide, hydroquinidine, indecamide, ipatropium bromide, lidocaine, lorajmine, lorcamide, meobentine, moricizine, pirmenol, prajmaline, propafenone, pyrinoline, quinidine polygalacturonate, quinidine sulfate and viquidil.

vi. Antihypertensive Agents

Non-limiting examples of antihypertensive agents include sympatholytic, alpha/beta blockers, alpha blockers, anti-angiotensin II agents, beta blockers, calcium channel blockers, vasodilators and miscellaneous antihypertensives.

a. Alpha Blockers

Non-limiting examples of an alpha blocker, also known as an α-adrenergic blocker or an α-adrenergic antagonist, include amosulalol, arotinolol, dapiprazole, doxazosin, ergoloid mesylates, fenspiride, indoramin, labetalol, nicergoline, prazosin, terazosin, tolazoline, trimazosin and yohimbine. In certain embodiments, an alpha blocker may comprise a quinazoline derivative. Non-limiting examples of quinazoline derivatives include alfuzosin, bunazosin, doxazosin, prazosin, terazosin and trimazosin.

b. Alpha/Beta Blockers

In certain embodiments, an antihypertensive agent is both an alpha and beta adrenergic antagonist. Non-limiting examples of an alpha/beta blocker comprise labetalol (normodyne, trandate).

c. Anti-Angiotension II Agents

Non-limiting examples of anti-angiotension II agents include angiotensin converting enzyme inhibitors and angiotension II receptor antagonists. Non-limiting examples of angiotension converting enzyme inhibitors (ACE inhibitors) include alacepril, enalapril (vasotec), captopril, cilazapril, delapril, enalaprilat, fosinopril, lisinopril, moveltopril, perindopril, quinapril and ramipril. Non-limiting examples of an angiotensin II receptor blocker, also known as an angiotension II receptor antagonist, an ANG receptor blocker or an ANG-II type-1 receptor blocker (ARBS), include angiocandesartan, eprosartan, irbesartan, losartan and valsartan.

d. Sympatholytics

Non-limiting examples of a sympatholytic include a centrally acting sympatholytic or a peripherially acting sympatholytic. Non-limiting examples of a centrally acting sympatholytic, also known as an central nervous system (CNS) sympatholytic, include clonidine (catapres), guanabenz (wytensin) guanfacine (tenex) and methyldopa (aldomet). Non-limiting examples of a peripherally acting sympatholytic include a ganglion blocking agent, an adrenergic neuron blocking agent, a β-adrenergic blocking agent or a alpha1-adrenergic blocking agent. Non-limiting examples of a ganglion blocking agent include mecamylamine (inversine) and trimethaphan (arfonad). Non-limiting of an adrenergic neuron blocking agent include guanethidine (ismelin) and reserpine (serpasil). Non-limiting examples of a β-adrenergic blocker include acenitolol (sectral), atenolol (tenormin), betaxolol (kerlone), carteolol (cartrol), labetalol (normodyne, trandate), metoprolol (lopressor), nadanol (corgard), penbutolol (levatol), pindolol (visken), propranolol (inderal) and timolol (blocadren). Non-limiting examples of alpha1-adrenergic blocker include prazosin (minipress), doxazocin (cardura) and terazosin (hytrin).

e. Vasodilators

In certain embodiments a cardiovasculator therapeutic agent may comprise a vasodilator (e.g., a cerebral vasodilator, a coronary vasodilator or a peripheral vasodilator). In certain preferred embodiments, a vasodilator comprises a coronary vasodilator. Non-limiting examples of a coronary vasodilator include amotriphene, bendazol, benfurodil hemisuccinate, benziodarone, chloracizine, chromonar, clobenfurol, clonitrate, dilazep, dipyridamole, droprenilamine, efloxate, erythrityl tetranitrane, etafenone, fendiline, floredil, ganglefene, herestrol bis(β-diethylaminoethyl ether), hexobendine, itramin tosylate, khellin, lidoflanine, mannitol hexanitrane, medibazine, nicorglycerin, pentaerythritol tetranitrate, pentrinitrol, perhexyline, pimethylline, trapidil, tricromyl, trimetazidine, trolnitrate phosphate and visnadine.

In certain aspects, a vasodilator may comprise a chronic therapy vasodilator or a hypertensive emergency vasodilator. Non-limiting examples of a chronic therapy vasodilator include hydralazine (apresoline) and minoxidil (loniten). Non-limiting examples of a hypertensive emergency vasodilator include nitroprusside (nipride), diazoxide (hyperstat IV), hydralazine (apresoline), minoxidil (loniten) and verapamil.

f. Miscellaneous Antihypertensives

Non-limiting examples of miscellaneous antihypertensives include ajmaline, γ-aminobutyric acid, bufeniode, cicletainine, ciclosidomine, a cryptenamine tannate, fenoldopam, flosequinan, ketanserin, mebutamate, mecamylamine, methyldopa, methyl 4-pyridyl ketone thiosemicarbazone, muzolimine, pargyline, pempidine, pinacidil, piperoxan, primaperone, a protoveratrine, raubasine, rescimetol, rilmenidene, saralasin, sodium nitrorusside, ticrynafen, trimethaphan camsylate, tyrosinase and urapidil.

In certain aspects, an antihypertensive may comprise an arylethanolamine derivative, a benzothiadiazine derivative, a N-carboxyalkyl(peptide/lactam) derivative, a dihydropyridine derivative, a guanidine derivative, a hydrazines/phthalazine, an imidazole derivative, a quanternary ammonium compound, a reserpine derivative or a suflonamide derivative.

Arylethanolamine Derivatives. Non-limiting examples of arylethanolamine derivatives include amosulalol, bufuralol, dilevalol, labetalol, pronethalol, sotalol and sulfinalol.

Benzothiadiazine Derivatives. Non-limiting examples of benzothiadiazine derivatives include althizide, bendroflumethiazide, benzthiazide, benzylhydrochlorothiazide, buthiazide, chlorothiazide, chlorthalidone, cyclopenthiazide, cyclothiazide, diazoxide, epithiazide, ethiazide, fenquizone, hydrochlorothizide, hydroflumethizide, methyclothiazide, meticrane, metolazone, paraflutizide, polythizide, tetrachlormethiazide and trichlormethiazide.

N-carboxyalkyl(peptide/lactam) Derivatives. Non-limiting examples of N-carboxyalkyl(peptide/lactam) derivatives include alacepril, captopril, cilazapril, delapril, enalapril, enalaprilat, fosinopril, lisinopril, moveltipril, perindopril, quinapril and ramipril.

Dihydropyridine Derivatives. Non-limiting examples of dihydropyridine derivatives include amlodipine, felodipine, isradipine, nicardipine, nifedipine, nilvadipine, nisoldipine and nitrendipine.

Guanidine Derivatives. Non-limiting examples of guanidine derivatives include bethanidine, debrisoquin, guanabenz, guanacline, guanadrel, guanazodine, guanethidine, guanfacine, guanochlor, guanoxabenz and guanoxan.

Hydrazines/Phthalazines. Non-limiting examples of hydrazines/phthalazines include budralazine, cadralazine, dihydralazine, endralazine, hydracarbazine, hydralazine, pheniprazine, pildralazine and todralazine.

Imidazole Derivatives. Non-limiting examples of imidazole derivatives include clonidine, lofexidine, phentolamine, tiamenidine and tolonidine.

Quanternary Ammonium Compounds. Non-limiting examples of quanternary ammonium compounds include azamethonium bromide, chlorisondamine chloride, hexamethonium, pentacynium bis(methylsulfate), pentamethonium bromide, pentolinium tartrate, phenactropinium chloride and trimethidinium methosulfate.

Reserpine Derivatives. Non-limiting examples of reserpine derivatives include bietaserpine, deserpidine, rescinnamine, reserpine and syrosingopine.

Suflonamide Derivatives. Non-limiting examples of sulfonamide derivatives include ambuside, clopamide, furosemide, indapamide, quinethazone, tripamide and xipamide.

g. Vasopressors

Vasopressors generally are used to increase blood pressure during shock, which may occur during a surgical procedure. Non-limiting examples of a vasopressor, also known as an antihypotensive, include amezinium methyl sulfate, angiotensin amide, dimetofrine, dopamine, etifelmin, etilefrin, gepefrine, metaraminol, midodrine, norepinephrine, pholedrine and synephrine.

vii. Treatment Agents for Congestive Heart Failure

Non-limiting examples of agents for the treatment of congestive heart failure include anti-angiotension II agents, afterload-preload reduction treatment, diuretics and inotropic agents.

a. Afterload-Preload Reduction

In certain embodiments, an animal patient that can not tolerate an angiotension antagonist may be treated with a combination therapy. Such therapy may combine administration of hydralazine (apresoline) and isosorbide dinitrate (isordil, sorbitrate).

b. Diuretics

Non-limiting examples of a diuretic include a thiazide or benzothiadiazine derivative (e.g., althiazide, bendroflumethazide, benzthiazide, benzylhydrochlorothiazide, buthiazide, chlorothiazide, chlorothiazide, chlorthalidone, cyclopenthiazide, epithiazide, ethiazide, ethiazide, fenquizone, hydrochlorothiazide, hydroflumethiazide, methyclothiazide, meticrane, metolazone, paraflutizide, polythizide, tetrachloromethiazide, trichlormethiazide), an organomercurial (e.g., chlormerodrin, meralluride, mercamphamide, mercaptomerin sodium, mercumallylic acid, mercumatilin dodium, mercurous chloride, mersalyl), a pteridine (e.g., furtherene, triamterene), purines (e.g., acefylline, 7-morpholinomethyltheophylline, pamobrom, protheobromine, theobromine), steroids including aldosterone antagonists (e.g., canrenone, oleandrin, spironolactone), a sulfonamide derivative (e.g., acetazolamide, ambuside, azosemide, bumetanide, butazolamide, chloraminophenamide, clofenamide, clopamide, clorexolone, diphenylmethane-4,4'-disulfonamide, disulfamide, ethoxzolamide, furosemide, indapamide, mefruside, methazolamide, piretanide, quinethazone, torasemide, tripamide, xipamide), a uracil (e.g., aminometradine, amisometradine), a potassium sparing antagonist (e.g., amiloride, triamterene) or a miscellaneous diuretic such as aminozine, arbutin, chlorazanil, ethacrynic acid, etozolin, hydracarbazine, isosorbide, mannitol, metochalcone, muzolimine, perhexyline, ticrnafen and urea.

c. Inotropic Agents

Non-limiting examples of a positive inotropic agent, also known as a cardiotonic, include acefylline, an acetyldigitoxin, 2-amino-4-picoline, aminone, benfurodil hemisuccinate, bucladesine, cerberosine, camphotamide, convallatoxin, cymarin, denopamine, deslanoside, digitalin, digitalis, digitoxin, digoxin, dobutamine, dopamine, dopexamine, enoximone, erythropleine, fenalcomine, gitalin, gitoxin, glycocyamine, heptaminol, hydrastinine, ibopamine, a lanatoside, metamivam, milrinone, nerifolin, oleandrin, ouabain, oxyfedrine, prenalterol, proscillaridine, resibufogenin, scillaren, scillarenin, strphanthin, sulmazole, theobromine and xamoterol.

In particular aspects, an intropic agent is a cardiac glycoside, a beta-adrenergic agonist or a phosphodiesterase inhibitor. Non-limiting examples of a cardiac glycoside includes digoxin (lanoxin) and digitoxin (crystodigin). Non-limiting examples of a β-adrenergic agonist include albuterol, bambuterol, bitolterol, carbuterol, clenbuterol, clorprenaline, denopamine, dioxethedrine, dobutamine (dobutrex), dopamine (intropin), dopexamine, ephedrine, etafedrine, ethylnorepinephrine, fenoterol, formoterol, hexoprenaline, ibopamine, isoetharine, isoproterenol, mabuterol, metaproterenol, methoxyphenamine, oxyfedrine, pirbuterol, procaterol, protokylol, reproterol, rimiterol, ritodrine, soterenol, terbutaline, tretoquinol, tulobuterol and xamoterol. Non-limiting examples of a phosphodiesterase inhibitor include aminone (inocor).

d. Antianginal Agents

Antianginal agents may comprise organonitrates, calcium channel blockers, beta blockers and combinations thereof.

Non-limiting examples of organonitrates, also known as nitrovasodilators, include nitroglycerin (nitro-bid, nitrostat), isosorbide dinitrate (isordil, sorbitrate) and amyl nitrate (aspirol, vaporole).

viii. Endothelin Receptor Antagonists

Endothelin (ET) is a 21-amino acid peptide that has potent physiologic and pathophysiologic effects that appear to be involved in the development of heart failure. The effects of ET are mediated through interaction with two classes of cell surface receptors. The type A receptor (ET-A) is associated with vasoconstriction and cell growth while the type B receptor (ET-B) is associated with endothelial-cell mediated vasodilation and with the release of other neurohormones, such as aldosterone. Pharmacologic agents that can inhibit either the production of ET or its ability to stimulate relevant cells are known in the art. Inhibiting the production of ET involves the use of agents that block an enzyme termed endothelin-converting enzyme that is involved in the processing of the active peptide from its precursor. Inhibiting the ability of ET to stimulate cells involves the use of agents that block the interaction of ET with its receptors. Non-limiting examples of endothelin receptor antagonists (ERA) include Bosentan, Enrasentan, Ambrisentan, Darusentan, Tezosentan, Atrasentan, Avosentan, Clazosentan, Edonentan, sitaxsentan, TBC 3711, BQ 123, and BQ 788.

D. Surgical Therapeutic Agents

In certain aspects, the secondary therapeutic agent may comprise a surgery of some type, which includes, for example, preventative, diagnostic or staging, curative and palliative surgery. Surgery, and in particular a curative surgery, may be used in conjunction with other therapies, such as the present invention and one or more other agents.

Such surgical therapeutic agents for vascular and cardiovascular diseases and disorders are well known to those of skill in the art, and may comprise, but are not limited to, performing surgery on an organism, providing a cardiovascular mechanical prostheses, angioplasty, coronary artery reperfusion, catheter ablation, providing an implantable cardioverter defibrillator to the subject, mechanical circulatory support or a combination thereof. Non-limiting examples of a mechanical circulatory support that may be used in the present invention comprise an intra-aortic balloon counterpulsation, left ventricular assist device or combination thereof.

E. Drug Formulations and Routes for Administration to Patients

Where clinical applications are contemplated, pharmaceutical compositions will be prepared in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector or cells, dissolved or dispersed in a pharmaceutically acceptable carrier or aqueous medium. The phrases "pharmaceutically acceptable" or "pharmacologically acceptable" refers to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the vectors or cells of the compositions.

The active compositions of the present invention may include classic pharmaceutical preparations. Administration of these compositions according to the present invention may be via any common route so long as the target tissue is available via that route. This includes oral, nasal, or buccal. Alternatively, administration may be by intradermal, subcutaneous, intramuscular, intraperitoneal or intravenous injection, or by direct injection into cardiac tissue. Such compositions would normally be administered as pharmaceutically acceptable compositions, as described supra.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

For oral administration the polypeptides of the present invention generally may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention generally may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

IV. METHODS OF TREATING MUSCULOSKELETAL DISEASES AND FIBROTIC DISEASE

The up-regulation of several fast skeletal muscle contractile protein genes was observed in the hearts of miR-208 mutant mice. This up-regulation of fast skeletal muscle contractile protein genes in the hearts of miR-208 mutant mice indicates that miR-208 represses the fast skeletal muscle gene program. In skeletal muscle, the repression of slow fiber genes and activation of fast fiber genes is associated with numerous musculoskeletal disorders including disuse atrophy, muscle wasting in response to anti-gravity, and denervation. Thus, expression of miR-208 in skeletal muscle cells may be useful in repressing fast fiber genes and thereby activating the reciprocal expression of slow fiber genes. Accordingly, in certain embodiments the present invention provides methods for treating musculoskeletal disorders by administering miR-208 to the skeletal muscle of a subject who has, or is at risk for developing, a musculoskeletal disorder.

Adult skeletal muscle fibers can be categorized into fast and slow twitch subtypes based on specialized contractile and metabolic properties. These properties reflect the expression of specific sets of fast and slow contractile protein isoforms of myosin heavy and light chains, tropomyosin, and troponins, as well as myoglobin (Naya et al., 2000). Slow-twitch muscles are primarily used in chronic activities such as posture maintenance and sustained locomotor activity. Fast-twitch fibers are used primarily for high-force burst activities. The adult skeletal muscle phenotype is not static but instead retains the ability to adjust to variations in load bearing and contractile usage patterns, resulting in adaptations in morphology, phenotype, and contractile properties. For example, the removal of body loading in the microgravity environment of space flight results in a marked degree of muscle atrophy and an altered protein phenotype that correlates with a slow-to-fast change in contractile and metabolic properties for both rodents and humans (Tsika et al., 2002; Baldwin and Haddad, 2001; Edgerton and Roy, (2000); Fitts et al., 2000). Thus, in certain embodiments the present invention provides methods of treating or preventing muscle wasting in response to a reduced gravity environment by administering miR-208 to the skeletal muscle.

Disuse atrophy is a muscular atrophy that results from lack of muscle use. Disuse atrophy is typically seen in bedridden people, people with limbs in casts, or those who are inactive for other reasons. In addition, disruptions in myofiber electrical activity, including denervation, lead to muscle atrophy. After short periods of disuse, muscle atrophy is reversible. Extreme disuse of a muscle, however, may result in a permanent loss of skeletal muscle fibers and the replacement of those fibers by connective tissue. It is contemplated that by repressing fast fiber genes in skeletal muscle and thereby activating the reciprocal expression of slow fiber genes, the symptoms of muscle atrophy may be reduced or prevented. Thus, in certain embodiments the present invention provides methods of treating or preventing muscle atrophy by administering miR-208 to the skeletal muscle.

In addition, to playing an important role in controlling fibrosis in the heart, the ubiquitous expression of the miR-29 family of molecules means that it also can play a role in other fibrotic indications, such as those involving the kidney, liver and lungs. Fibrosis is also observed secondary to diabetes. Type 1 and type 2 diabetic patients are at increased risk of cardiomyopathy. Cardiomyopathy in diabetes is associated with a cluster of features including decreased diastolic compliance, interstitial fibrosis and myocyte hypertrophy. Since miR-208 inhibits miR-29, inhibition of miR-208 can be used to block both cardiac fibrosis, as well as non-cardiac fibrosis.

Congenital Hepatic Fibrosis (CHF) is a rare disease that affects both the liver and kidneys. The patient inherits as an autosomal recessive trait. Liver abnormalities are hepatomegaly, increased pressure in the venous system that carries blood from different organs to the liver (portal hypertension), and fiber-like connective tissue that spreads over and through the liver (hepatic fibrosis), often referred to as hepatic lesions. Affected individuals also have impaired renal function, usually caused by an autosomal recessive polycystic kidney disease (ARPKD). Impaired renal function associated with CHF in adults is caused by an autosomal dominant polycystic kidney disease (ADPKD).

Progressive loss of renal function is associated not only with development of glomerulosclerosis, but also with that of interstitial fibrosis. Interstitial fibrosis is characterized by the destruction of renal tubules and interstitial capillaries as well as by the accumulation of extracellular matrix proteins. The severity of tubulointerstitial fibrosis has long been considered as a crucial determinant of progressive renal injury in both human and experimental glomerulonephritis.

Pulmonary fibrosis, or scarring of the lung, results from the gradual replacement of normal lung air sacs with fibrotic tissue. When the scar forms, the tissue becomes thicker, causing an irreversible loss of the tissue's ability to transfer oxygen into the bloodstream. Symptoms include shortness of breath (particularly with exertion), chronic dry, hacking cough, fatigue and weakness, discomfort in the chest, loss of appetite and rapid weight loss.

Some have postulated that pulmonary fibrosis might be an autoimmune disorder, or the after effects of a viral infection. However, there is a growing belief that genetic predisposition is a key factor. A mutation in the SP-C protein has been found to exist in families with a history of pulmonary fibrosis. The most current thinking is that the fibrotic process is a reaction (predisposed by genetics) to microscopic injury to the lung. While the exact cause remains unknown, associations have been made with inhaled environmental and occupational pollutants, cigarette smoking, diseases such as scleroderma, rheumatoid arthritis, lupus and sarcoidosis, certain medications and therapeutic radiation.

Diabetic cardiomyopathy in patients is characterized by myocardial hypertrophy, interstitial fibrosis, capillary endothelial changes, and capillary basal laminae thickening and is secondary to alterations in collagen structure. The increased accumulation of collagen is primarily found in the epicardial and perivascular regions, where is induces an impairment of LV diastolic function often leading to heart failure.

V. KITS

Any of the compositions described herein may be comprised in a kit. In a non-limiting example, an individual miRNA is included in a kit. The kit may further include water and hybridization buffer to facilitate hybridization of the two strands of the miRNAs. The kit may also include one or more transfection reagent(s) to facilitate delivery of the miRNA to cells.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit (labeling reagent and label may be packaged together), the kit also will generally contain a second, third or other additional container into which the additional components may be separately placed. However, various combinations of components may be comprised in a vial. The kits of the present invention also will typically include a means for containing the nucleic acids, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred.

However, the components of the kit may be provided as dried powder(s). When reagents and/or components are provided as a dry powder, the powder can be reconstituted by the addition of a suitable solvent. It is envisioned that the solvent may also be provided in another container means.

The container means will generally include at least one vial, test tube, flask, bottle, syringe and/or other container means, into which the nucleic acid formulations are placed, preferably, suitably allocated. The kits may also comprise a second container means for containing a sterile, pharmaceutically acceptable buffer and/or other diluent.

The kits of the present invention will also typically include a means for containing the vials in close confinement for commercial sale, such as, e.g., injection and/or blow-molded plastic containers into which the desired vials are retained.

Such kits may also include components that preserve or maintain the miRNA or that protect against its degradation. Such components may be RNAse-free or protect against RNAses. Such kits generally will comprise, in suitable means, distinct containers for each individual reagent or solution.

A kit will also include instructions for employing the kit components as well the use of any other reagent not included in the kit. Instructions may include variations that can be implemented.

It is contemplated that such reagents are embodiments of kits of the invention. Such kits, however, are not limited to the particular items identified above and may include any reagent used for the manipulation or characterization of miRNA.

VI. SCREENING METHODS

The present invention further comprises methods for identifying inhibitors of miR-208 that are useful in the prevention or treatment or reversal of cardiac hypertrophy or heart failure. These assays may comprise random screening of large libraries of candidate substances; alternatively, the assays may be used to focus on particular classes of compounds selected with an eye towards structural attributes that are believed to make them more likely to inhibit the expression and/or function of miR-208.

To identify a modulator of miR-208, one generally will determine the function of a miR-208 in the presence and absence of the candidate substance. For example, a method generally comprises:

(a) providing a candidate modulator;
(b) admixing the candidate modulator with a miR-208;
(c) measuring miR-208 activity; and
(d) comparing the activity in step (c) with the activity in the absence of the candidate modulator,
wherein a difference between the measured activities indicates that the candidate modulator is, indeed, a modulator of miR-208.

Assays also may be conducted in isolated cells, organs, or in living organisms.

It will, of course, be understood that all the screening methods of the present invention are useful in themselves notwithstanding the fact that effective candidates may not be found. The invention provides methods for screening for such candidates, not solely methods of finding them.

A. Modulators

As used herein the term "candidate substance" refers to any molecule that may potentially modulate the β-MHC-inducing function of miR-208. One will typically acquire, from various commercial sources, molecular libraries that are believed to meet the basic criteria for useful drugs in an effort to "brute force" the identification of useful compounds. Screening of such libraries, including combinatorially-generated libraries (e.g., antagomir libraries), is a rapid and efficient way to screen large number of related (and unrelated) compounds for activity. Combinatorial approaches also lend themselves to rapid evolution of potential drugs by the creation of second, third, and fourth generation compounds modeled on active, but otherwise undesirable compounds.

B. In Vitro Assays

A quick, inexpensive and easy assay to run is an in vitro assay. Such assays generally use isolated molecules, can be run quickly and in large numbers, thereby increasing the amount of information obtainable in a short period of time. A variety of vessels may be used to run the assays, including test tubes, plates, dishes and other surfaces such as dipsticks or beads.

A technique for high throughput screening of compounds is described in WO 84/03564. Large numbers of small antogomir compounds may be synthesized on a solid substrate, such as plastic pins or some other surface. Such molecules can be rapidly screening for their ability to hybridize to miR-208.

C. In Cyto Assays

The present invention also contemplates the screening of compounds for their ability to modulate miR-208 express and function in cells. Various cell lines, including those derived from skeletal muscle cells, can be utilized for such screening assays, including cells specifically engineered for this purpose. Primary cardiac cells also may be used, as can the H9C2 cell line.

D. In vivo Assays

In vivo assays involve the use of various animal models of heart disease or musculoskeletal disease, including transgenic animals, that have been engineered to have specific defects, or carry markers that can be used to measure the ability of a candidate substance to reach and effect different cells within the organism. Due to their size, ease of handling, and information on their physiology and genetic make-up, mice are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for inhibitors may be conducted using an animal model derived from any of these species.

Treatment of animals with test compounds will involve the administration of the compound, in an appropriate form, to the animal. Administration will be by any route that could be utilized for clinical purposes. Determining the effectiveness of a compound in vivo may involve a variety of different criteria, including but not limited to alteration of hypertrophic signaling pathways and physical symptoms of hypertrophy. Also, measuring toxicity and dose response can be performed in animals in a more meaningful fashion than in in vitro or in cyto assays.

VII. VECTORS FOR CLONING, GENE TRANSFER AND EXPRESSION

Within certain embodiments expression vectors are employed to express miR-208 or an inhibitor thereof. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

A. Regulatory Elements

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

In certain embodiments, the nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

In other embodiments, the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose.

By employing a promoter with well-known properties, the level and pattern of expression of the protein of interest following transfection or transformation can be optimized. Further, selection of a promoter that is regulated in response to specific physiologic signals can permit inducible expression of the gene product. Tables 1 and 2 list several regulatory elements that may be employed, in the context of the present invention, to regulate the expression of the gene of interest. This list is not intended to be exhaustive of all the possible elements involved in the promotion of gene expression but, merely, to be exemplary thereof.

Enhancers are genetic elements that increase transcription from a promoter located at a distant position on the same molecule of DNA. Enhancers are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of viral promoters, cellular promoters/enhancers and inducible promoters/enhancers that could be used in combination with the nucleic acid encoding a gene of interest in an expression construct (Table 1 and Table 2). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 1

Promoter and/or Enhancer

| Promoter/Enhancer | References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987a |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| α$_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |

TABLE 1-continued

Promoter and/or Enhancer

| Promoter/Enhancer | References |
|---|---|
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 2

Inducible Elements

| Element | Inducer | References |
|---|---|---|
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Ponta et al., 1985; Sakai et al., 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

Of particular interest are muscle specific promoters, and more particularly, cardiac specific promoters. These include the myosin light chain-2 promoter (Franz et al., 1994; Kelly et al., 1995), the alpha actin promoter (Moss et al., 1996), the troponin 1 promoter (Bhavsar et al., 1996); the $Na^+/Ca^{2+}$ exchanger promoter (Barnes et al., 1997), the dystrophin promoter (Kimura et al., 1997), the alpha7 integrin promoter (Ziober and Kramer, 1996), the brain natriuretic peptide promoter (LaPointe et al., 1996) and the alpha B-crystallin/small heat shock protein promoter (Gopal-Srivastava, 1995), alpha myosin heavy chain promoter (Yamauchi-Takihara et al., 1989) and the ANF promoter (LaPointe et al., 1988).

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

B. Selectable Markers

In certain embodiments of the present invention, the cells contain nucleic acid constructs of the present invention, a cell may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

C. Multigene Constructs and IRES

In certain embodiments of the invention, the use of internal ribosome binding sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picanovirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

D. Delivery of Expression Vectors

There are a number of ways in which expression vectors may introduced into cells. In certain embodiments of the invention, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kB of foreign genetic material but can be readily introduced in a variety of cell lines and laboratory animals (Nicolas and Rubenstein, 1988; Temin, 1986).

One of the preferred methods for in vivo delivery involves the use of an adenovirus expression vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

The expression vector comprises a genetically engineered form of adenovirus. Knowledge of the genetic organization of adenovirus, a 36 kB, linear, double-stranded DNA virus, allows substitution of large pieces of adenoviral DNA with foreign sequences up to 7 kB (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1-deleted virus is incomplete.

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors, as described by Karlsson et al. (1986), or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$-$10^{12}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1991). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intactsequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

With the recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al., introduced the chloramphenicol acetyl-transferase (CAT) gene into duck hepatitis B virus genome in the place of the polymerase, surface, and pre-surface coding sequences. It was co-transfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al., (1980) demonstrated the feasibility of liposome-mediated delivery and expression of foreign DNA in cultured chick embryo, HeLa and hepatoma cells. Nicolau et al., (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention.

Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type by any number of receptor-ligand systems with or without liposomes. For example, epidermal growth factor (EGF) may be used as the receptor for mediated delivery of a nucleic acid into cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In a particular example, the oligonucleotide may be administered in combination with a cationic lipid. Examples of cationic lipids include, but are not limited to, lipofectin, DOTMA, DOPE, and DOTAP. The publication of WO0071096, which is specifically incorporated by reference, describes different formulations, such as a DOTAP:cholesterol or cholesterol derivative formulation that can effectively be used for gene therapy. Other disclosures also discuss different lipid or liposomal formulations including nanoparticles and methods of administration; these include, but are not limited to, U.S. Patent Publication 20030203865, 20020150626, 20030032615, and 20040048787, which are specifically incorporated by reference to the extent they disclose formulations and other related aspects of administration and delivery of nucleic acids. Methods used for forming particles are also disclosed in U.S. Pat. Nos. 5,844,107, 5,877, 302, 6,008,336, 6,077,835, 5,972,901, 6,200,801, and 5,972, 900, which are incorporated by reference for those aspects.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

VIII. METHODS OF MAKING TRANSGENIC MICE

A particular embodiment of the present invention provides transgenic animals that lack one or both functional miR-208 alleles. Also, transgenic animals that express miR-208 under the control of an inducible, tissue selective or a constitutive promoter, recombinant cell lines derived from such animals, and transgenic embryos may be useful in determining the exact role that miR-208 plays in the development and differentiation of cardiomyocytes and in the development of pathologic cardiac hypertrophy and heart failure. Furthermore, these transgenic animals may provide an insight into heart development. The use of constitutively expressed miR-208 encoding nucleic acid provides a model for over- or unregulated expression. Also, transgenic animals that are "knocked out" for miR-208, in one or both alleles, are contemplated.

In a general aspect, a transgenic animal is produced by the integration of a given transgene into the genome in a manner that permits the expression of the transgene. Methods for producing transgenic animals are generally described by Wagner and Hoppe (U.S. Pat. No. 4,873,191; incorporated herein by reference), and Brinster et al. (1985; incorporated herein by reference).

Typically, a gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish.

DNA clones for microinjection can be prepared by any means known in the art. For example, DNA clones for microinjection can be cleaved with enzymes appropriate for removing the bacterial plasmid sequences, and the DNA fragments electrophoresed on 1% agarose gels in TBE buffer, using standard techniques. The DNA bands are visualized by staining with ethidium bromide, and the band containing the expression sequences is excised. The excised band is then placed in dialysis bags containing 0.3 M sodium acetate, pH 7.0. DNA is electroeluted into the dialysis bags, extracted with a 1:1 phenol:chloroform solution and precipitated by two volumes of ethanol. The DNA is redissolved in 1 ml of low salt buffer (0.2 M NaCl, 20 mM Tris, pH 7.4, and 1 mM EDTA) and purified on an Elutip-D™ column. The column is first primed with 3 ml of high salt buffer (1 M NaCl, 20 mM Tris, pH 7.4, and 1 mM EDTA) followed by washing with 5 ml of low salt buffer. The DNA solutions are passed through the column three times to bind DNA to the column matrix. After one wash with 3 ml of low salt buffer, the DNA is eluted with 0.4 ml high salt buffer and precipitated by two volumes of ethanol. DNA concentrations are measured by absorption at 260 nm in a UV spectrophotometer. For microinjection, DNA concentrations are adjusted to 3 µg/ml in 5 mM Tris, pH 7.4 and 0.1 mM EDTA. Other methods for purification of DNA for microinjection are described in in Palmiter et al. (1982); and in Sambrook et al. (2001).

In an exemplary microinjection procedure, female mice six weeks of age are induced to superovulate with a 5 IU injection (0.1 cc, ip) of pregnant mareserum gonadotropin (PMSG; Sigma) followed 48 hours later by a 5 IU injection (0.1 cc, ip) of human chorionic gonadotropin (hCG; Sigma). Females are placed with males immediately after hCG injection. Twenty-one hours after hCG injection, the mated females are sacrificed by $CO_2$ asphyxiation or cervical dislocation and embryos are recovered from excised oviducts and placed in Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA (EBSS) in a 37.5° C. incubator with a humidified atmosphere at 5% $CO_2$, 95% air until the time of injection. Embryos can be implanted at the two-cell stage.

Randomly cycling adult female mice are paired with vasectomized males. C57BL/6 or Swiss mice or other comparable strains can be used for this purpose. Recipient females are mated at the same time as donor females. At the time of embryo transfer, the recipient females are anesthetized with an intraperitoneal injection of 0.015 ml of 2.5% avertin per gram of body weight. The oviducts are exposed by a single midline dorsal incision. An incision is then made through the body wall directly over the oviduct. The ovarian bursa is then torn with watchmakers forceps. Embryos to be transferred are placed in DPBS (Dulbecco's phosphate buffered saline) and in the tip of a transfer pipet (about 10 to 12 embryos). The pipet tip is inserted into the infundibulum and the embryos transferred. After the transfer, the incision is closed by two sutures.

IX. DEFINITIONS

As used herein, the term "heart failure" is broadly used to mean any condition that reduces the ability of the heart to pump blood. As a result, congestion and edema develop in the tissues. Most frequently, heart failure is caused by decreased contractility of the myocardium, resulting from reduced coronary blood flow; however, many other factors may result in heart failure, including damage to the heart valves, vitamin deficiency, and primary cardiac muscle disease. Though the precise physiological mechanisms of heart failure are not entirely understood, heart failure is generally believed to involve disorders in several cardiac autonomic properties, including sympathetic, parasympathetic, and baroreceptor responses. The phrase "manifestations of heart failure" is used broadly to encompass all of the sequelae associated with heart failure, such as shortness of breath, pitting edema, an enlarged tender liver, engorged neck veins, pulmonary rales and the like including laboratory findings associated with heart failure.

The term "treatment" or grammatical equivalents encompasses the improvement and/or reversal of the symptoms of heart failure (i.e., the ability of the heart to pump blood). "Improvement in the physiologic function" of the heart may be assessed using any of the measurements described herein (e.g., measurement of ejection fraction, fractional shortening, left ventricular internal dimension, heart rate, etc.), as well as any effect upon the animal's survival. In use of animal models, the response of treated transgenic animals and untreated transgenic animals is compared using any of the assays described herein (in addition, treated and untreated non-transgenic animals may be included as controls). A compound which causes an improvement in any parameter associated with heart failure used in the screening methods of the instant invention may thereby be identified as a therapeutic compound.

The term "dilated cardiomyopathy" refers to a type of heart failure characterized by the presence of a symmetrically dilated left ventricle with poor systolic contractile function and, in addition, frequently involves the right ventricle.

The term "compound" refers to any chemical entity, pharmaceutical, drug, and the like that can be used to treat or prevent a disease, illness, sickness, or disorder of bodily function. Compounds comprise both known and potential therapeutic compounds. A compound can be determined to be therapeutic by screening using the screening methods of the present invention. A "known therapeutic compound" refers to a therapeutic compound that has been shown (e.g., through animal trials or prior experience with administration to humans) to be effective in such treatment. In other words, a known therapeutic compound is not limited to a compound efficacious in the treatment of heart failure.

As used herein, the term "agonist" refers to molecules or compounds that mimic the action of a "native" or "natural" compound. Agonists may be homologous to these natural compounds in respect to conformation, charge or other characteristics. Thus, agonists may be recognized by receptors expressed on cell surfaces. This recognition may result in physiologic and/or biochemical changes within the cell, such that the cell reacts to the presence of the agonist in the same manner as if the natural compound was present. Agonists may include proteins, nucleic acids, carbohydrates, or any other molecules that interact with a molecule, receptor, and/or pathway of interest.

As used herein, the term "cardiac hypertrophy" refers to the process in which adult cardiac myocytes respond to stress through hypertrophic growth. Such growth is characterized by cell size increases without cell division, assembling of additional sarcomeres within the cell to maximize force generation, and an activation of a fetal cardiac gene program. Cardiac hypertrophy is often associated with increased risk of morbidity and mortality, and thus studies aimed at understanding the molecular mechanisms of cardiac hypertrophy could have a significant impact on human health.

As used herein, the terms "antagonist" and "inhibitor" refer to molecules, compounds, or nucleic acids that inhibit the action of a cellular factor that may be involved in cardiac hypertrophy. Antagonists may or may not be homologous to these natural compounds in respect to conformation, charge or other characteristics. Thus, antagonists may be recognized by the same or different receptors that are recognized by an agonist. Antagonists may have allosteric effects that prevent the action of an agonist. Alternatively, antagonists may prevent the function of the agonist. In contrast to the agonists, antagonistic compounds do not result in pathologic and/or biochemical changes within the cell such that the cell reacts to the presence of the antagonist in the same manner as if the cellular factor was present. Antagonists and inhibitors may include proteins, nucleic acids, carbohydrates, or any other molecules that bind or interact with a receptor, molecule, and/or pathway of interest.

As used herein, the term "modulate" refers to a change or an alteration in a biological activity. Modulation may be an increase or a decrease in protein activity, a change in kinase activity, a change in binding characteristics, or any other change in the biological, functional, or immunological properties associated with the activity of a protein or other structure of interest. The term "modulator" refers to any molecule or compound which is capable of changing or altering biological activity as described above.

The term "β-adrenergic receptor antagonist" refers to a chemical compound or entity that is capable of blocking, either partially or completely, the beta (β) type of adrenoreceptors (i.e., receptors of the adrenergic system that respond to catecholamines, especially norepinephrine). Some β-adrenergic receptor antagonists exhibit a degree of specificity for one receptor subtype (generally $β_1$); such antagonists are termed "$β_1$-specific adrenergic receptor antagonists" and "$β_2$-specific adrenergic receptor antagonists." The term β-adrenergic receptor antagonist" refers to chemical compounds that are selective and non-selective antagonists. Examples of β-adrenergic receptor antagonists include, but are not limited to, acebutolol, atenolol, butoxamine, carteolol, esmolol, labetolol, metoprolol, nadolol, penbutolol, propanolol, and timolol. The use of derivatives of known β-adrenergic receptor antagonists is encompassed by the methods of the present invention. Indeed any compound, which functionally behaves as a β-adrenergic receptor antagonist is encompassed by the methods of the present invention.

The terms "angiotensin-converting enzyme inhibitor" or "ACE inhibitor" refer to a chemical compound or entity that is capable of inhibiting, either partially or completely, the enzyme involved in the conversion of the relatively inactive angiotensin I to the active angiotensin II in the rennin-angiotensin system. In addition, the ACE inhibitors concomitantly inhibit the degradation of bradykinin, which likely significantly enhances the antihypertensive effect of the ACE inhibitors. Examples of ACE inhibitors include, but are not limited to, benazepril, captopril, enalopril, fosinopril, lisinopril, quiapril and ramipril. The use of derivatives of known ACE inhibitors is encompassed by the methods of the present invention. Indeed any compound, which functionally behaves as an ACE inhibitor, is encompassed by the methods of the present invention.

As used herein, the term "genotypes" refers to the actual genetic make-up of an organism, while "phenotype" refers to physical traits displayed by an individual. In addition, the "phenotype" is the result of selective expression of the genome (i.e., it is an expression of the cell history and its response to the extracellular environment). Indeed, the human genome contains an estimated 30,000-35,000 genes. In each cell type, only a small (i.e., 10-15%) fraction of these genes are expressed.

X. EXAMPLES

The following examples are included to further illustrate various aspects of the invention. It should be appreciated by those of skill in the art that the techniques disclosed in the examples which follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials & Methods

Northern blot analysis. Cardiac tissue samples of left ventricles of anonymous humans diagnosed as having non-failing or failing hearts were obtained from Gilead Colorado (Westminster, Colo.). Total RNA was isolated from mouse, rat and human cardiac tissue samples by using Trizol reagent (Gibco/BRL). Northern blots to detect microRNAs were performed as described previously (1). A U6 probe served as a loading control (U6 forward: 5-GTGCTCGCTTCG-GCAGC-3 (SEQ ID NO:18), U6 reverse: 5-AAAATATG-GAACGCTTCACGAATTTGCG-3 (SEQ ID NO:19)). To detect αMHC expression, a Northern blot containing 10 μg of RNA from cardiac tissue of both adult wild-type and miR-208 mutant animals was probed with a cDNA fragment of αMHC covering a part of the 5'UTR region and first exon.

PTU treatment. Thyroid hormone deficiency was induced by feeding animals for the indicated durations with iodine-free chow supplemented with 0.15% PTU purchased from Harlan Teklad Co. (TD 97061) (Madison, Wis.).

Microarray and realtime PCR analysis. Total RNA from cardiac tissue was isolated using Trizol (Invitrogen). Microarray analysis was performed using Mouse Genome 430 2.0 array (Affymetrix). RT-PCR with random hexamer primers (Invitrogen) was performed on RNA samples, after which the expression of a subset of genes was analyzed by quantitative real time PCR using Taqman probes purchased from ABI.

Generation of miR-208 mutant mice. To generate the miR-208 targeting vector, a 0.4 kb fragment (5' arm) extending upstream of the miR-208 coding region was digested with SacII and NotI and ligated into the pGKneoF2L2dta targeting plasmid upstream of the loxP sites and the Frt-flanked neomycin cassette. A 3.3 kb fragment (3' arm) was digested with SalI and HindIII and ligated into the vector between the neomycin resistance and Dta negative selection cassettes. Targeted ES-cells carrying the disrupted allele were identified by Southern blot analysis with 5' and 3' probes. Three miR-208 targeted ES clones were identified and used for blastocyst injection. The resulting chimeric mice were bred to C57BL/6 to obtain germline transmission of the mutant allele. PCR primer sequences are available upon request.

Western blotting. Myosin was extracted from cardiac tissue as described (Morkin, 2000). MHC isoforms were separated by SDS PAGE and Western blotting was performed with mouse monoclonal αMHC (BA-G5) (ATCC, Rockville, Md.) and mouse monoclonal antimyosin (slow, skeletal M8421) (Sigma, Mo.), which is highly specific for βMHC. To detect all striated myosin a pan specific antibody (mouse monoclonal 3-48; Accurate Chemical & Scientific Corporation, NY) was used. THRAP1 was detected by immunoprecipitation from 400 μg of cardiac protein lysate. After pre-clearing the samples for 1 hour at 4° C., the supernatant was incubated overnight at 4° C. with 1 μl rabbit polyclonal anti-THRAP1 (a kind gift of R. Roeder, Rockefeller University) and 15 μl of protein A beads. The beads were washed three times with lysis buffer and boiled in SDS sample buffer. Immunoprecipitated THRAP1 protein was resolved by SDS-PAGE and analyzed using rabbit polyclonal anti-THRAP1 at a dilution of 1:3000 and anti-rabbit IgG conjugated to horseradish peroxidase at a dilution of 1:5000 with detection by Luminol Reagent (Santa Cruz).

Histological analysis and RNA in situ hybridization. Tissues used for histology were incubated in Krebs-Henselheit solution, fixed in 4% paraformaldehyde, sectioned, and processed for hematoxylin and eosin (H&E) and Masson's Trichrome staining or in situ hybridization by standard techniques (Krenz and Robbins, 2004). $^{35}$S-labeled RNA probes were generated using Maxiscript kit (Amersham). Signals were pseudocolored in red using Adobe Photoshop.

Transthoracic echocardiography. Cardiac function and heart dimensions were evaluated by two-dimensional echocardiography in conscious mice using a Vingmed System (GE Vingmed Ultrasound, Horten, Norway) and a 11.5-MHz linear array transducer. M-mode tracings were used to measure anterior and posterior wall thicknesses at end diastole and end systole. Left ventricular (LV) internal diameter (LVID) was measured as the largest anteroposterior diameter in either diastole (LVIDd) or systole (LVIDs). The data were analyzed by a single observer blinded to mouse genotype. LV fractional shortening (FS) was calculated according to the following formula: FS (%)=[(LVIDd—LVIDs)/LVIDd]×100.

Generation of transgenic mice. A mouse genomic fragment flanking the miRNA of interest was subcloned into a cardiac-specific expression plasmid containing the α-MHC and human GH poly(A)+ signal (Kiriazis and Kranias, 2000).

Genomic DNA was isolated from mouse tail biopsies and analyzed by PCR using primers specific for the human GH poly(A)+ signal.

Plasmids and transfection assays. A 305 bp genomic fragment encompassing the miR-208 coding region was amplified by PCR and ligated into pCMV6. A 1 kb fragment encompassing the entire murine THRAP1-UTR was PCR-amplified and ligated into an HA-tagged pCMV6 expression construct and the firefly luciferase (f-luc) reporter construct (pMIR-REPORT™, Ambion). A mutation of the UCGU-CUUA miR-208 seed binding sequence was constructed through PCR-based mutagenesis.

Exaple 2

Results miR-208 is a central regulator in cardiac contractile function. Intronic microRNAs are transcribed as part of the host gene transcript, spliced out and processed into the mature miRNA. MiR-208 is an intronic miRNA that is located within the $27^{th}$ intron of the α-MHC gene. FIG. 1. Like α-MHC, miR-208 is expressed solely in the heart. FIG. 2. Post-natally thyroid hormone regulates the expression of ventricular myosin isoenzymes by stimulating synthesis of α-MHC and inhibiting expression of β-MHC. To examine whether blockade of thyroid hormone signaling also influences miRNA 208 expression, the inventors used cardiac rat samples that were exposed to propylthiouracil (PTU) for a set period of time. PTU blocks thyroid hormone biosynthesis by inhibiting the "organification" of iodine—its incorporation into T3 and T4, and thereby represses α-MHC expression and increases β-MHC. Northern blot analysis indicated a perfect correlation between the expression level of α-MHC and the level of pre-miRNA, the so-called "stemloop," while the mature miRNA remained present for weeks thereafter. FIGS. 3A-C and FIGS. 4A-C.

Figure 5:
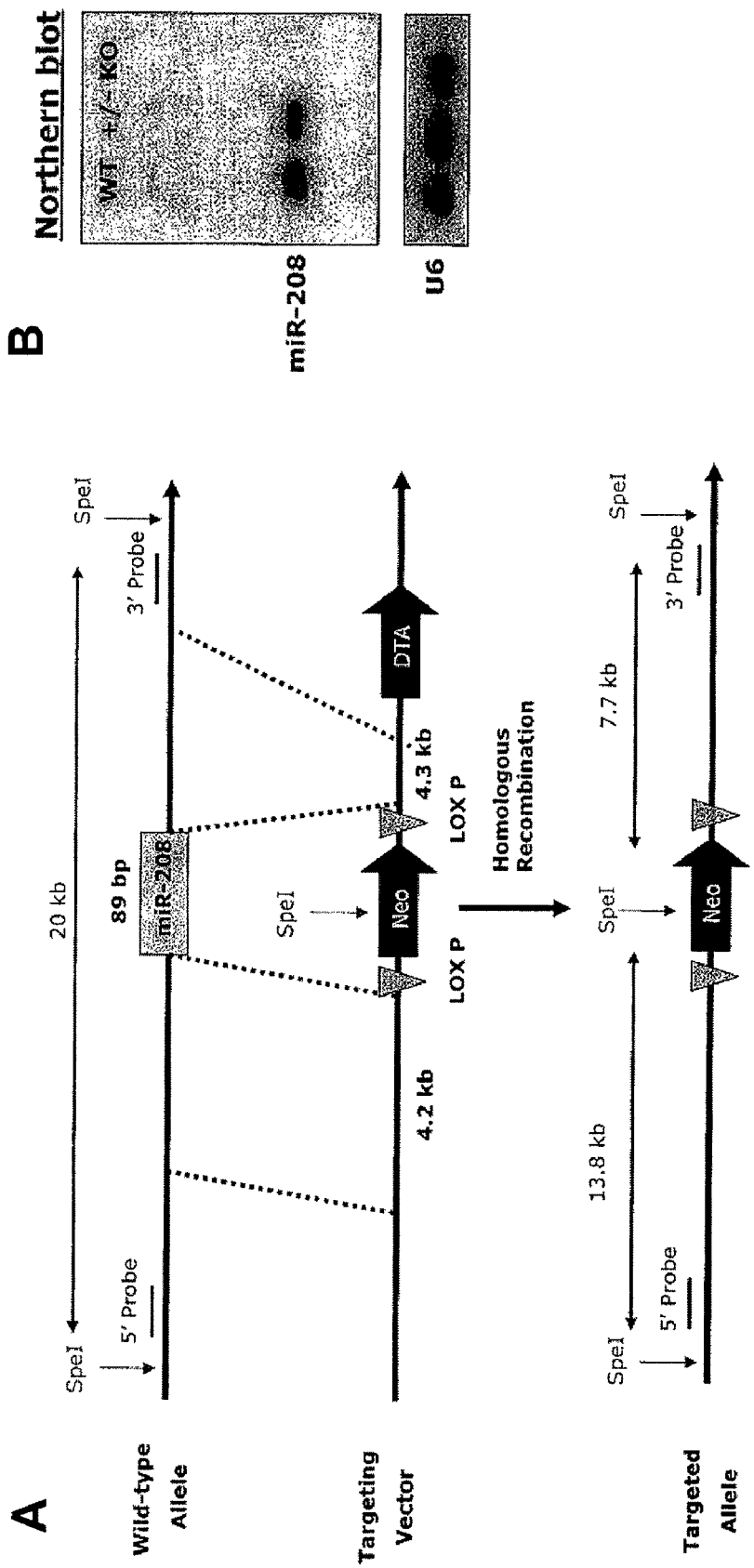
FIGS. 5A-B—An miR-208 gene knockout.

To study the role of miR-208, the inventors engineered miR-208 null mice. FIG. 5. Although this did not interfere with α-MHC transcription or translation, microarray analysis on cardiac tissue of 2-month old wild-type and miR-208 KO mice, indicated that removal of miR-208 lead to strong induction of fast skeletal muscle genes. FIGS. 6A-B, and FIG. 7.

Figure 8:
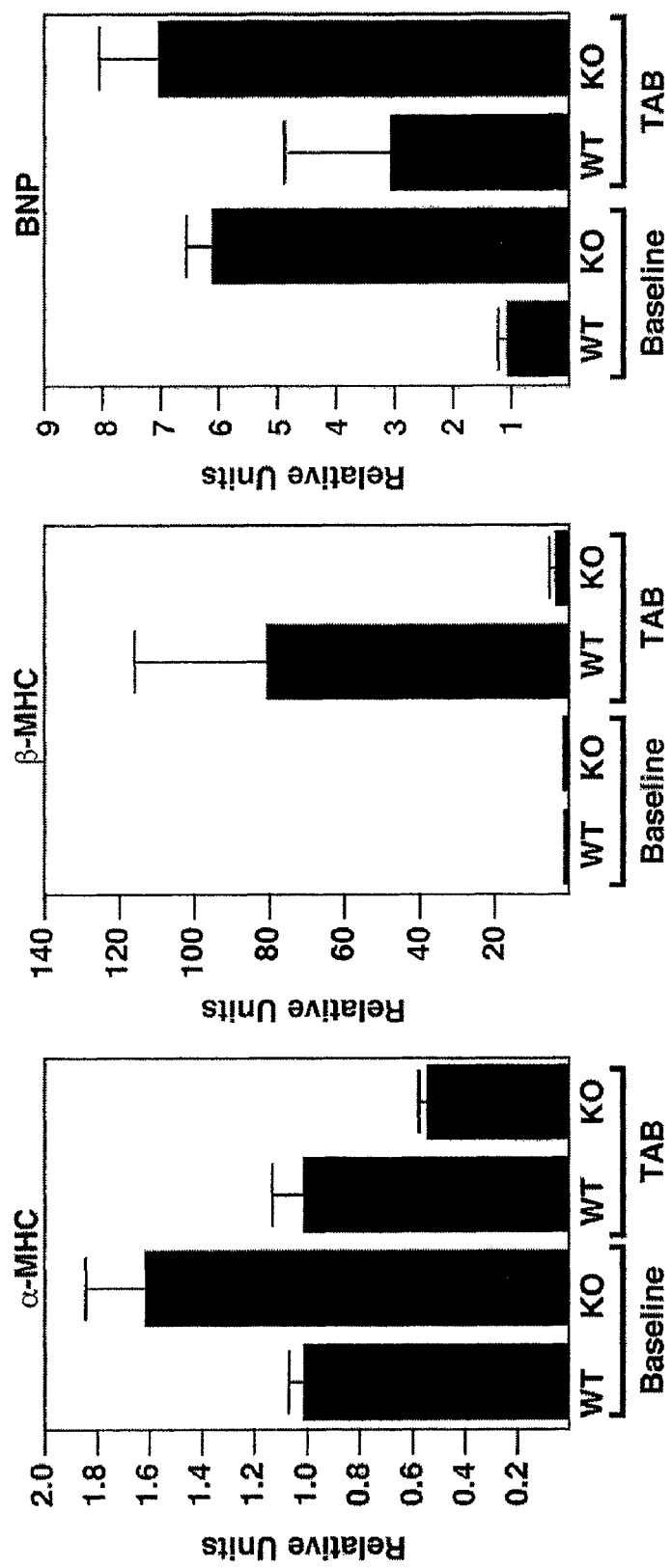
FIG. 8—Dysregulation of cardiac stress response genes in miR-208 knock-out mice.

To examine the effect of miR-208 removal during cardiac stress, the inventors exposed both wild-type and miR-208 KO animals to transverse aortic band constriction (TAB). TAB is a potent inducer of cardiac hypertrophy, and concomitant hypertrophic gene expression. While the wild-type animals showed a severe increase in β-MHC expression, the KO animals failed to show this induction. FIG. 8.

TABLE 3

KO versus WT 3 weeks after TAB

| Gene | Fold change compared to wild-type after TAB |
| --- | --- |
| Cardiac troponin I, fast skeletal | 194.0X upregulated |
| Cardiac troponin T3, fast skeletal | 194.0X upregulated |
| MLC, fast skeletal | 3.7X upregulated |
| α skeletal actin | 2.8X upregulated |
| β MHC | 29.8S downregulated |

Figure 9:
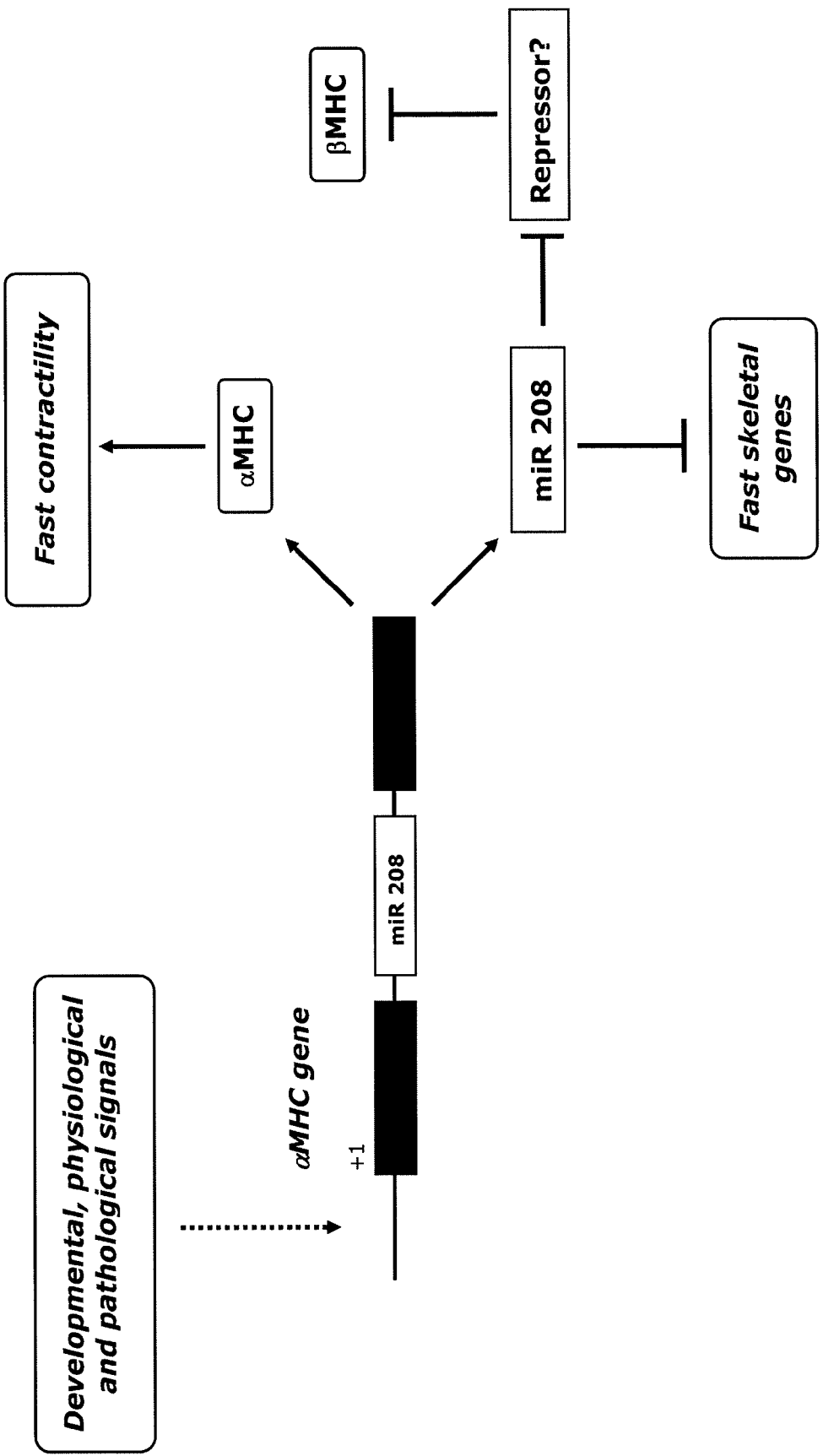
FIG. 9—A model for the role of miR-208 in cardiac gene regulation. The αMHC gene encodes miR-208, which negatively regulates expression of THRAP1 and skeletal muscle genes (and probably additional targets). The α- and βMHC genes are linked and miR-208 is required for up-regulation of βMHC in response to stress signaling and blockade to T3 signaling by PTU. α- and βMHC promote fast and slow contractility, respectively.
Figure 10:
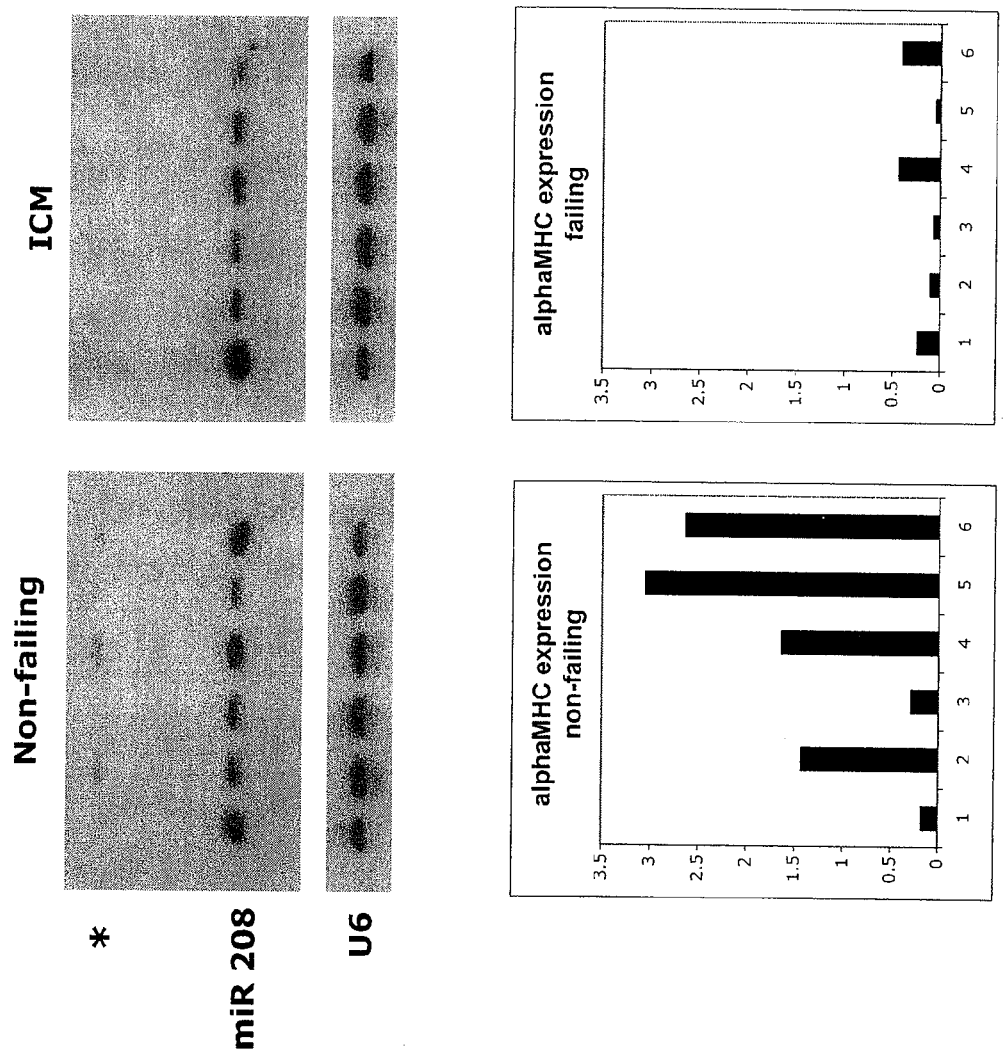
FIG. 10—Human heart samples: non-failing vs. failing.
Figure 13:
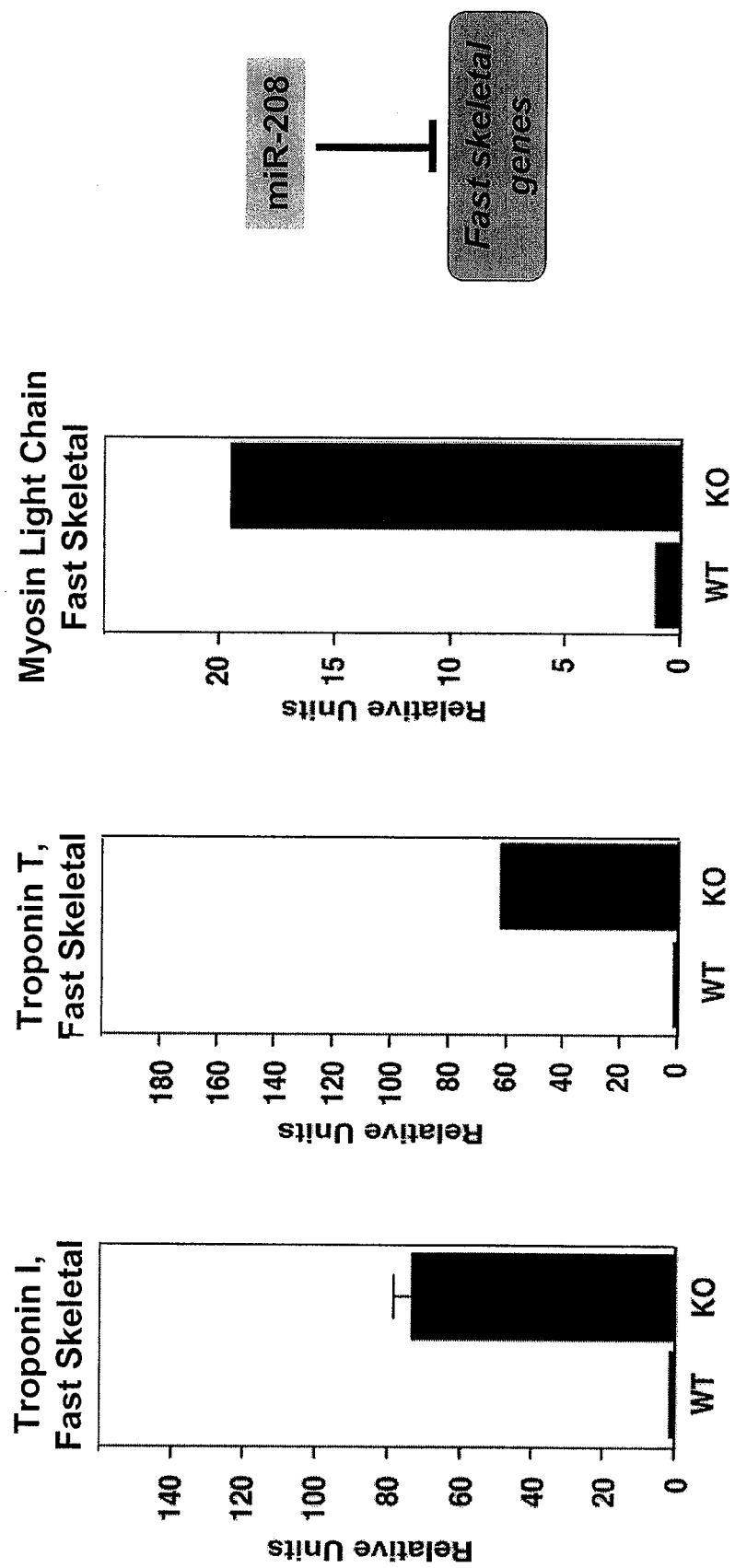
FIG. 13—Up-regulation of fast skeletal muscle genes in hearts of miR-208 mutant mice.

Together, these data indicate that the expression of the α-MHC gene additionally induces the expression of a miRNA that downregulates the expression of the fast skeletal muscle gene program. miR-208 is embedded in the α-MHC gene, which is regulated by developmental, physiological, and developmental signals. α-MHC is a primary determinant of fast contractility. miR-208 represses fast skeletal muscle genes in the heart, such that its deletion results in a dramatic increase in fast skeletal muscle gene expression (FIG. 13). miR-208 is also required to up-regulate β-MHC in the heart. Since microRNAs act as repressors, it is postulated that miR-208 represses a repressor of β-MHC expression as illustrated in FIG. 9. During cardiac stress, this miRNA is responsible for the induction of β-MHC, both at the level of RNA and protein, while in the absence of miR-208 this induction is totally absent and α-MHC remains the sole myosin heavy chain isoform. Analysis of α-MHC expression in failing and non-failing human heart samples showed that α-MHC expression in failing heart was reduced compared to α-MHC expression in non-failing heart (FIG. 10). These data demonstrate that miR-208 is a central regulator in cardiac contractile function and appears to be involved in the maladaptive myosin switching during cardiac disease.

Figure 12:
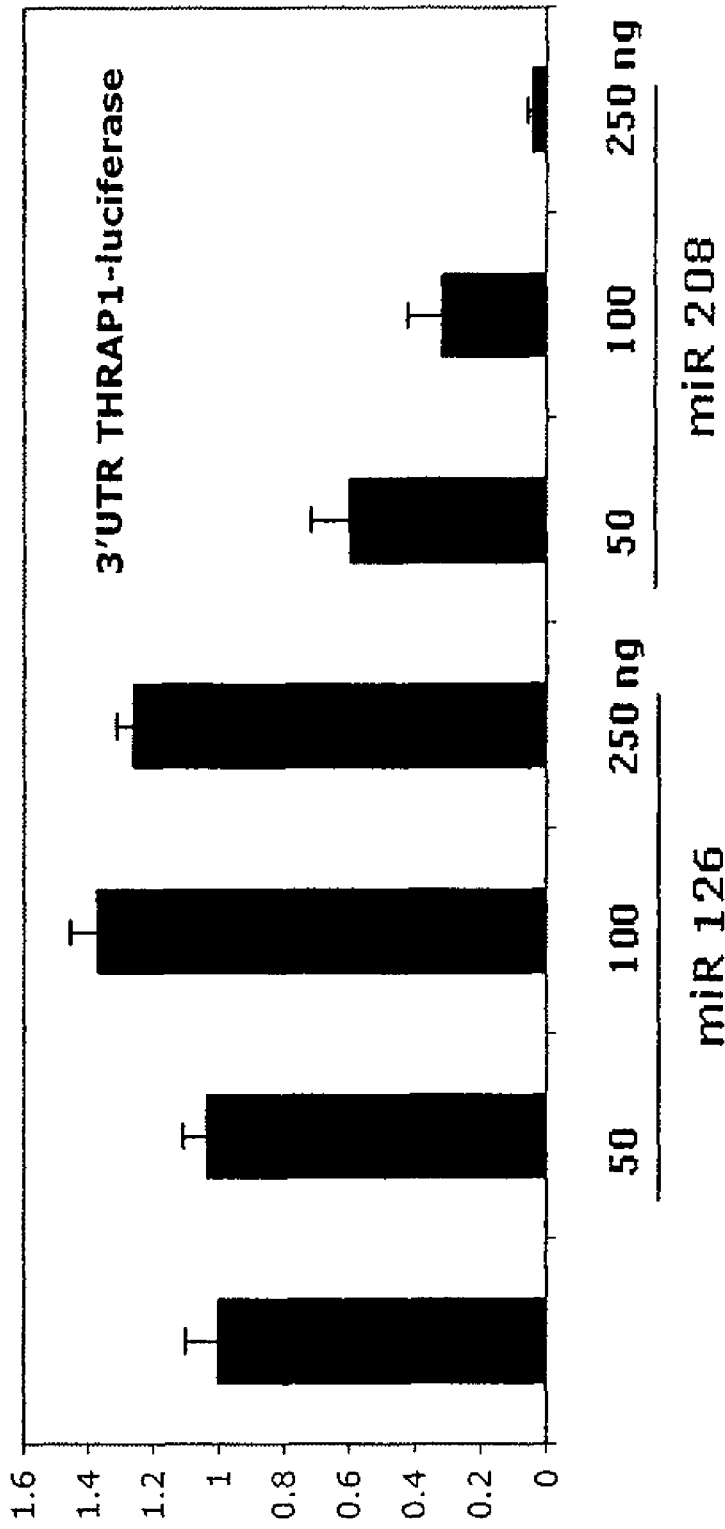

Using the miRanda software (available from the Computational Biology Center at Memorial Sloan-Kettering Cancer Center) and the PicTar algorithm for the identification of miRNA targets (Krek et al., 2005), thyroid hormone receptor associated protein 1 (THRAP1) was identified as a predicted target for miR-208. FIG. 12 shows the alignment of miR-208 with THRAP1 3' UTR sequences from human, chimp, mouse, rat, canine, chicken, fugu, and zebrafish.

miR-208 regulates pathological cardiac remodeling. Mice homozygous for the miR-208 deletion were viable and did not display obvious abnormalities in size, shape or structure of the heart up to 20 weeks of age. To further investigate the potential functions of miR-208, the inventors compared the response of wild-type and miR-208 mutant mice to thoracic aortic banding (TAB), which induces cardiac hypertrophy by increased afterload on the heart and is accompanied by down-regulation of αMHC and up-regulation of βMHC (Hill et al., 2000). αMHC mRNA expression declined as expected following TAB (FIG. 14A), but miR-208 was still abundantly expressed 21 days after TAB (FIG. 14B), consistent with its relatively long half-life.

Figure 14:
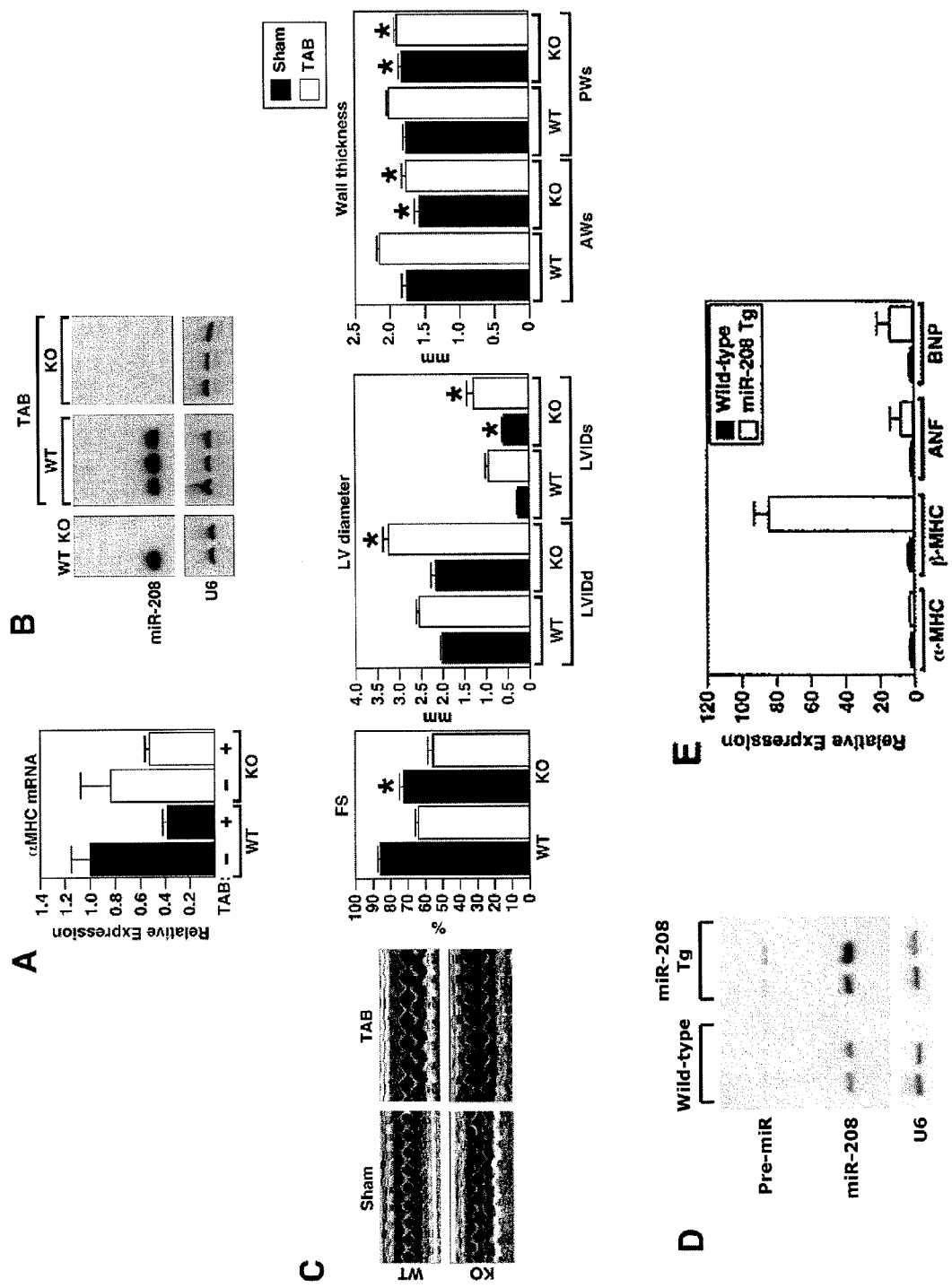
FIGS. 14A-E—Analysis of wild-type and miR-208$^{-/-}$ animals after TAB.
Figure 15:
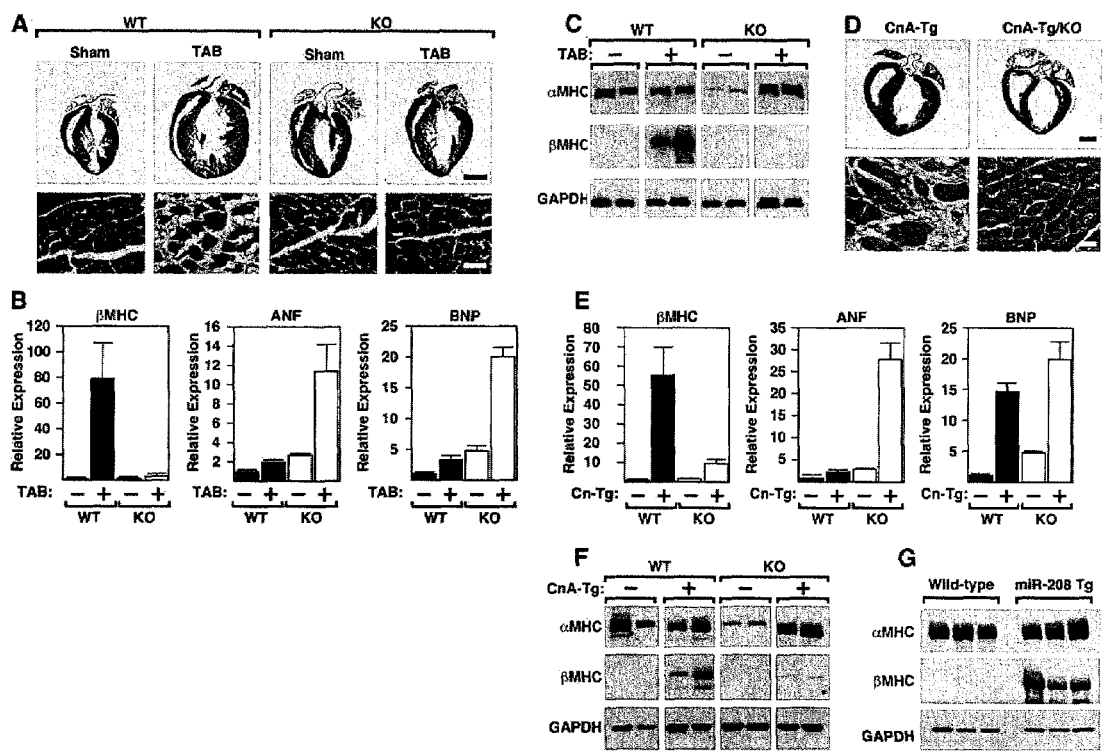
FIGS. 15A-G—MiR-208$^{-/-}$ mice show reduced cardiac hypertrophy in response to pressure overload.

In response to TAB, wild-type mice showed a pronounced increase in cardiac mass accompanied by hypertrophic growth of cardiomyocytes and ventricular fibrosis (FIG. 15A). In contrast, miR-208 mutant animals showed virtually no hypertrophy of cardiomyocytes or fibrosis in response to TAB (FIG. 15A). Echocardiography confirmed that miR-208$^{-/-}$ animals displayed a blunted hypertrophic response and a reduction in contractility (FIG. 14C). Most remarkable, was the inability of mutant animals to up-regulate βMHC. Instead, αMHC protein expression increased in miR-208 mutant hearts in response to TAB, which may reflect a compensatory mechanism to maintain MHC expression in the absence of βMHC up-regulation. Other stress responsive genes, such as those encoding the natriuretic peptides ANF and BNP, were strongly induced in miR-208 mutant animals (FIGS. 15B-C). Microarray analysis on hearts from wild-type and miR-208$^{-/-}$ animals confirmed that the absence of miR-208 resulted in a highly specific block to βMHC expression (Tables 4-5).

TABLE 4

Microarray analysis of cardiac tissue from wild-type and miR-208$^{-/-}$ animals.
Top 20 of genes that are differentially expressed in miR208$^{-/-}$ compared to wild-type animals are shown in each category.

| miR-208 KO | Wild-type | Log | Fold change | Gene |
|---|---|---|---|---|
| \multicolumn{5}{l}{Genes with elevated expression in miR-208 KO animals relative to wild-type animals} |
| 349.1 | 8.3 | 6.3 | 78.8 | Early growth response 2 (Egr2) |
| 7920.4 | 128 | 6.2 | 73.5 | *Mus musculus* proponin I, skeletal, fast 2 (Tnni2), mRNA |
| 731.3 | 9.1 | 5.6 | 48.5 | Early growth response 2 (Egr2) |
| 6298.8 | 135.1 | 5.5 | 45.3 | Heat shock protein, 70 kDa 1 (Hsp 70-1) |
| 4546.4 | 91.9 | 5.3 | 39.4 | Heat shock protein, 70 kDa 3 (Hsp 70-3) |
| 695.3 | 17.6 | 5.2 | 36.8 | *Mus usculus* troponin T3, skeletal, fast (Tnnt3), mRNA |
| 6580.9 | 170.5 | 5.1 | 34.3 | Heat shock protein, 70 kDa 1 (Hsp 70-1) |
| 7772.6 | 360.6 | 4.5 | 22.6 | Heat shock proten, 70 kDa 1 (Hsp 70-1) |
| 4665.2 | 341.7 | 3.9 | 14.9 | *Mus musculus* early growth response 1 (Egr1), mRNA |
| 7909.7 | 119.1 | 3.6 | 12.1 | Troponin I, skeletal, fast 2 (Tnni2) |
| 3490.1 | 339.8 | 3.5 | 11.3 | *Mus musculus* nuclear receptor subfamily 4, group A, member 1 (Nr4a1), mRNA |
| 9451 | 486.7 | 3.5 | 11.3 | *Mus musculus* myosin light chain, alkali, fast skeletal muscle (Mylf) |
| 1206.8 | 171.1 | 3 | 8.0 | FBJ osteosarcoma oncogene (Fos) |
| 1277.2 | 219.9 | 2.8 | 7.0 | Solute carrier family 11 member 1 (natural resistance-associated macrophage protein 1) |
| 586.2 | 103.4 | 2.7 | 6.5 | Activating transcription factor 3 |
| 695.4 | 110.1 | 2.6 | 6.1 | *Mus musculus* parvalbumin (Pva), mRNA |
| 2313.5 | 500.9 | 2.4 | 5.3 | DnaJ (Hsp40) homolog, subfamily B, member 1 |
| 1291.9 | 287.4 | 2.4 | 5.3 | *Mus musculus* pituitary tumor transforming gene protein (PTTG) mRNA, complete cds |
| 174.7 | 30 | 2.3 | 4.9 | Ubiquitin carboxy-terminal hydrolase L1, (Uchl1) |
| 170.4 | 32 | 2.2 | 4.6 | *Mus musculus* osteomodulin (Omd), mRNA |
| \multicolumn{5}{l}{Genes with diminished expression in miR-208 KO animals relative to wild-type animals 3 weeks after TAB} |
| 2.2 | 142.9 | −6.3 | −78.8 | Mouse nuclear-localized inactive X-specific transcript (Xist) mRNA |
| 82.7 | 4674.2 | −5.1 | −34.3 | X (inactive)-specific transcript, antisense |
| 47.7 | 517.5 | −3.5 | −11.3 | *Mus musculus* cytochrome P450, 2a5 (Cyp2a5), mRNA |
| 315.6 | 2607.7 | −3.4 | −10.6 | *Mus musculus* carnitine deficiency-associated gene expressed in ventricle 1 (Cdv1), mRNA |
| 486.9 | 4827.9 | −3.3 | −9.8 | *Mus musculus* carnitine deficiency-associated gene expressed in ventricle 1 (Cdv1), mRNA |
| 34.9 | 205.2 | −3.3 | −9.8 | betaGlcNAc beta 1,3-galactosyltransferase, polypeptide 2 (b3Galt2) |
| 8 | 70.5 | −3.2 | −9.2 | *Mus musculus* cadherin 1 (cdH1), mRNA |
| 23.8 | 129.3 | −2.9 | −7.5 | *Mus musculus* beta globin mRNA, partial cds |
| 32.4 | 196.2 | −2.8 | −7.0 | *Mus musculus* crystallin, beta A4 (Cryba4), mRNA |
| 8.3 | 49.3 | −2.7 | −6.5 | *Mus musculus* high mobility group box protein (sox2) mRNA, complete cds |
| 2.1 | 21.5 | −2.7 | −6.5 | betaGlcNAc beta 1,3-galactosyltransferase, polypeptide 2 (b3Galt2) |
| 225.8 | 1498.4 | −2.7 | −6.5 | *Mus musculus* cytochrome P450, 2f2 (Cyp2f2), mRNA |
| 1294.9 | 8588.1 | −2.7 | −6.5 | *Mus musculus* mRNA for clara cell 10 kD (CC10) protein, (Scgbla1) |
| 421.7 | 4127.3 | −2.6 | −6.1 | *Mus musculus* UGRP1A mRNA, completed ces, (Scgb3a2)/PROD = UGRP1A |
| 90.5 | 434.8 | −2.4 | −5.3 | Potassium voltage-gated channel, Shal-related family, member 2, (Kcnd2) |
| 7.8 | 48.2 | −2.4 | −5.3 | *Mus musculus* TNF-response element binding protein mRNA, completed cds, (Smarca3) |
| 269.3 | 1118.5 | −2.3 | −4.9 | Potassium voltage-gated channel, Shal-related family, member 2 (Kcnd2) |
| 22.4 | 61.2 | −2.2 | −4.6 | Leucine-rich, glioma inactivated 1, (Lgil) |
| 85 | 469.8 | −2.2 | −4.6 | Guanine nucleotide binding protein, alpha 12, (Gna12) |
| 954.7 | 2196.7 | −2.1 | −4.3 | *Mus musculus* heat shock protein 25 kDa 2 (cardiovascular) Hsp25-2), mRNA |

TABLE 5

Microarray analysis of cardiac tissue from wild-type and miR-208−/− animals 3 weeks post-TAB. Top 20 of genes that are differentially expressed in miR208−/− compared to wild-type animals 3 weeks after TAB surgery are shown in each category.

| miR-208 KO | Wild-type | Log | Fold change | Gene |
|---|---|---|---|---|
| \multicolumn{5}{l}{Genes with elevated expression in miR-208 KO animals relative to wild-type animals 3 weeks after TAB} | | | | |
| 7259.6 | 38.8 | 7.6 | 194.0 | *Mus musculus* troponin I, skeletal, fast 2 (Tnni2), mRNA |
| 2455.4 | 11.8 | 7.6 | 194.0 | *Mus musculus* proponin T3, skeletal, fast (Tnnt3), mRNA |
| 249.6 | 1.3 | 7.6 | 194.0 | *Mus musculus* chitinase 3-like 3 (Chi3l3), mRNA |
| 5624.4 | 49.9 | 6.1 | 68.6 | X (inactive)-specific transcript, antisense (Tsix) |
| 4267.5 | 62.9 | 4.6 | 24.3 | Troponin I, skeletal, fast 2 (Tnni2) |
| 427.9 | 31.8 | 3.7 | 13.0 | *Mus musculus* serum amyloid A 3 (Saa3), mRNA |
| 607.4 | 59.9 | 3.2 | 9.2 | *Mus musculus* S100 calcium binding protein A8 (calgranulin A) (S100a8), mRNA |
| 631 | 68.3 | 3 | 8.0 | *Mus musculus* parvalbumin (Pva), mRNA |
| 1023.2 | 195.3 | 2.9 | 7.5 | *Mus musculus* integrian alpha 9 (Itga9), mRNA |
| 553.5 | 51.1 | 2.9 | 7.5 | *Mus musculus* S100 calcium binding protein A9 (calgranulin B) (S100a9), mRNA |
| 1476 | 205.1 | 2.8 | 7.0 | Thrombospondin 1 (Thbs1) |
| 2697.7 | 415.7 | 2.8 | 7.0 | *Mus musculus* calsequestrin 1 (Casq1), mRNA |
| 1172.3 | 173.1 | 2.7 | 6.5 | *Mus musculus* lysyl oxidase (Lox), mRNA |
| 327 | 67.6 | 2.6 | 6.1 | *Mus musculus* chromogranin B (Chgb), mRNA |
| 1488.6 | 241.7 | 2.5 | 5.7 | Procollagen, type III, alpha 1 (Col3a1) |
| 1729.8 | 308.2 | 2.4 | 5.3 | Elastin (Eln) |
| 771.2 | 128 | 2.4 | 5.3 | Synuclein, alpha (Snca) |
| 914.2 | 185.1 | 2.3 | 4.9 | *Mus musculus* latent transforming growth factor beta binding protein 2 (Ltbp2), mRNA |
| 2753.4 | 425.7 | 2.3 | 4.9 | *Mus musculus* serine protease inhibitor 2-2 (Spi2-2), mRNA |
| 1509.5 | 256.9 | 2.3 | 4.9 | Procollagen, type V, alpha 2 (Col5a2) |
| \multicolumn{5}{l}{Genes with diminished expression in miR-208 KO animals relative to wild-type animals 3 weeks after TAB} | | | | |
| 1.4 | 146.5 | −5.9 | −59.7 | Tripartite motif protein 12 (TRIM12) |
| 2.7 | 128.1 | −5.1 | −34.3 | RNA-binding region (RNP1, RRM) containing 2 (Rnpc2) |
| 485.2 | 9966.2 | −4.9 | −29.9 | *Mus musculus* myosin, heavy polypeptide 7, cardiac muscle, beta (Myh7), mRNA |
| 9.8 | 101 | −3.3 | −9.8 | *Mus musculus* jumonji (jmj), mRNA |
| 9.3 | 144.5 | −3.2 | −9.2 | *Mus musculus* small inducible cytokine A11 (Scya11), mRNA |
| 9.9 | 86.9 | −3.1 | −8.6 | *Mus musculus* potassium voltage-gated channel, Isk-related subfamily, member 1 (Kcne1), mRNA |
| 7.5 | 67.1 | −3.1 | −8.6 | Leucine-rich, glioma inactivated 1 (Lgi1) |
| 128.5 | 974.2 | −3.1 | −8.6 | *Mus musculus* pituitary tumor transforming gene protein (PTTG) mRNA, completed cds |
| 300.9 | 2502 | −3.1 | −8.6 | Heat shock protein, 70 kDa 1 (Hsp 70-1) |
| 252.4 | 2016.7 | −3.1 | −8.6 | Heat shock protein, 70 kDa 3 (Hsp 70-3) |
| 7.9 | 133.4 | −3.0 | −8.0 | *Mus musculus* prostaglandin F receptor (Ptgfr), mRNA |
| 423.9 | 3375.9 | −3.0 | −8.0 | Pituitary tumor-transforming 1 (Pttg1) |
| 29.5 | 211.8 | −2.9 | −7.5 | *Mus musculus* glycine C-acetyitransferase (2-amino-3-ketobutyrate-coenzyme A ligase) (Gcat) |
| 388 | 3048.8 | −2.9 | −7.5 | Heat shock protein, 70 kDa 1 (Hsp 70-1) |
| 557.2 | 3734.4 | −2.8 | −7.0 | *Mus musculus* carnitine deficiency-associated gene expressed in ventricle 1 (Cdv1), mRNA |
| 302.6 | 1731.8 | −2.6 | −6.1 | *Mus musculus* carnitine deficiency-associated gene expressed in ventricle 1 (Cdv1), mRNA |
| 49.3 | 211.2 | −2.5 | −5.7 | Kidney androgen regulated protein (Kap) |
| 12.3 | 56.6 | −2.5 | −5.7 | *Mus musculus* serine hydroxymethyltransferase mRNA, complete cds |
| 42 | 224.8 | −2.5 | −5.7 | Macrophage activation 2 (Mpa2) |
| 30.3 | 165.1 | −2.4 | −5.3 | Peroxisome proliferative activated receptor, gamma, coactivator 1 (Ppargc1) | miR-208−/− mice were also resistant to fibrosis and cardiomyocyte hypertrophy in response to transgenic expression of activated calcineurin (FIG. 15D), an especially powerful stimulus for cardiac hypertrophy and heart failure. Similarly, βMHC mRNA and protein failed to be up-regulated in hearts of miR-208−/−; CnA-Tg mice at 6 weeks of age, whereas ANF and BNP were strongly induced (FIGS. 15E-F). Thus, miR-208 is necessary for up-regulation of βMHC and cellular remodeling, but not for expression of other markers of cardiac stress.

To test whether miR-208 was sufficient for up-regulation of βMHC expression, the inventors generated transgenic mice that over-expressed miR-208 under control of the αMHC promoter. αMHC-miR-208 transgenic mice were viable and expressed miR-208 at a level ~3-fold above that of wild type hearts (FIG. 14D). Hearts from a transgenic line representing the average overexpression of the transgene, showed no overt signs of pathological remodeling at 2 months of age but, remarkably, displayed a dramatic up-regulation of βMHC expression (FIG. 15G and FIG. 14E). This activity of miR-208 was specific, as transgenic overexpression of miR-214, which is induced during cardiac hypertrophy, had no effect on βMHC expression. Given that the endogenous level of miR-208 in the adult mouse heart is insufficient to up-regulate βMHC expression, the finding that a 3-fold increase in miR-208 expression in these transgenic mice results in up-regulation of βMHC expression suggests that there is a sharp threshold for the control of βMHC expression by this microRNA.

Figure 16:
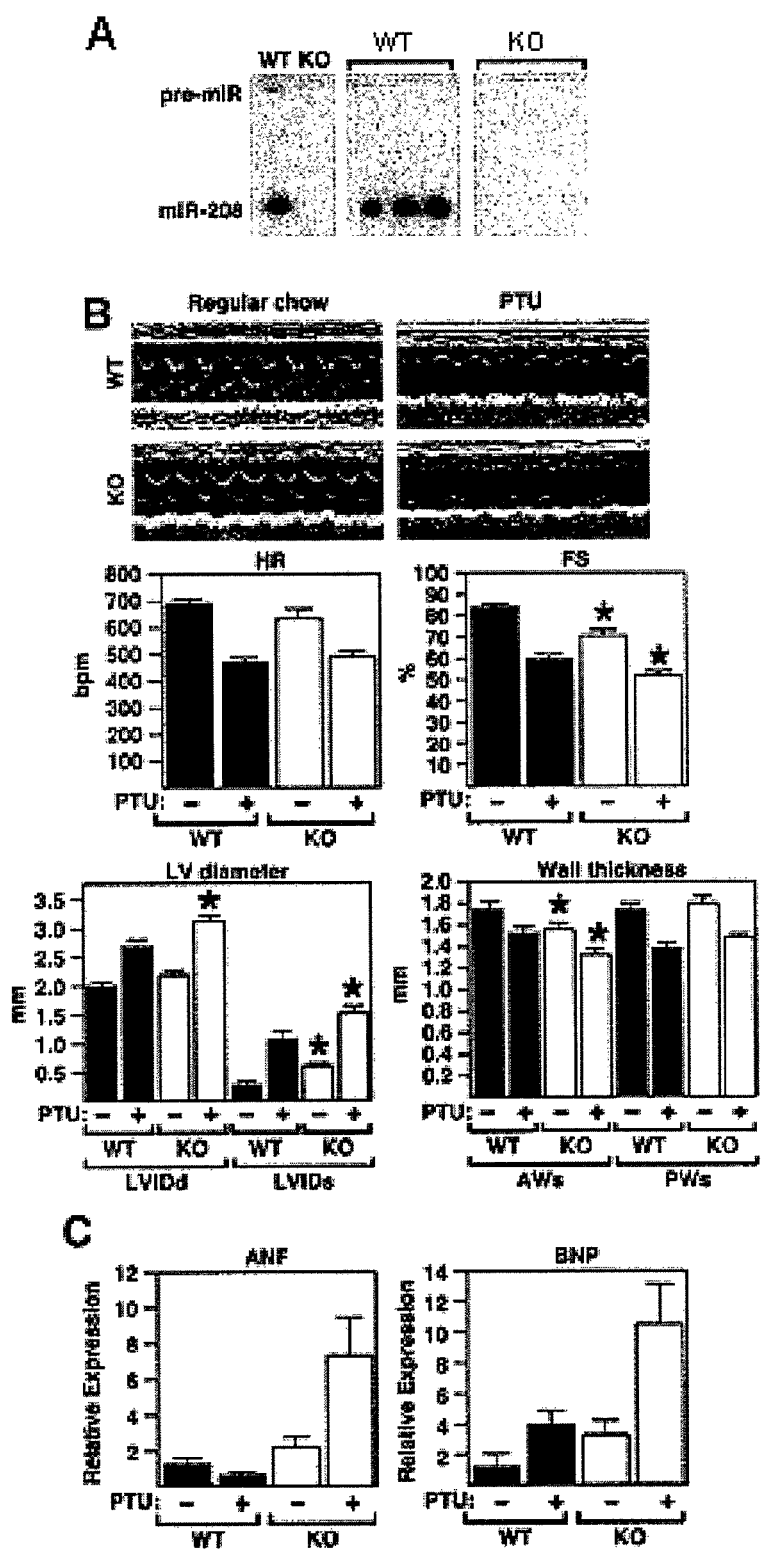
FIGS. 16A-C—Analysis of wild-type and miR-208$^{-/-}$ animals after PTU treatment.
Figure 17:
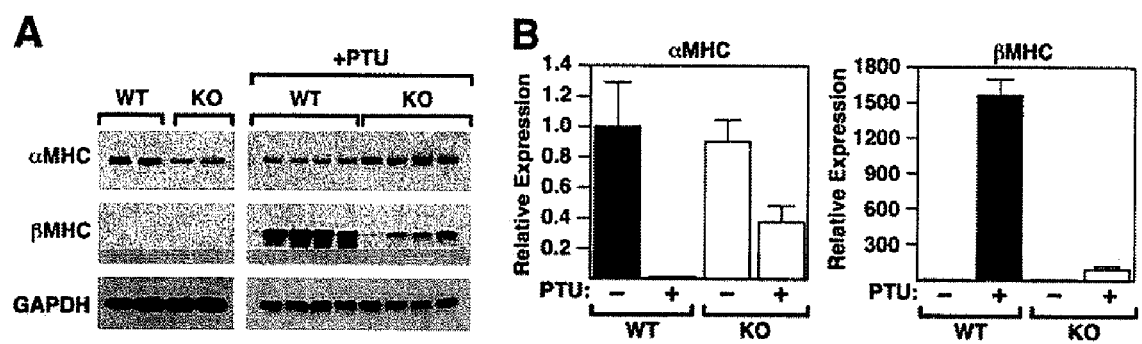
FIGS. 17A-B—Regulation of thyroid hormone responsiveness of the βMHC gene by miR-208.

MiR-208 regulates T3-dependent repression of βMHC. T3 signaling induces αMHC transcription via a positive T3 response element (TRE), whereas a negative TRE in the promoter of the βMHC gene mediates transcriptional repression (Ojamaa et al., 2000). To test whether miR-208 was required for T3-dependent regulation of 8iMHC, mutant and wild-type littermates were fed PTU-containing chow for 2 weeks to block T3 signaling. Northern blot analysis verified miR-208 to be abundantly present after 2 weeks of PTU treatment (FIG. 16A). PTU, as expected, induced a decline in heart rate and contractility and an increase in dilation, with no striking differences between wild-type and mutant animals (FIG. 16B). However, whereas wild-type animals showed the expected decrease in α- and increase in βMHC in response to PTU, the miR-208$^{-/-}$ animals again appeared resistant to up-regulation of βMHC, although a trace of βMHC expression was detectable (FIGS. 17A-B). ANF and BNP were up-regulated by PTU in miR-208$^{-/-}$ animals, confirming the specific role of miR-208 in βMHC expression (FIG. 16C). Since PTU induces the α- to βMHC isoform switch by interfering solely with thyroid hormone receptor (TR) signaling, these findings suggest that miR-208 potentiates βMHC expression through a mechanism involving the TR.

Figure 18:
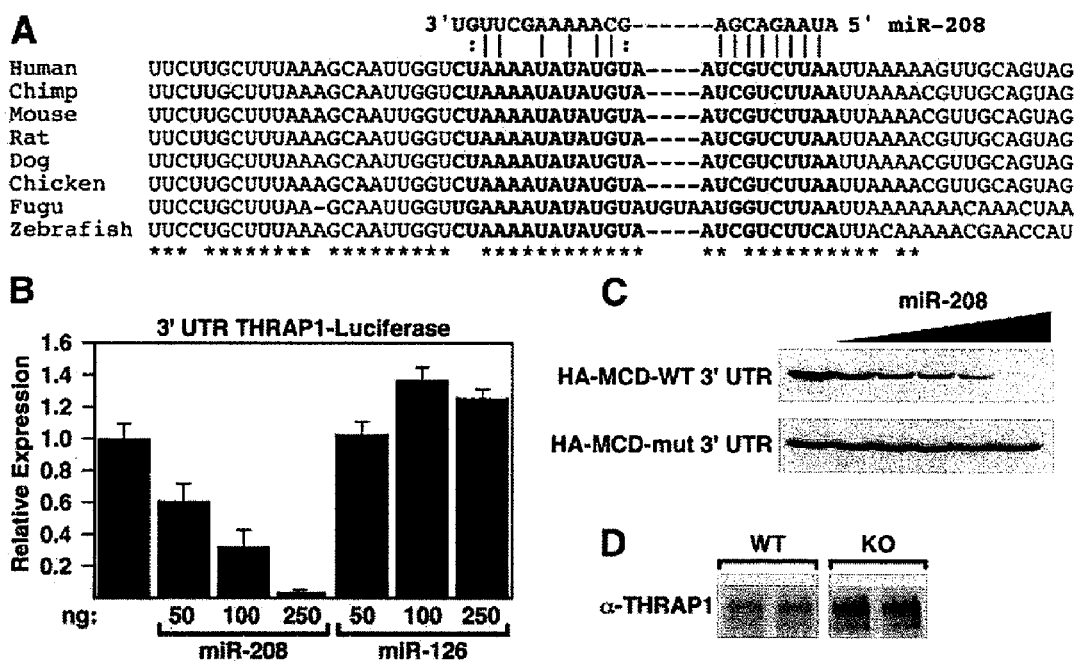
(FIG. 18) COS1 were transfected with either HA-MCD-WT UTR or HA-MCD-mutated UTR along with increasing dosages of pCMV-miR-208 ranging from 0.1-2 μg. HA-levels were detected using immunoblot.

MiR-208 targets TR Associated Protein 1. Among the relatively few predicted targets of miR-208, the mRNA encoding thyroid hormone receptor Associated Protein 1 (THRAP1), also known as TRAP240, scored as the strongest predicted target with the PicTar target prediction program (Krek et al., 2005). THRAP1, a component of the TR-associated TRAP complex, modulates activity of the TR by recruitment of RNA polymerase II and general initiation factors (Ito and Roeder, 2001). The putative miR-208 binding site in the 3'-UTR of the THRAP1 mRNA showed high complementarity with the 5' arm of miR-208, the most critical determinant of miRNA targeting, as well as evolutionary conservation (FIG. 18A). Based on the imperfect complementarity of miR-208 and THRAP1 3'-UTR sequence, miR-208 would be expected to inhibit translation of THRAP1.

Figure 19:
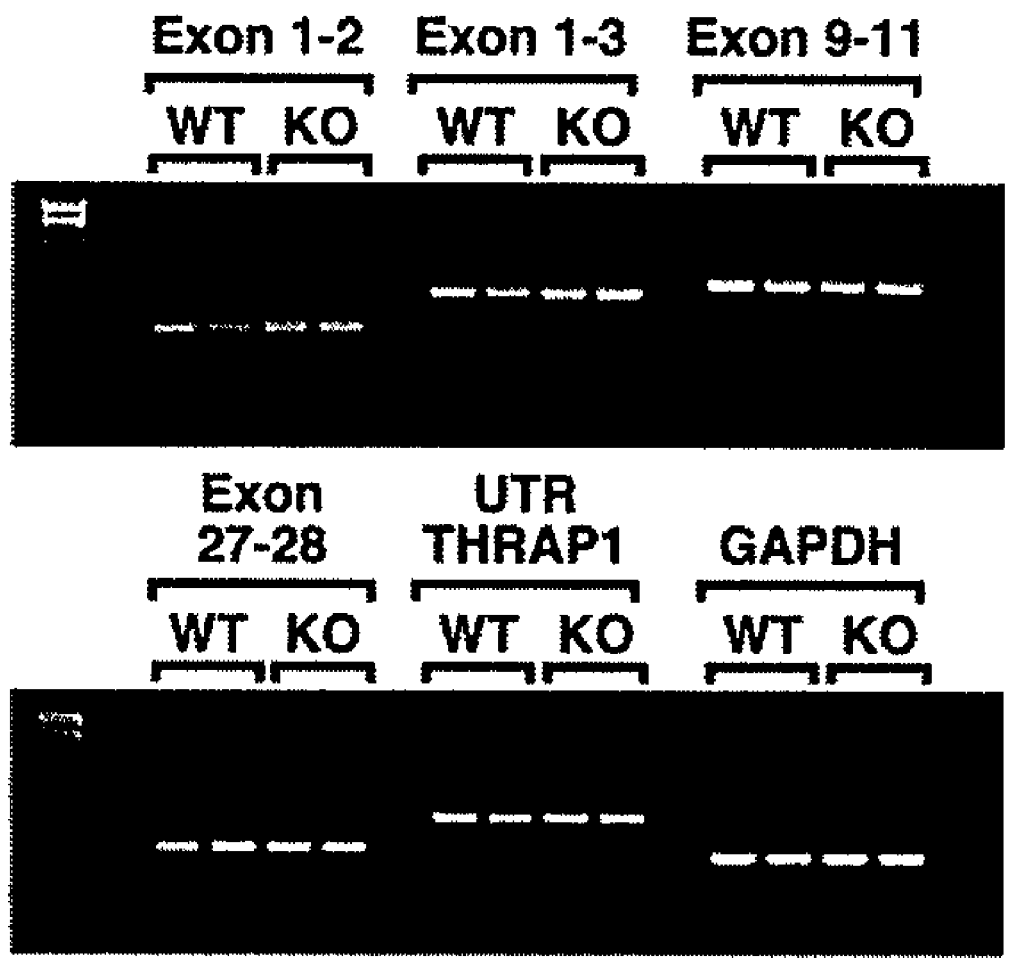
FIG. 19—RT-PCR analysis of THRAP1 transcripts. Analysis of THRAP1 transcripts by RT-PCR of RNA from hearts of mice of from wild-type and miR-208$^{-/-}$ mice. Positions of primers in mRNA transcript are indicated.
Figure 21:
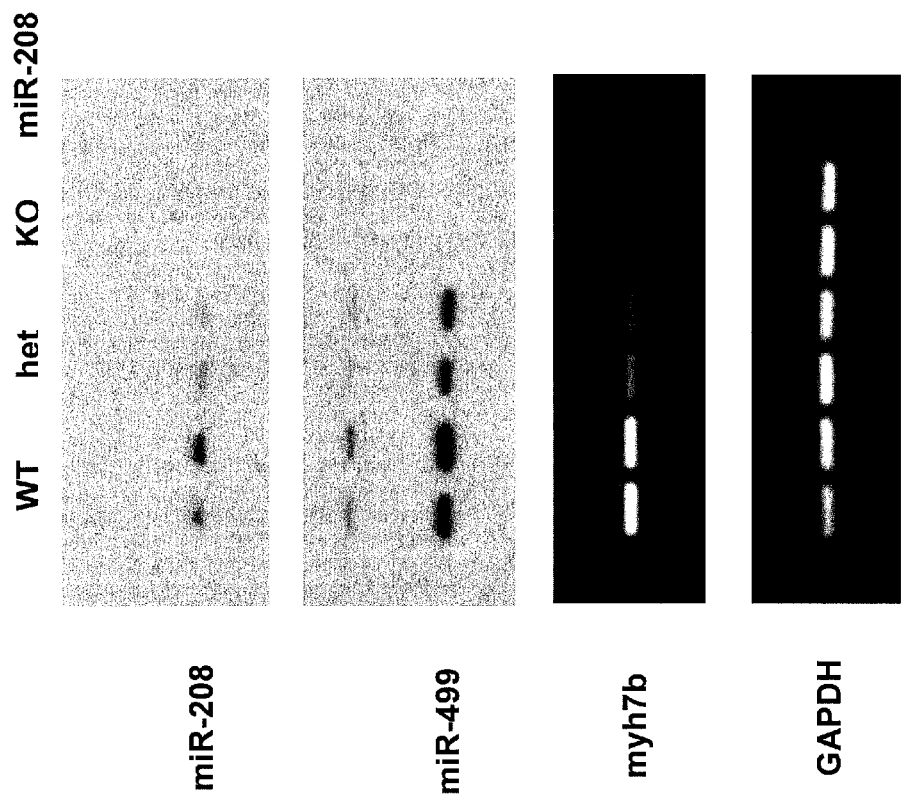
FIG. 21—Northern blot showing expression of miR-499 in hearts of wild type, miR-208$^{+/-}$ and miR-208$^{-/-}$ mice. There is a direct correlation between the expression of miR-208 and miR-499, as well as Myh7b in wild-type and mutant mice.

To test whether the putative miR-208 target sequence in the THRAP1 3'-UTR could mediate translational repression, the inventors inserted the full length 3'-UTR of the THRAP1 transcript into a luciferase expression plasmid, which was transfected into COS1 cells. Increasing amounts of CMV-driven miR-208 resulted in a dose-dependent decrease in luciferase activity, while comparable amounts of miR-126, as a control, had no effect (FIG. 18B). CMV-miR-208 also dose-dependently abrogated translation of an HA-tagged malonyl CoA decarboxylase (MCD) expression cassette linked to the THRAP1 3' UTR binding sequence, but not a mutant miR-208 target sequence (FIG. 18C). In addition, THRAP1 protein expression was increased in cardiac protein lysates from miR-208$^{-/-}$ mice compared to wild-type littermates (FIG. 18D), whereas THRAP1 mRNA was comparable in hearts of the two genotypes (FIG. 19), consistent with the conclusion that miR-208 acts as a negative regulator of THRAP1 translation in vivo. Under situations of stress, the negative influence of miR-208 on THRAP1 protein expression may be even greater, in light of recent studies showing that stress augments repressive actions of miRNAs by promoting their association of miRNAs with Argonaute (Leung et al., 2006).

miR-208 is required for expression of miR-499. To further explore the mechanism of action of miR-208 in the heart, the inventors defined the microRNA expression patterns in hearts from wild type and miR-208 null mice by microarray analysis. Among several microRNAs that were up- and down-regulated in mutant hearts, the inventors discovered that miR-499 was highly abundant in normal hearts, but was not expressed above background levels in miR-208 mutants. These findings were confirmed by Northern blot (FIG. 21).

Figure 23:
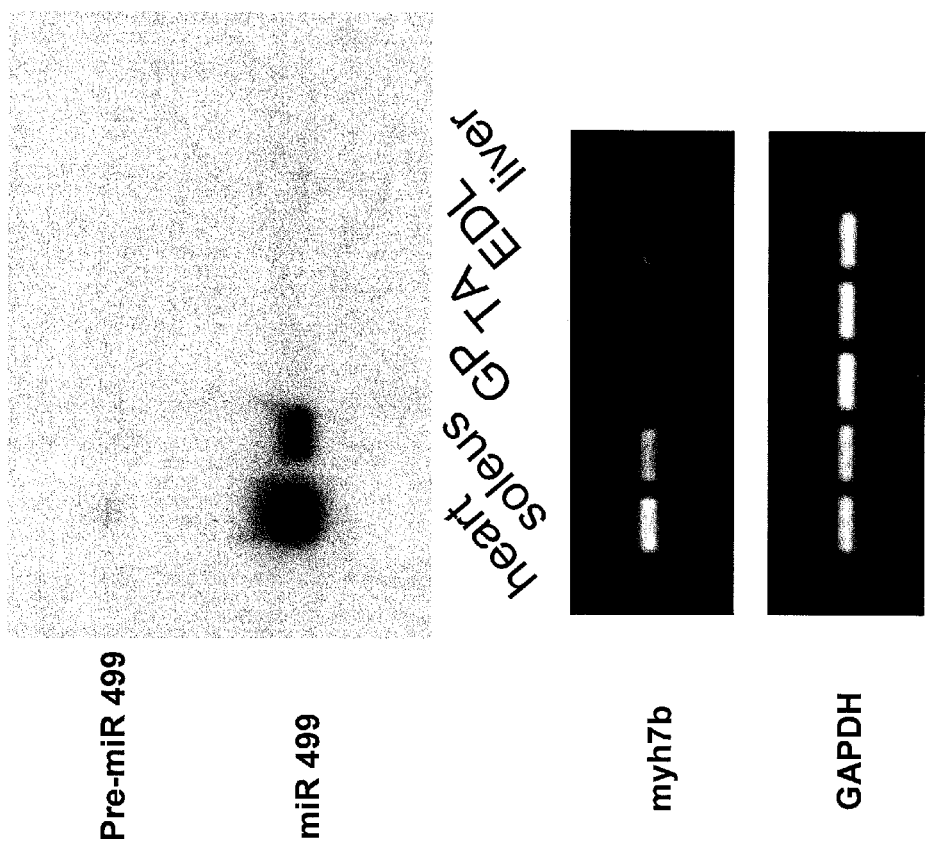
FIG. 23—RNA blot showing expression of miR-499 in heart and soleus. Mir-499 is not expressed in fast skeletal muscle fibers such as gastrocnemius/plantaris (GP), tibialis anterior (TA) or extensor digitorum longus (EDL).

Analysis of the genomic location of the miR-499 gene showed it to be contained within the 20$^{th}$ intron of the Myh7b gene, a homolog of the alpha-Mhc gene (Myh7b) (FIG. 22). The Myh7b gene is conserved in vertebrates and is expressed solely in the heart and slow skeletal muscle (soleus) (FIG. 23). In addition, miR-499 is down-regulated during cardiac hypertrophy (FIG. 24).

MEF2 regulates miR-499 expression in cardiac and skeletal muscle. Within the 5' flanking region of the Myh7 gene, the inventors identified a potential MEF2 consensus sequence that was conserved across species. This sequence bound MEF2 avidly in gel mobility shift assays, and mutation of this sequence abolished expression of a lacZ reporter in transgenic mice. The MEF2 site was juxtaposed to a conserved E-box sequence (CANNTG), which serves as a binding site for members of the MyoD family of bHLH proteins that drive skeletal muscle gene expression with MEF2. Indeed, MyoD together with the ubiquitous bHLH protein E12 bound the E-box from the promoter. Mutation of this sequence prevented expression of the lacZ transgene in skeletal muscle, but did not affect expression in the heart.

Target ID. Together, the data reported here indicate that the MEF2-regulated expression of the Myh7b gene additionally induces the expression of a slow muscle and cardiac specific miRNA that down-regulates the expression of the fast skeletal muscle gene program. These data provide evidence for miRNA 499 as a central regulator in skeletal muscle fiber type.

MiR-208 is highly homologous to miR-499 and, the remarkable fact that both microRNAs are encoded by introns of Mhc genes, suggests that they share common regulatory mechanisms. Since miRNAs negatively influence gene expression in a sequence specific manner, the high degree of homology predisposes miR-208 and miR-499 to exert comparable functions due to overlap in target genes. The inventors have identified transcriptional regulators of Mhc expression that appear to serve as targets of miR-499. They have also shown that miR-499 expression is controlled by miR-208 in the heart, such that knockdown of miR-208 eliminates miR-499 expression.

Figure 25:
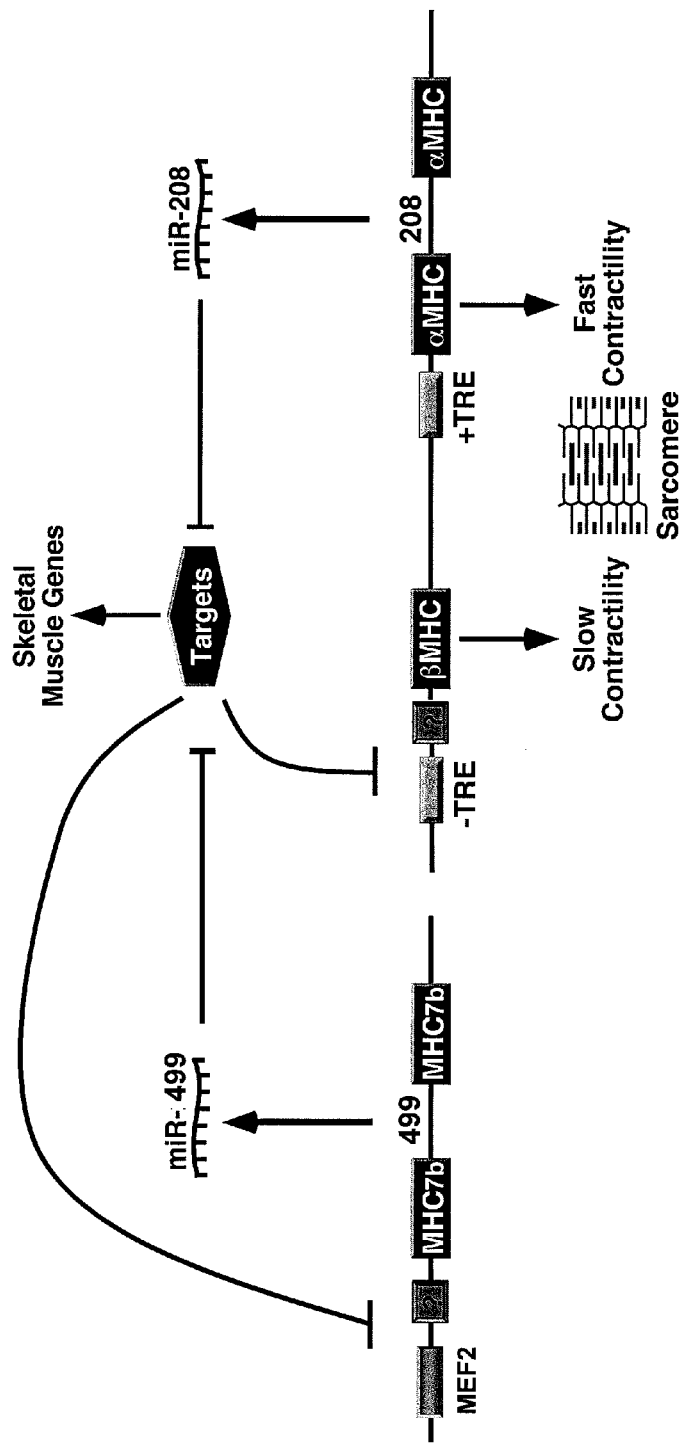
FIG. 25—Schematic diagram of the regulation of miR-499 (SEQ ID NO. 30) by miR-208 (SEQ ID NO. 29) in cardiac muscle.

Since the inventors' previous data demonstrated that genetic disruption of miR-208 leads to strong induction of specifically fast skeletal muscle genes in the heart, it is likely that miR-499 has a comparable function in skeletal muscle and could act as a dominant regulator of fiber type. In line with this hypothesis, promoter analysis of this transcript indicates that the expression of miR-499 and its host transcript are regulated by the myogenic transcription factor MEF2, a central regulator of skeletal muscle fiber type and slow fiber gene expression. The inventors have shown that MEF2 activity promotes muscle endurance and prevents muscle fatigue following prolonged exercise. Thus, they propose that these actions of MEF2 are dependent, at least in part, on the direct activation of miR-499 expression (FIG. 25)

Together, these data indicate that the MEF2-regulated expression of the Myh7b gene additionally induces the expression of a slow muscle and cardiac specific miRNA that downregulates the expression of the fast skeletal muscle gene program. The data provide evidence for miRNA 499 as a central regulator in skeletal muscle fiber type. The remarkable fact that miR-208 and -499 are highly homologous and are both encoded by introns of Mhc genes suggests that they share common regulatory mechanisms. Since miRNAs negatively influence gene expression in a sequence specific manner, the high degree of homology predisposes miR-208 and miR-499 to exert comparable functions due to overlap in target genes. The inventors have identified transcriptional regulators of Mhc expression that appear to serve as targets of miR-499, and they also have shown that miR-499 expression is controlled by miR-208 in the heart, such that knockdown of miR-208 eliminates miR-499 expression.

Figure 26C:
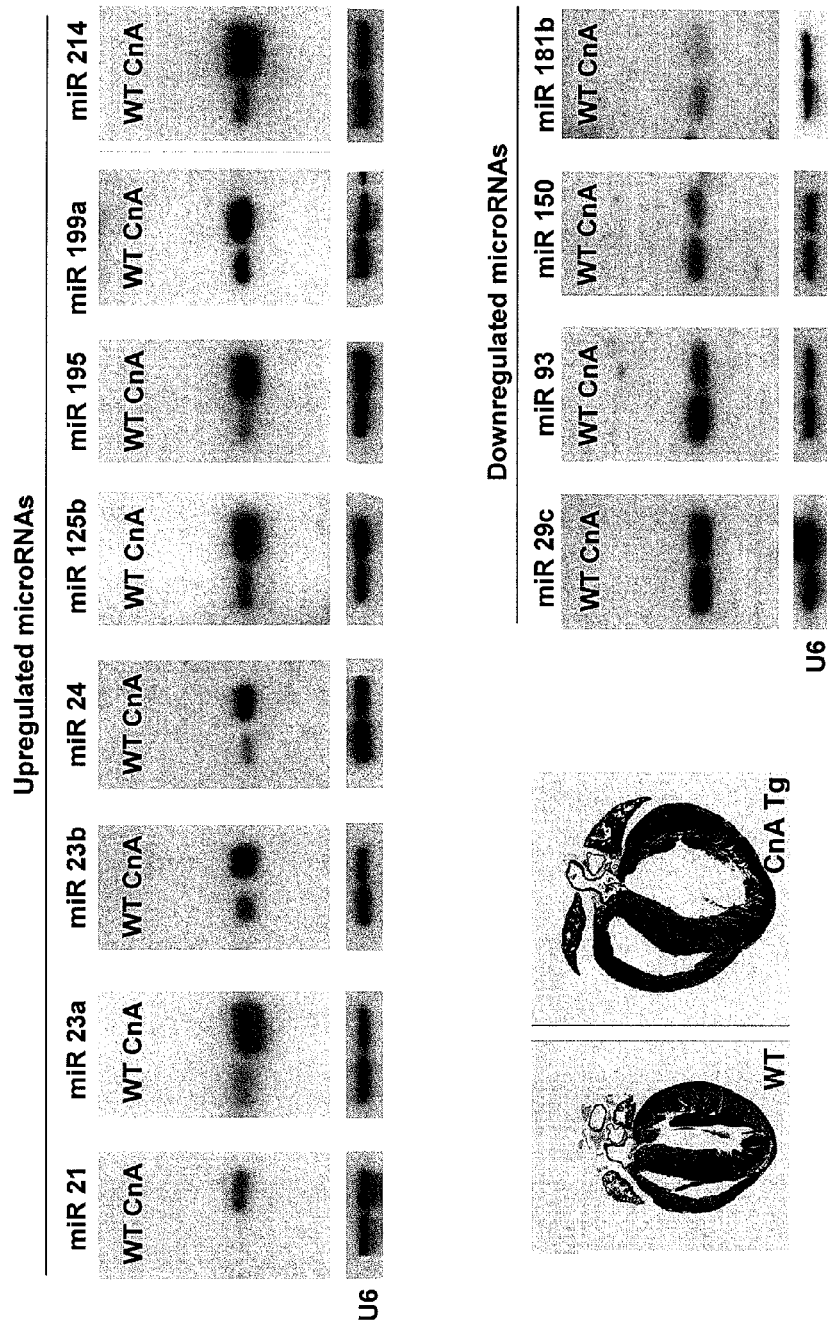

Regulation of cardiac hypertrophy and heart failure by stress-responsive miRNAs. In light of their involvement in modulating cellular phenotypes, we hypothesized that miRNAs might play a role in regulating the response of the heart to cardiac stress, which is known to result in transcriptional and translational changes in gene expression. To investigate the potential involvement of miRNAs in cardiac hypertrophy, the inventors performed a side-by-side miRNA microarray analysis in 2 established mouse models of cardiac hypertrophy, using a microarray that represented 186 different miRNAs (Babak et al., 2004). Mice that were subjected to thoracic aortic banding (TAB), which induces hypertrophy by increased afterload on the heart (Hill et al., 2000), were compared to sham operated animals. In a second model, transgenic mice expressing activated calcineurin (CnA) in the heart, which results in a severe, well-characterized form of hypertrophy (Molkentin et al., 1998), were compared to wild-type littermates (FIG. 26A). RNA isolated from hearts of mice subjected to TAB showed increased expression of 27 miRNAs compared to sham-operated controls, and CnA Tg mice showed increased expression of 33 miRNAs compared with non-transgenic littermate controls, of which 21 were up-regulated in both models. Similarly, TAB and CnA-induced hypertrophy were accompanied by reduced expression of 15 and 14 miRNAs, respectively, of which 7 miRNAs were down-regulated in common (FIG. 26B). Northern analysis of these miRNAs (our unpublished data) and previous microarray analyses (Barad et al., 2004; Sempere et al., 2004; Shingara et al., 2005; Liu et al., 2004) indicate that they are expressed in a wide range of tissues. Based on their relative expression levels, conservation of human, rat and mouse sequences, and levels of expression during hypertrophy, the inventors focused on 11 up- and 5 down-regulated miRNAs (FIG. 26C).

Figure 27:
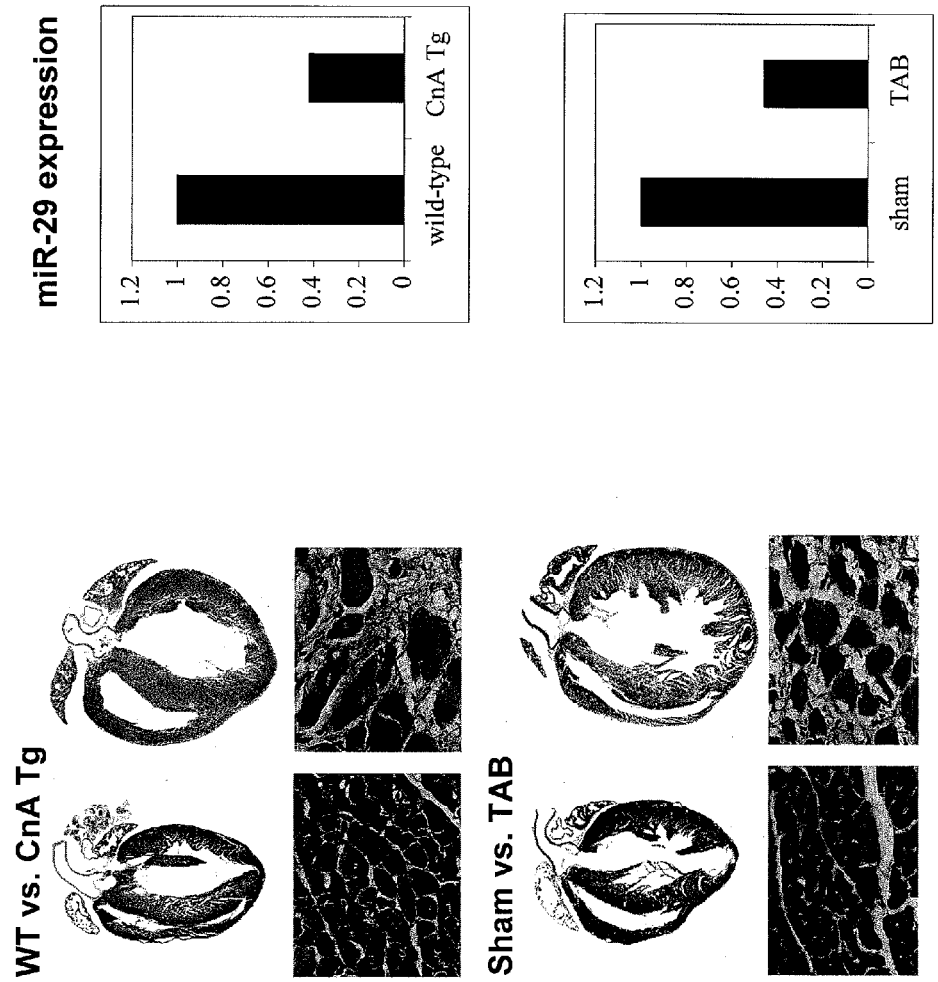
FIG. 27—MiR-29 expression is down-regulated in response to cardiac stress. Hearts from wild-type mice (WT) and mice with hypertrophy and fibrosis induced by a calcineurin transgene (CnA) or TAB are shown on the left. The relative level of expression of miR-29 in each type of heart is shown on the right.
Figure 28:
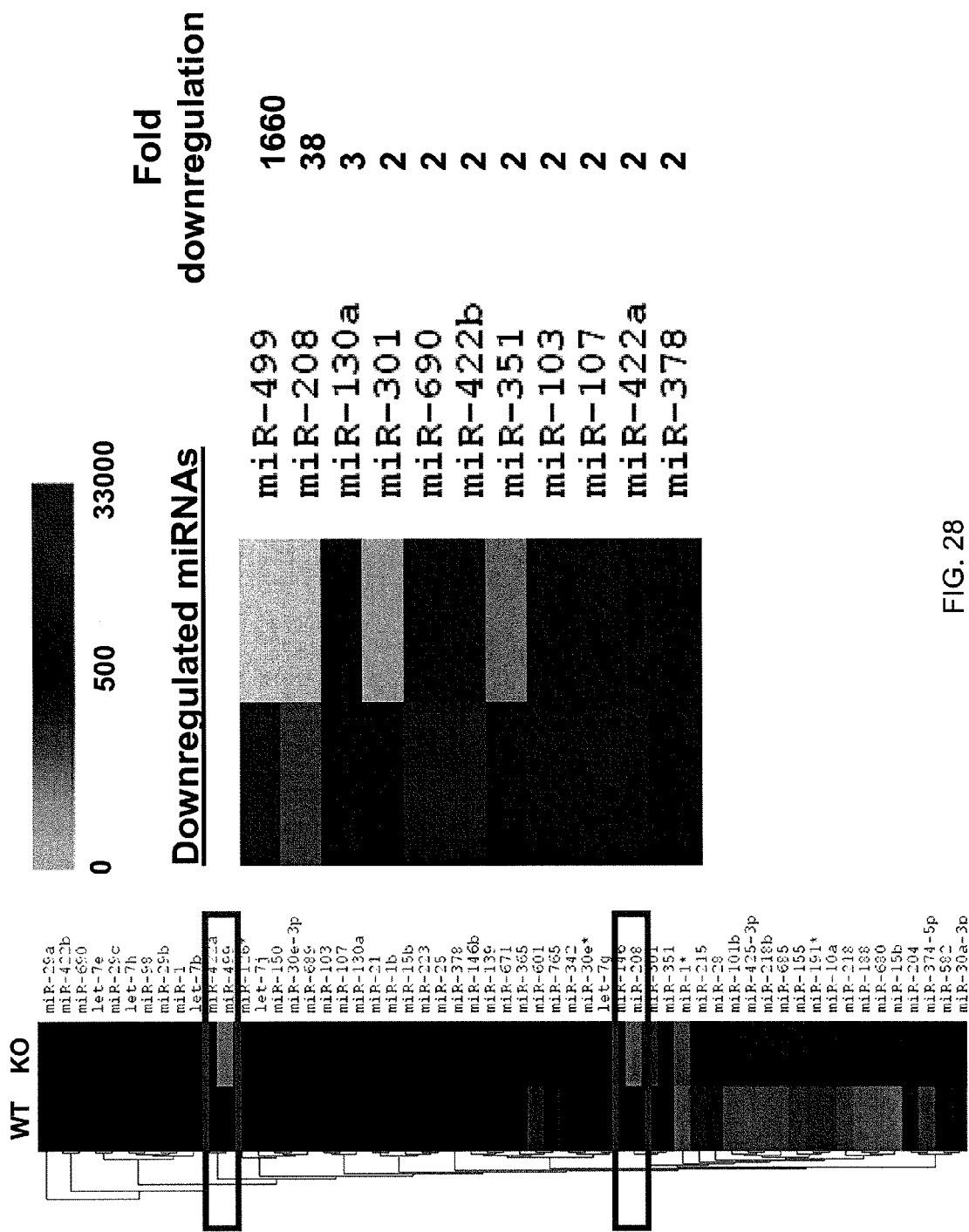
FIG. 28—Microarray analysis of hearts from miR-208 knockout mice compared to wild-type. Microarray analysis was performed on mRNA isolated from wild-type and miR-208 null hearts at 6 weeks of age. The most down-regulated miRNA, next to miR-208, is miR-499.
Figure 29:
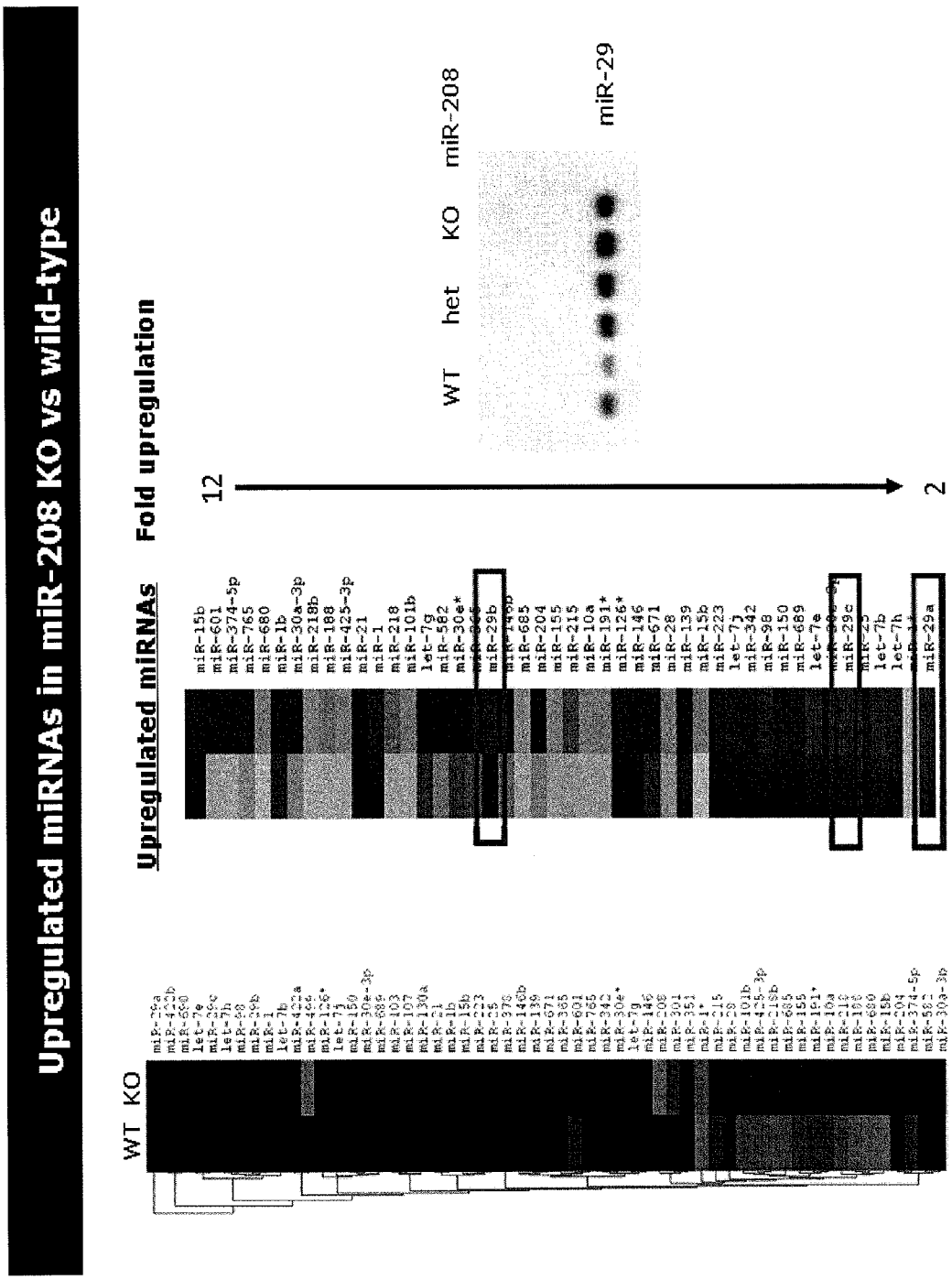
FIG. 29—MiR-29 family is dramatically up-regulated in miR-208 null hearts.
Figure 30:
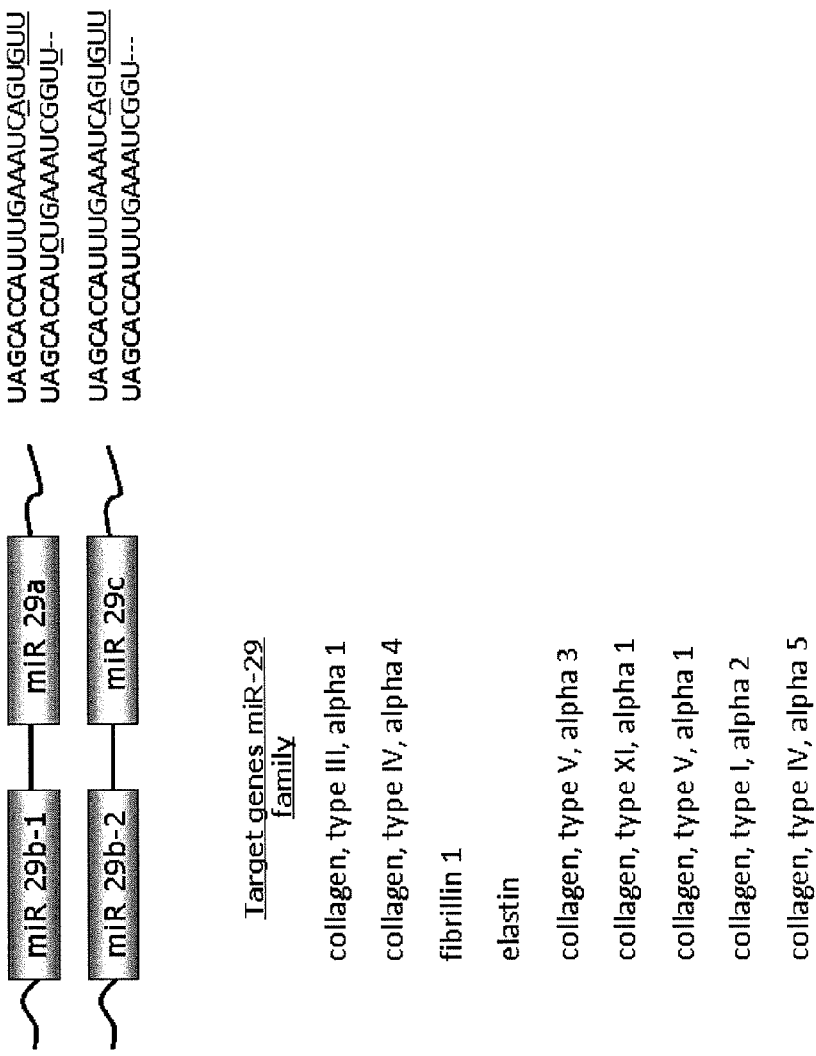
FIG. 30—miR-29 (SEQ ID NOS. 31-34) family targets mRNAs encoding collagens and other components of the extracellular matrix involved in fibrosis.
Figure 31:
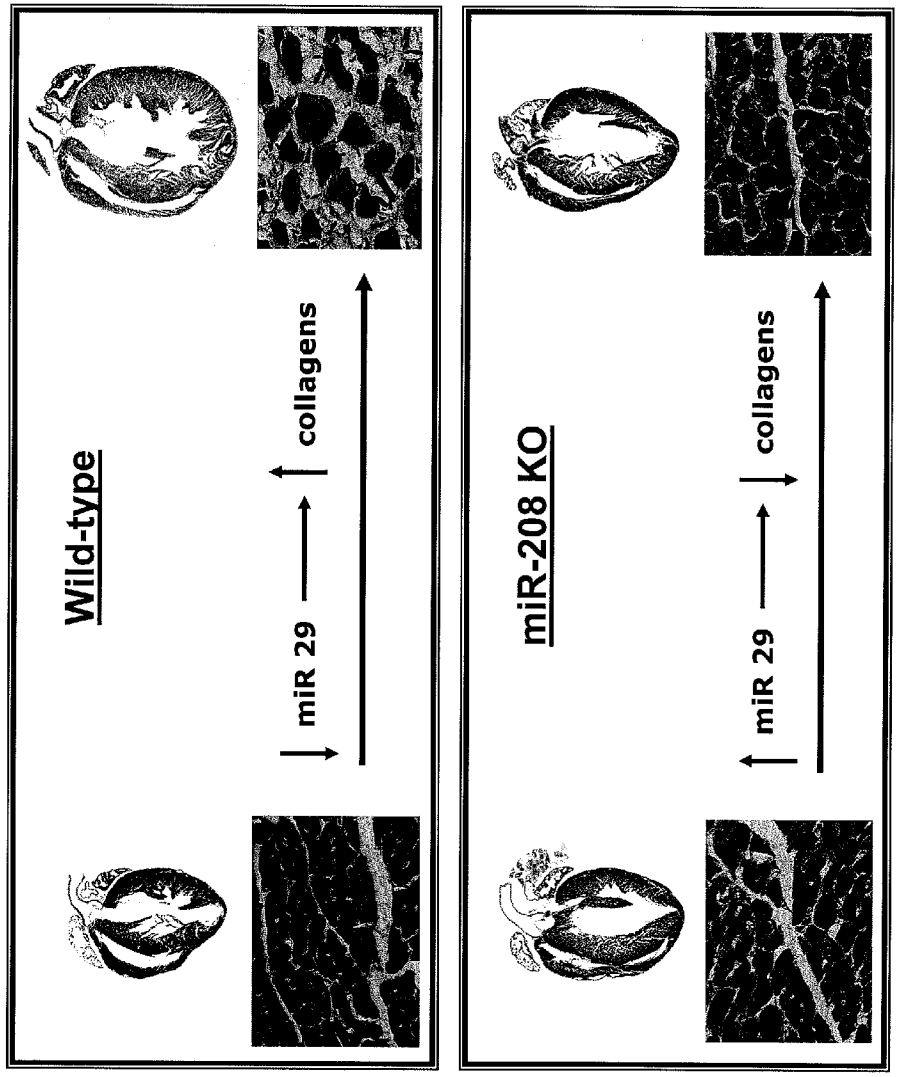
FIG. 31—Model for the control of cardiac fibrosis by miR-208 and miR-29 family. In the normal heart, miR-208 inhibits the expression of miR-29. In the absence of miR-208, miR-29 expression is up-regulated, preventing the expression of extracellular matrix and fibrosis in response to stress. The functions of miR-208, -499 and -29 are interlinked. Loss of miR-208 can be cardioprotective by preventing expression of miR-499 and up-regulating expression of miR-29, with consequent blockade to fibrosis.

Northern blot analysis of cardiac RNA from WT and CnA Tg animals confirmed an increased expression of miRs-21, -23, -24, -125b, -195, -199a, and -214, and decreased expression of miRs-29c, -93, -150 and -181b (FIG. 26C and FIG. 27). Collectively, these data indicate that distinct miRNAs are regulated during cardiac hypertrophy, suggesting the possibility that they might function as modulators of this process.

miR-29 family as down-stream targets for regulation by miR-208. The inventors performed a miRNA microarray on hearts from wild-type and miR-208 null mice in an effort to identify downstream miRNAs that might mediate the actions of miR-208 (FIG. 28). They discovered that multiple members of the miR-29 family were up-regulated in miR-208 null mice (FIG. 29). Target prediction indicated that miR-29 family members targeted mRNAs encoding multiple collagens and other components of the extracellular matrix (FIG. 30). Thus, the upregulation of miR-29 family members in miR-208 null mice is likely to account for the block to fibrosis seen in these animals (FIG. 31).

Summary. The discovery that miR-29 is down-regulated in the diseased heart and targets mRNAs encoding collagens and extracellular matrix proteins suggests that strategies to enhance expression of miR-29 or its association with target mRNAs are likely to have beneficial effects on the heart in the settings of pathological cardiac remodeling and fibrosis. Moreover, elevation of miR-29 expression or function are likely to prevent fibrosis associated with many diseases in tissues such as liver, lung, kidney and others. In addition, the discovery that miR-208 represses miR-29 expression, and that loss of miR-208 upregulates miR-29 expression, indicates that miR-29 is a downstream mediator of the actions of miR-208 on the heart.

Example 3

Discussion

These results demonstrate that miR-208, which is encoded by an intron of the αMHC gene, regulates stress-dependent cardiomyocyte growth and gene expression. In the absence of miR-208, the expression of βMHC is severely blunted in the adult heart in response to pressure overload, activated calcineurin, or hypothyroidism, suggesting that the pathways through which these stimuli induce βMHC transcription share a common miR-208-sensitive component (FIG. 9). In contrast, βMHC expression was unaltered in the hearts of newborn miR-208$^{-/-}$ mice, demonstrating that miR-208 participates specifically in the mechanism for stress-dependent regulation of βMHC expression.

A clue to the mechanism of action of miR-208 comes from the resemblance of miR-208-/- hearts to hyperthyroid hearts, both of which display a block to βMHC expression, up-regulation of stress-response genes (Wei et al., 2005; Pantos et al., 2006), and protection against pathological hypertrophy and fibrosis (Yao and Eghbali, 1992; Chen et al., 2000). The up-regulation of fast skeletal muscle genes in miR-208$^{-/-}$ hearts also mimics the induction of fast skeletal muscle fibers in the hyperthyroid state (Vadaszova et al., 2004). T3 signaling represses βMHC expression in the post-natal heart, and PTU, which causes hypothyroidism, induces βMHC (Morkin, 2000; Schuyler and Yarbrough, 1990). The inability of PTU to induce βMHC expression in miR-208$^{-/-}$ hearts further implicates miR-208 in the T3 signaling pathway.

Figure 20:
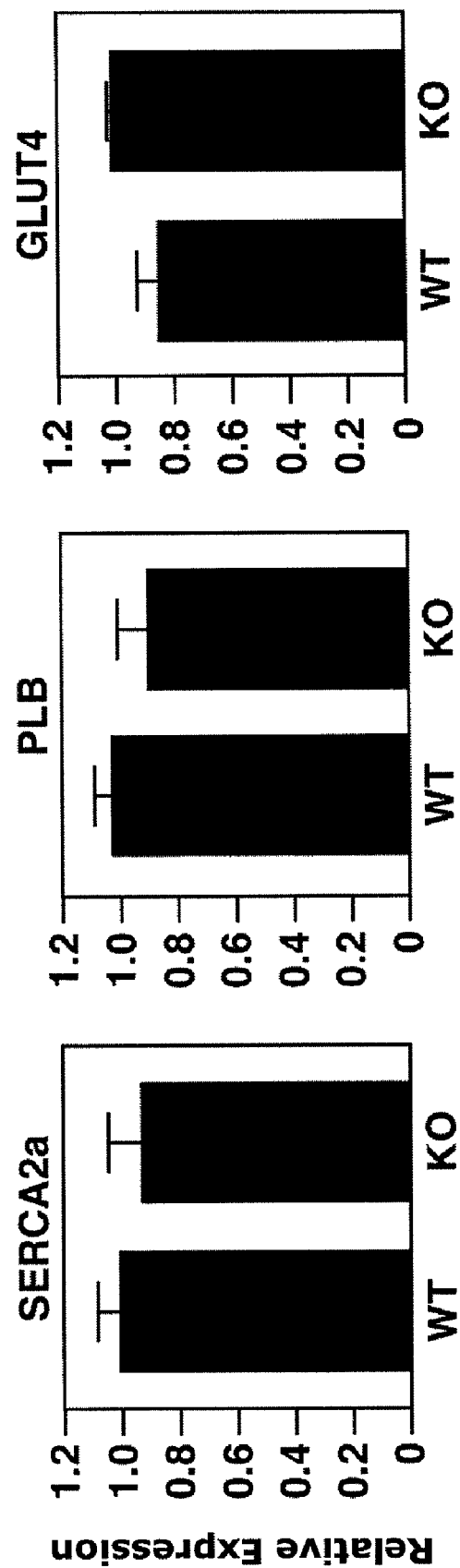
FIG. 20—Real-time PCR analysis of thyroid hormone receptor signaling targets. Transcripts for SERCA2a and PLB, and GLUT4 were detected by real-time PCR in hearts from wild-type and miR-208$^{-/-}$ mice. Values are expressed as fold-change in expression (±SEM) compared to wild-type mice.

These results suggest that miR-208 acts, at least in part, by repressing expression of the TR co-regulator THRAP1, which can exert positive and negative effects on transcription (Pavri et al., 2005; Park et al., 2005). The TR acts through a negative TRE to repress βMHC expression in the adult heart (Morkin, 2000). Thus, the increase in THRAP1 expression in the absence of miR-208 would be predicted to enhance the repressive activity of the TR toward βMHC expression, consistent with the blockade to βMHC expression in miR-208$^{-/-}$ hearts. In contrast, the regulation of α- and βMHC expression during development is independent of T3 signaling (Morkin, 2000) and is unaffected by miR-208. It is notable that other TR target genes, such as phospholamban (PLB) and sarco (endo)plasmic reticulum calcium ATPase (SERCA) 2a and glucose transporter (GLUT) 4 were expressed normally in miR-208$^{-/-}$ mice (FIG. 20). It has been proposed that the βMHC gene may respond to specific TR isoforms (Kinugawa et al., 2001; Mansen et al., 2001; Kinugawa et al., 2001). Perhaps THRAP1 acts on specific TR isoforms or selectively on a subset of TR-dependent genes via interactions with promoter-specific factors. Because miRNAs generally act through multiple downstream targets to exert their effects, additional targets are also likely to contribute to the effects of miR-208 on cardiac growth and gene expression.

Relatively minor increases in βMHC composition, as occur during cardiac hypertrophy and heart failure, can reduce myofibrillar ATPase activity and systolic function (Abraham et al., 2002). Thus, therapeutic manipulation of miR-208 expression or interaction with its mRNA targets could potentially enhance cardiac function by suppressing βMHC expression. Based on the profound influence of miR-208 on the cardiac stress response, and the regulation of numerous miRNAs in the diseased heart (van Rooij et al., 2006), the inventors anticipate that miRNAs will prove to be key regulators of the functions and responses to disease of the adult heart and possibly other organs.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

XI. REFERENCES

The following references, to the extent that they provide exemplary procedural or other details supplementary to those set forth herein, are specifically incorporated herein by reference.

U.S. Pat. No. 4,873,191
U.S. Pat. No. 5,604,251
U.S. Pat. No. 5,844,107
U.S. Pat. No. 5,877,302
U.S. Pat. No. 5,972,900
U.S. Pat. No. 5,972,901
U.S. Pat. No. 6,008,336
U.S. Pat. No. 6,077,835
U.S. Pat. No. 6,200,801
U.S. Publn. 20020150626
U.S. Publn. 20030032615
U.S. Publn. 20030203865
U.S. Publn. 20040048787
Abraham et al., *Mol. Med.*, 8:750-760, 2002.
Ambros, *Cell*, 113(6):673-676, 2003.
Angel et al., *Cell*, 49:729, 1987b.
Angel et al., *Mol. Cell. Biol.*, 7:2256, 1987a.
Atchison and Perry, *Cell*, 46:253, 1986.
Atchison and Perry, *Cell*, 48:121, 1987.
Babak et al., *RNA* 10:1813-1819, 2004.
Baichwal and Sugden, In: *Gene Transfer*, Kucherlapati (Ed.), Plenum Press, NY, 117-148, 1986.
Baldwin and Haddad, *J. Appl. Physiol.*, 90:345-357, 2001.
Banerji et al., *Cell*, 27(2 Pt 1):299-308, 1981.
Banerji et al., *Cell*, 33(3):729-740, 1983.
Barad et al., *Genome Res.* 14:2486-2494, 1997.
Barnes et al., *J. Biol. Chem.*, 272(17):11510-11517, 1997.
Benvenisty and Neshif, *Proc. Natl. Acad. Sci. USA*, 83(24): 9551-9555, 1986.
Berkhout et al., *Cell*, 59:273-282, 1989.
Bhavsar et al., *Genomics*, 35(1):11-23, 1996.
Blanar et al, *EMBO J.*, 8:1139, 1989.
Bodine and Ley, *EMBO J.*, 6:2997, 1987.
Boshart et al., *Cell*, 41:521, 1985.
Bosze et al., *EMBO J.*, 5(7):1615-1623, 1986.
Braddock et al., *Cell*, 58:269, 1989.
Brennecke et al., *Cell*, 113:25-36, 2003.
Brinster et al., *Proc. Natl. Acad. Sci. USA*, 82(13):4438-4442, 1985.
Bristow, *Cardiology*, 92:3-6, 1999.
Bulla and Siddiqui, *J. Virol.*, 62:1437, 1986.
Calin et al., *Proc. Natl. Acd. Sci. USA*, 99:15524-15529, 2002.
Campbell and Villarreal, *Mol. Cell. Biol.*, 8:1993, 1988.
Campere and Tilghman, *Genes and Dev.*, 3:537, 1989.
Campo et al., *Nature*, 303:77, 1983.
Carrington et al. *Science*, 301(5631):336-338, 2003.
Celander and Haseltine, *J. Virology*, 61:269, 1987.
Celander et al., *J. Virology*, 62:1314, 1988.
Chandler et al., *Cell*, 33:489, 1983.
Chang and Karin, *Nature*, 410(6824):37-40, 2001.
Chang et al., *Biochim. Biophys. Acta*, 1092(2):153-160, 1991.
Chang et al., *Mol. Cell. Biol.*, 9:2153, 1989.
Chang et al., *Nature*, 430(7001):785-789, 2004.
Chatterjee et al., *Proc. Natl. Acad. Sci. USA*, 86:9114, 1989.
Chen and Okayama, *Mol. Cell. Biol.*, 7(8):2745-2752, 1987.
Chen et al., *Mol. Cell. Endocrinol.*, 162:45-55, 2000.
Chen et al., *Science*, 303(5654):83-86, 2004.
Choi et al., *Cell*, 53:519, 1988.
Coffin, In: *Virology*, Fields et al. (Eds.), Raven Press, NY, 1437-1500, 1990.
Cohen et al., *J. Cell. Physiol.*, 5:75, 1987.
Costa et al, *Mol. Cell. Biol.*, 8:81, 1988.
Couch et al., *Am. Rev. Resp. Dis.*, 88:394-403, 1963.
Coupar et al., *Gene*, 68:1-10, 1988.
Cripe et al., *EMBO J.*, 6:3745, 1987.
Culotta and Hamer, *Mol. Cell. Biol.*, 9:1376, 1989.
Dandolo et al., *J. Virology*, 47:55-64, 1983.
De Villiers et al., *Nature*, 312(5991):242-246, 1984.
Deschamps et al., *Science*, 230:1174-1177, 1985.
Dubensky et al., *Proc. Natl. Acad. Sci. USA*, 81:7529-7533, 1984.
Durand et al., *Ann. Med.*, 27:311-317, 1995.
Edbrooke et al., *Mol. Cell. Biol.*, 9:1908, 1989.
Edgerton and Roy, *J. Appl. Physiol.*, 89:1224-1231, 2000.
Edlund et al., *Science*, 230:912-916, 1985.
Eichhorn and Bristow, *Circulation*, 94:2285-2296, 1996.
EPO 0273085
Fechheimer, et al., *Proc Natl. Acad. Sci. USA*, 84:8463-8467, 1987.
Feng and Holland, *Nature*, 334:6178, 1988.
Ferkol et al., *FASEB J.*, 7:1081-1091, 1993.
Firak and Subramanian, *Mol. Cell. Biol.*, 6:3667, 1986.
Fitts et al., *J. Appl. Physiol.*, 89:823-839, 2000.
Foecking and Hofstetter, *Gene*, 45(1):101-105, 1986.
Fraley et al., *Proc. Natl. Acad. Sci. USA*, 76:3348-3352, 1979.
Franz et al., *Cardioscience*, 5(4):235-43, 1994.
Friedman et al., *Genes Devel.*, 3:1314, 1989.
Fujita et al., *Cell*, 49:357, 1987.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Ghosh-Choudhury et al., *EMBO J.*, 6:1733-1739, 1987.
Gilles et al., *Cell*, 33:717, 1983.
Gloss et al., *EMBO J.*, 6:3735, 1987.
Godbout et al., *Mol. Cell. Biol.*, 8:1169, 1988.
Gomez-Foix et al., *J. Biol. Chem.*, 267:25129-25134, 1992.
Goodbourn and Maniatis, *Proc. Natl. Acad. Sci. USA*, 85:1447, 1988.
Goodbourn et al., *Cell*, 45:601, 1986.
Gopal, *Mol. Cell. Biol.*, 5:1188-1190, 1985.
Gopal-Srivastava et al., *J. Mol. Cell. Biol.* 15(12):7081-7090, 1995.

Graham and Prevec, In: *Methods in Molecular Biology: Gene Transfer and Expression Protocol*, Murray (Ed.), Humana Press, Clifton, N.J., 7:109-128, 1991.
Graham and Van Der Eb, *Virology*, 52:456-467, 1973.
Graham et al., *J. Gen. Virl.*, 36(1):59-74, 1977.
Greene et al., *Immunology Today*, 10:272, 1989
Grishok et al., *Cell*, 106:23-34, 2001.
Grosschedl and Baltimore, *Cell*, 41:885, 1985.
Grunhaus and Horwitz, *Seminar in Virology*, 3:237-252, 1992.
Harland and Weintraub, *J. Cell Biol.*, 101(3):1094-1099, 1985.
Haslinger and Karin, *Proc. Natl. Acad. Sci. USA*, 82:8572, 1985.
Hauber and Cullen, *J. Virology*, 62:673, 1988.
Hen et al., *Nature*, 321:249, 1986.
Hensel et al., *Lymphokine Res.*, 8:347, 1989.
Hermonat and Muzycska, *Proc. Natl. Acad. Sci. USA*, 81:6466-6470, 1984.
Herr and Clarke, *Cell*, 45:461, 1986.
Hersdorffer et al., *DNA Cell Biol.*, 9:713-723, 1990.
Herz and Gerard, *Proc. Natl. Acad. Sci. USA*, 90:2812-2816, 1993.
Hill et al., *Circulation*, 101:2863-2869, 2000.
Hirochika et al., *J. Virol.*, 61:2599, 1987.
Hirsch et al., *Mol. Cell. Biol.*, 10:1959, 1990.
Holbrook et al., *Virology*, 157:211, 1987.
Horlick and Benfield, *Mol. Cell. Biol.*, 9:2396, 1989.
Horwich et al. *J. Virol.*, 64:642-650, 1990.
Huang et al., *Cell*, 27:245, 1981.
Hug et al., *Mol. Cell. Biol.*, 8:3065, 1988.
Hutvagner et al., *PLoS Biol.*, 2(4):E98, 2004.
Hwang et al., *Mol. Cell. Biol.*, 10:585, 1990.
Imagawa et al., *Cell*, 51:251, 1987.
Imbra and Karin, *Nature*, 323:555, 1986.
Imler et al., *Mol. Cell. Biol.*, 7:2558, 1987.
Imperiale and Nevins, *Mol. Cell. Biol.*, 4:875, 1984.
Ito and Roeder, *Trends Endocrinol. Metab.*, 12:127-134, 2001.
Jakobovits et al., *Mol. Cell. Biol.*, 8:2555, 1988.
Jameel and Siddiqui, *Mol. Cell. Biol.*, 6:710, 1986.
Jaynes et al., *Mol. Cell. Biol.*, 8:62, 1988.
Johnson et al., *Mol. Cell. Biol.*, 9:3393, 1989.
Jones and Shenk, *Cell*, 13:181-188, 1978.
Kadesch and Berg, *Mol. Cell. Biol.*, 6:2593, 1986.
Kaneda et al., *Science*, 243:375-378, 1989.
Karin et al., *Mol. Cell. Biol.*, 7:606, 1987.
Karin et al., *Mol. Cell. Biol.*, 7:606, 1987.
Karlsson et al., *EMBO J*, 5:2377-2385, 1986.
Katinka et al., *Cell*, 20:393, 1980.
Katinka et al., *Nature*, 290:720, 1981.
Kato et al, *J. Biol. Chem.*, 266:3361-3364, 1991.
Kawamoto et al., *Mol. Cell. Biol.*, 8:267, 1988.
Kelly et al., *J. Cell Biol.*, 129(2):383-396, 1995.
Kiledjian et al., *Mol. Cell. Biol.*, 8:145, 1988.
Kimura et al., *Dev. Growth Differ.* 39(3):257-265, 1997.
Kinugawa et al., *Circ. Res.*, 89:591-598, 2001.
Kinugawa et al., *J. Clin. Endocrinol. Metab.*, 86:5089-5090, 2001.
Kiriazis and Kranias, *Annu. Rev. Physiol.*, 62:321-351, 2000.
Klamut et al., *Mol. Cell. Biol.*, 10:193, 1990.
Klein et al., *Nature*, 327:70-73, 1987.
Koch et al., *Mol. Cell. Biol.*, 9:303, 1989.
Krek et al., *Nat. Genet.*, 37:495-500, 2005.
Krek et al., *Nature Genetics*, 37:495-500, 2005.
Krenz and Robbins, *J. Am. Coil. Cardiol.*, 44:2390-2397, 2004.
Kriegler and Botchan, In: *Eukaryotic Viral Vectors*, Gluzman (Ed.), Cold Spring Harbor: Cold Spring Harbor Laboratory, NY, 1982.
Kriegler and Botchan, *Mol. Cell. Biol.*, 3:325, 1983a.
Kriegler et al., *Cell*, 38:483, 1984.
Kriegler et al., *Cell*, 53:45, 1988.
Kriegler et al., In: *Gene Expression*, Alan Liss (Ed.), Hamer and Rosenberg, New York, 1983b.
Kruitzfeldt et al., *Nature*, 438:685-689, 2005.
Kuhl et al., *Cell*, 50:1057, 1987.
Kunz et al., *Nucl. Acids Res.*, 17:1121, 1989.
Lagos-Quintana et al., *Science*, 294(5543):853-858, 2001.
LaPointe et al., *Hypertension* 27(3 Pt 2):715-22, 1996.
LaPointe et al., *J. Biol. Chem.*, 263(19):9075-8, 1988.
Larsen et al., *Proc Natl. Acad. Sci. USA.*, 83:8283, 1986.
Laspia et al., *Cell*, 59:283, 1989.
Latimer et al., *Mol. Cell. Biol.*, 10:760, 1990.
Lau et al., *Science*, 294(5543):858-862, 2001.
Le Gal La Salle et al., *Science*, 259:988-990, 1993.
Lee and Ambros, *Science*, 294(5543):862-864, 2001.
Lee et al., *Nature*, 294:228, 1981.
Lee et al., *Nucleic Acids Res.*, 12:4191-206, 1984.
Leung et al., *Proc. Natl. Acad. Sci. USA*, 48:18125-18130, 2006.
Levinson et al., *Nature*, 295:79, 1982.
Levrero et al., *Gene*, 101:195-202, 1991.
Lin et al., *Mol. Cell. Biol.*, 10:850, 1990.
Liu et al., *Proc Natl Acad Sci USA* 101:9740-9744, 2004.
Luria et al., *EMBO J.*, 6:3307, 1987.
Lusky and Botchan, *Proc. Natl. Acad. Sci. USA*, 83:3609, 1986.
Lusky et al., *Mol. Cell. Biol.*, 3:1108, 1983.
Macejak and Sarnow, *Nature*, 353:90-94, 1991.
Majors and Varmus, *Proc. Natl. Acad. Sci. USA*, 80:5866, 1983.
Mann et al., *Cell*, 33:153-159, 1983.
Mansen et al., *Mol. Endocrinol.*, 15:2106-2114, 2001.
Markowitz et al., *J. Virol.*, 62:1120-1124, 1988.
McNeall et al., *Gene*, 76:81, 1989.
Meister and Tuschl, *Nature*, 431:343-9, 2004.
Miksicek et al., *Cell*, 46:203, 1986.
Molkentin et al., *Cell* 93:215-228, 1998.
Mordacq and Linzer, *Genes and Dev.*, 3:760, 1989.
Moreau et al., *Nucl. Acids Res.*, 9:6047, 1981.
Morkin, *Microsc. Res. Tech.*, 50:522-531, 2000.
Moss et al., *Biol. Chem.*, 271(49):31688-31694, 1996.
Muesing et al., *Cell*, 48:691, 1987.
Naya et al., *J Biol Chem*, 275(7):4545-4548, 2000.
Ng et al., *Nuc. Acids Res.*, 17:601, 1989.
Nicolas and Rubinstein, In: *Vectors: A survey of molecular cloning vectors and their uses*, Rodriguez and Denhardt (Eds), Stoneham: Butterworth, 494-513, 1988.
Nicolau and Sene, *Biochim. Biophys. Acta*, 721:185-190, 1982.
Nicolau et al., *Methods Enzymol.*, 149:157-176, 1987.
Ojamaa et al., *Endocrinology*, 141:2139-2144, 2000.
Ondek et al., *EMBO J.*, 6:1017, 1987.
Omitz et al., *Mol. Cell. Biol.*, 7:3466, 1987.
Palmiter et al., *Nature*, 300:611, 1982.
Pantos et al., *Horm. Metab. Res.*, 38:308-313, 2006.
Park et al., *Mol. Cell.*, 19:643-653, 2005.
Paskind et al., *Virology*, 67:242-248, 1975.
Pasquinelli and Ruvkun, *Ann. Rev. Cell Dev. Biol.*, 18:495-513, 2002.
Pavri et al., *Mol. Cell.*, 18:83-96, 2005.
PCT Appln. WO 0071096
PCT Appln. WO 84/03564

PCT Appln. WO 98/33791
Pech et al., *Mol. Cell. Biol.*, 9:396, 1989.
Pelletier and Sonenberg, *Nature*, 334(6180):320-325, 1988.
Perales et al., *Proc. Natl. Acad. Sci. USA*, 91:4086-4090, 1994.
Perez-Stable and Constantini, *Mol. Cell. Biol.*, 10:1116, 1990.
Physicians Desk Reference
Picard and Schaffner, *Nature*, 307:83, 1984.
Pinkert et al., *Genes and Dev.*, 1:268, 1987.
Ponta et al., *Proc. Natl. Acad. Sci. USA*, 82:1020, 1985.
Porton et al., *Mol. Cell. Biol.*, 10:1076, 1990.
Potter et al., *Proc. Natl. Acad. Sci. USA*, 81:7161-7165, 1984.
Queen and Baltimore, *Cell*, 35:741, 1983.
Quinn et al., *Mol. Cell. Biol.*, 9:4713, 1989.
Racher et al., *Biotechnology Techniques*, 9:169-174, 1995.
Ragot et al., *Nature*, 361:647-650, 1993.
Redondo et al., *Science*, 247:1225, 1990.
Reisman and Rotter, *Mol. Cell. Biol.*, 9:3571, 1989.
Remington's Pharmaceutical Sciences, 15$^{th}$ ed., pages 1035-1038 and 1570-1580, Mack Publishing Company, Easton, Pa., 1980.
Renan, *Radiother. Oncol.*, 19:197-218, 1990.
Resendez Jr. et al., *Mol. Cell. Biol.*, 8:4579, 1988.
Rich et al., *Hum. Gene Ther.*, 4:461-476, 1993.
Ridgeway, In: *Vectors: A Survey of Molecular Cloning Vectors and Their Uses*, Rodriguez et al. (Eds.), Stoneham: Butterworth, 467-492, 1988.
Ripe et al., *Mol. Cell. Biol.*, 9:2224, 1989.
Rippe, et al., *Mol. Cell. Biol.*, 10:689-695, 1990.
Rittling et al., *Nuc. Acids Res.*, 17:1619, 1989.
Rosen et al., *Cell*, 41:813, 1988.
Rosenfeld et al., *Science*, 252:431-434, 1991.
Rosenfeld, et al., *Cell*, 68:143-155, 1992.
Roux et al., *Proc. Natl. Acad. Sci. USA*, 86:9079-9083, 1989.
Sakai et al, *Genes and Dev.*, 2:1144, 1988.
Sambrook and Russell, Molecular Cloning: A Laboratory Manual 3$^{rd}$ Ed., Cold Spring Harbor Laboratory Press, 2001.
Satake et al., *J Virology*, 62:970, 1988.
Schaffner et al., *J. Mol. Biol.*, 201:81, 1988.
Schuyler and Yarbrough, *Basic Res. Cardiol.*, 85:481-494, 1990.
Searle et al., *Mol. Cell. Biol.*, 5:1480, 1985.
Sempere et al., *Genome Biol* 5:R13, 2004.
Sharp and Marciniak, *Cell*, 59:229, 1989.
Shaul and Ben-Levy, *EMBO J.*, 6:1913, 1987.
Sherman et al., *Mol. Cell. Biol.*, 9:50, 1989.
Shingara et al., *RNA* 11:1461-1470, 2005.
Sleigh and Lockett, *J. EMBO*, 4:3831, 1985.
Spalholz et al., *Cell*, 42:183, 1985.
Spandau and Lee, *J. Virology*, 62:427, 1988.
Spandidos and Wilkie, *EMBO J.*, 2:1193, 1983.
Stephens and Hentschel, *Biochem. J.*, 248:1, 1987.
Stratford-Perricaudet and Perricaudet, In: *Human Gene Transfer*, Eds, Cohen-Haguenauer and Boiron, John Libbey Eurotext, France, 51-61, 1991.
Stratford-Perricaudet et al., *Hum. Gene. Ther.*, 1:241-256, 1990.
Stuart et al., *Nature*, 317:828, 1985.
Sullivan and Peterlin, *Mol. Cell. Biol.*, 7:3315, 1987.
Swartzendruber and Lehman, *J. Cell. Physiology*, 85:179, 1975.
Takebe et al., *Mol. Cell. Biol.*, 8:466, 1988.
Tavernier et al., *Nature*, 301:634, 1983.
Taylor and Kingston, *Mol. Cell. Biol.*, 10:165, 1990a.
Taylor and Kingston, *Mol. Cell. Biol.*, 10:176, 1990b.
Taylor et al., *J. Biol. Chem.*, 264:15160, 1989.
Temin, In: *Gene Transfer*, Kucherlapati (Ed.), NY, Plenum Press, 149-188, 1986.
The Merck Index, Eleventh Edition
Thiesen et al., *J. Virology*, 62:614, 1988.
Top et al., *J. Infect. Dis.*, 124:155-160, 1971.
Treisman, *Cell*, 46(4):567-174, 1986
Tronche et al., *Mol. Biol. Med.*, 7:173, 1990.
Tronche et al., *Mol. Cell. Biol.*, 9(11):4759-4766, 1989.
Trudel and Constantini, *Genes and Dev.*, 6:954, 1987.
Tsika et al., *Am. J. Physiol. Cell Physiol.*, 283:C1761-C1775, 2002.
Tur-Kaspa et al., *Mol. Cell. Biol.*, 6:716-718, 1986.
Tyndell et al., *Nuc. Acids. Res.*, 9:6231, 1981.
Vadaszova et al., *Physiol. Res.* 53(1):S57-61, 2004.
van Rooij et al., *Proc. Natl. Acad. Sci. USA*, 103(48):18255-18260, 2006.
Vannice and Levinson, *J. Virology*, 62:1305, 1988.
Varmus et al., *Cell*, 25:23-36, 1981.
Vasseur et al., *Proc Natl. Acad. Sci. USA*, 77:1068, 1980.
Wagner et al., *Proc. Natl. Acad. Sci. USA* 87(9):3410-3414, 1990.
Wang and Calame, *Cell*, 47:241, 1986.
Weber et al., *Cell*, 36:983, 1984.
Wei et al., *J. Endocrinol. Invest.*, 28:8-11, 2005.
Weinberger et al. *Mol. Cell. Biol.*, 8:988, 1984.
Winoto and Baltimore, *Cell*, 59:649, 1989.
Wong et al., *Gene*, 10:87-94, 1980.
Wu and Wu, *Adv. Drug Delivery Rev.*, 12:159-167, 1993.
Wu and Wu, *Biochemistry*, 27: 887-892, 1988.
Wu and Wu, *J. Biol. Chem.*, 262:4429-4432, 1987.
Xu et al., *Curr. Biol.*, 13:790-795, 2003.
Yamauchi-Takihara, et. al., *Proc. Natl. Acad. Sci. USA*, 86(10):3504-3508, 1989.
Yang and Russell, *Proc. Natl. Acad. Sci. USA*, 87:4144-4148, 1990.
Yao and Eghbali, *Circ. Res.* 71:831-839, 1992.
Young et al., In: *Handbook of Applied Therapeutics*, 7.1-7.12 and 9.1-9.10, 1989.
Yutzey et al. *Mol. Cell. Biol.*, 9:1397, 1989.
Zelenin et al., *FEBS Lett.*, 287(1-2):118-120, 1991.
Zeng et al., *Cancer Res.*, 62(13):3630-3635, 2002.
Ziober and Kramer, *J. Bio. Chem.*, 271(37):22915-22, 1996.

What is claimed is:

1. A method of treating or preventing pathologic cardiac hypertrophy, or heart failure in a patient in need thereof comprising:
   administering to said patient an antisense oligonucleotide comprising a sequence complementary to miR-208, wherein expression or activity of miR-208 in heart cells of the patient is inhibited following administration of said antisense oligonucleotide, thereby treating or preventing the pathologic cardiac hypertrophy.

2. The method of claim 1, wherein administering comprises intravenous administration or direct injection into cardiac tissue.

3. The method of claim 1, wherein administering comprises oral, transdermal, sustained release, controlled release, delayed release, suppository, or sublingual administration of said antisense oligonucleotide.

4. The method of claim 1, further comprising administering to said patient a second cardiac hypertrophic therapy.

5. The method of claim 4, wherein said second therapy is selected from the group consisting of a beta blocker, an ionotrope, a diuretic, ACE-1, AII antagonist, BNP, a $Ca^{++}$-blocker, an endothelin receptor antagonist, or an HDAC inhibitor.

6. The method of claim 4, wherein said second therapy is administered at the same time as the antisense oligonucleotide.

7. The method of claim 4, wherein said second therapy is administered either before or after the antisense oligonucleotide.

8. The method of claim 1, wherein treating comprises improving one or more symptoms of pathologic cardiac hypertrophy or heart failure.

9. The method of claim 1, wherein treating comprises delaying the transition from cardiac hypertrophy to heart failure.

10. The method of claim 8, wherein said one or more improved symptoms comprises increased exercise capacity, increased cardiac ejection volume, decreased left ventricular end diastolic pressure, decreased pulmonary capillary wedge pressure, increased cardiac output, or cardiac index, lowered pulmonary artery pressures, decreased left ventricular end systolic and diastolic dimensions, decreased left and right ventricular wall stress, decreased wall tension, increased quality of life, and decreased disease related morbidity or mortality.

11. The method of claim 1, wherein the patient is at risk of developing pathologic cardiac hypertrophy or heart failure and exhibits one or more of a list of risk factors comprising long standing uncontrolled hypertension, uncorrected valvular disease, chronic angina, recent myocardial infarction, congenital predisposition to heart disease or pathological hypertrophy.

12. The method of claim 11, wherein the patient at risk is diagnosed as having a genetic predisposition to cardiac hypertrophy.

13. The method of claim 11, wherein the patient at risk has a familial history of cardiac hypertrophy.

14. The method of claim 1, wherein the patient is diagnosed with dilated cardiomyopathy.

15. The method of claim 1, wherein progression of cardiac hypertrophy is inhibited in the patient following administration of the antisense oligonucleotide.

16. The method of claim 1, wherein exercise tolerance is increased in the patient following administration of the antisense oligonucleotide.

17. The method of claim 1, wherein morbidity is decreased in the patient following administration of the antisense oligonucleotide.

18. The method of claim 1, wherein the antisense oligonucleotide comprises at least one chemical modification.

19. The method of claim 18, wherein the antisense oligonucleotide comprises 2'-O-methyl oligoribonucleotides.

20. The method of claim 18, wherein the antisense oligonucleotide is an antagomir.

21. The method of claim 1, wherein the antisense oligonucleotide comprises a sequence that is complementary to a mature miR-208 sequence.

22. The method of claim 21, wherein the antisense oligonucleotide comprises a sequence that is complementary to SEQ ID NO: 5.

23. The method of claim 1, wherein the antisense oligonucleotide is administered to the patient by a subcutaneous route of administration.

24. The method of claim 1, wherein the antisense oligonucleotide is encoded by an expression vector, and wherein the antisense oligonucleotide is under the transcriptional control of a promoter.

25. The method of claim 24, wherein the promoter is a cardiac-specific promoter.

26. A method of treating myocardial infarction in a patient in need thereof comprising:
   administering to said patient an antisense oligonucleotide comprising a sequence complementary to miR-208, wherein expression or activity of miR-208 in heart cells of the patient is inhibited following administration of said antisense oligonucleotide, thereby treating the myocardial infarction.

27. The method of claim 26, wherein administering comprises intravenous, subcutaneous, oral, transdermal, sustained release, controlled release, delayed release, suppository, or sublingual, administration or direct injection into cardiac tissue.

28. The method of claim 26, wherein the antisense oligonucleotide comprises at least one chemical modification.

29. The method of claim 28, wherein the antisense oligonucleotide comprises 2'-O-methyl oligoribonucleotides.

30. The method of claim 28, wherein the antisense oligonucleotide is an antagomir.

31. The method of claim 26, wherein the antisense oligonucleotide comprises a sequence that is complementary to a mature miR-208 sequence.

32. The method of claim 26, wherein the antisense oligonucleotide comprises a sequence that is complementary to SEQ ID NO: 5.

33. The method of claim 26, wherein the antisense oligonucleotide is encoded by an expression vector, and wherein the antisense oligonucleotide is under the transcriptional control of a promoter.

34. The method of claim 33, wherein the promoter is a cardiac-specific promoter.

* * * * *